(12) United States Patent
Rock et al.

(10) Patent No.: US 6,613,553 B1
(45) Date of Patent: Sep. 2, 2003

(54) ENOYL REDUCTASES AND METHODS OF USE THEREOF

(75) Inventors: Charles O. Rock, Bartlett, TN (US); Richard John Heath, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/498,520

(22) Filed: Feb. 4, 2000

(51) Int. Cl.$^7$ .................................................. C12N 9/02
(52) U.S. Cl. ........................................ 435/189; 435/183
(58) Field of Search ...................... 424/184.1, 185.1, 424/192.1, 244.1, 243.1, 246.1, 234.1, 265.1, 274.1, 94.1, 94.4; 435/189, 190, 191, 192

(56) References Cited

U.S. PATENT DOCUMENTS 5,759,832 A    6/1998   Gentry et al.

FOREIGN PATENT DOCUMENTS

WO    98/06734    *  2/1998
WO    98/26072    *  6/1998

OTHER PUBLICATIONS

Ellis, R.W. in "Vaccines", Chapter 29 Plotkin S A et al. eds., W.B. Saunders Company, p. 571, 1998.*
Nelson et al, Nature 399: 323–329, May 27, 1999.*
Baldock et al., Science, 1996, 274: 2107.
Banerjee et al., 1994, Science, 263:227.
Bergler et al., 1992, J. Gen. Microbiol., 138:2093.
Bhargava et al., 1996, Am J. Infect. Control, 24: 209.
Duran et al., 1993, J. Biol. Chem., 268: 22391.
Gadda et al., 1998, Biochemistry, 37: 6154.
Gadda et al., Arch. Biochem. Biophys., 1999, 363: 309.
Gadda et al., 1997, J. Biol. Chem. 272:5563.
Heasley et al., 1996, Biochem. Biophys. Res. Commun. 225:6.
Heath et al., 1995, J. Biol. Chem., 270: 26538.
Heath et al., 1999, J. Biol. Chem. 274:11110–11114.
Heath et al., 1996, J. Biol. Chem. 271:1833–6.
Heath et al., 1998, J. Biol. Chem. 273:30316.
Hoang et al., 1999, J. Bacteriol. 181:5489.
Komunieki et al., 1985, J. Biol. Chem., 260: 4770.
Komunieki et al., 1989, Biochim. Biophys. Acta, 975: 127.
Levy et al., 1999, Nature (London), 398: 383.
McMurray et al., 1998, Nature(London) 394:531.
Rock et al., 1996, Biochim. Biophys. Acta 1302:1.
Rouse et al., 1995, Antimicrobiol. Agents. Chem., 39:2472.
Rozwarski et al., 1998, Science, 279: 98.
Stewart et al., 1999, J. Mol. Biol., 290: 859.
Tchorzewski et al., 1994, Eur. J. Biochem. 226:841.
Thorpe et al., 1995, FASEB J. 9:718.
Tsay et al., 1992, J. Biol. Chem., 267: 6807–14.
Ward et al., 1999, Biochemistry, 38: 12514.

* cited by examiner

Primary Examiner—Patricia A. Duffy
(74) Attorney, Agent, or Firm—Licata & Tyrrell P.C.

(57) ABSTRACT

The present provides structurally related enzymes that act as enoyl reductases. These enoyl reductases share a common amino acid consensus sequence, and bind a flavin cofactor. One particular enoyl reductase provided, FabK, catalyzes the identical reaction as the NADH-dependent enoyl-ACP reductase, FabI. Nucleic acids encoding the enoyl reductases, the enoyl reductases, and anitbodies for the enoyl reductases are also included. Methods are also provides for identifying agents that can act to prevent and/or treat bacterial infections.

8 Claims, 7 Drawing Sheets

```
S. pneumoniae    ------------MKTRITELLKIDYPIFQGGMAWADGDLAGAVSKAGGLGIIGGGNAF.KEVVKANIDKINSLTDKPFGVN
Ent. faecalis    MKCTYLRTKGRIKSMNQELCELLGINYPIFQGGMAWADASLASAVSNAGGLGIIAGNAF.KEVVKKEIKKVKELTEQPFGVN
C. difficile     ------------MNKICKILNIKYPVIDGGMAMVATASLASAVSNAGGLGIIAAGNAF.KEAIKKGIVECKKLTDKPFGVN
P. aeruginosa    ------------MGVFRTRFTETFGVEHPIMQGGEQMVGRAEVAAAVANAGGLATLSALTQPSPEALAAEIARCELTDRPFGVN LMLL...SPFV.EDIVDLVIEEGVKVVTIGAGNFSKYTERFHEAGIIVIPVVPSVALAKRMEKICADAVIAEGMEAGGHIS...KLTTETLVRQVATAIS
                 IMLL...SFFA.DEIVDLVCEEQVPVVTIGAGNFAKYMARFEENIKVIPVVPSVALAKRYEKIGADAVIFEGMEAGGHIS...KLTTFSGLPQIVDAVS
                 VMLM...SPFV.DDIIDLIEEKVQVITIGAGNPAKYMDRLKEAGTKVIPVVPTIALAQRMEKLGATAVIAECTEGGHIS...ELTTVVLVPQVADAVN
                 LTLLPTQKPVPYAEYRAAIIEAGIRVVETAGNDPGEHIAEFRRHGVKVIHKCTAVRHALRAERLGVDAVSIDGFECRGHPGEDDIPGIVLPAAANRLR ----FAD----
                 IPVIAAGGIADGEGAAAAGFMLGAEAVQVGTRFVAKESNAHENYIEKILKAREIDITISAQHFGHAVRAIKNQMTRDFELAEKDAFKQEDPDLEIFEQM
                 IPVIAAGGIGDGRGMAAAFMLGAEAVQVGLTRFLIAKECNVHPDYKQKVLKARDLDAVITCQHFGHAVITGHFKQELQKEVPDLEMFEKI
                 IPVIAAGGIVDGRGIAASFALGASAVQVGTRFICSEECSVHSNYKNLVLKAKDRDAIVTGRSTGHFVRTLKNKLSKEFLKMEQNGATPEE.....LDKK
                 VPITASGGFADGRGLVAALALGADAINMGTRFLAVRECPIHPAVKAAIRAADERSIDLIMRSLRNIARVARNAISQEVLAIE...ARGGAGYADIAALV GAGALAKAVVHGEDVDGGSVMAGQIAGLVSKEETAEEILKDIYYGAAKKIQEEASRWTGVVRND
                 GQGALRKAVVDGDMDYGSVMAGQIAGLHKEEIAQEIIDSLMSECKAIVHKMNQRWG------
                 GTGALRFATVDGLIEKGSFMAGQSAAMVKEITPCKEIIEAVVNQAREIVPAIEL--------
                 SGQRGRGVYQQGETDLGIWSAGMVQGLIDDEPACAELLRDIVEQARQLVRQRLEGMLAGV---
```

FIG. 1B

```
FABL_BACSU  ------MEQNKCALVICSSRGVGKAAATRLA..ENGYNIVINYARSKKALETAEEIE.KIGVKVLVVKANVGQPAKIKEMFQQIDET
FABL_HPYLO  MNGSNHMKNKTLVISGATRGIGKAIFVRFA...QSGVNIAFTYNKNVEEANKIIEDVEQKYSIKAKAYSLNVLEPEQYTELFKQIDAD
FABI_ECOLI  ---MGFLSGKRILVIGVASKLSIAYGIAQAMHREGAELAFTYQNDKLKGR..VEEFAAQLGSDI.VLQCDVAEDASIDTMFAELGKV
                                                                                        +        +

FGRLEVFVNN.A......ASSVLRPVMELEETHWDWTMNINAKALEFCAQEAAKLEKNGGGHIVSISLSSIRYLENYTTVGVSRAALEALTRYLAVE
FDRVFFISN.AIIYGRSVVGGFAPFMRLKPPKGLNNIYTATVLAFVGAQEAAKRNQKIGGCAIVSLSSTGNLVYMPNYAGHGNSKNAVETMVKYAAVD
PKFLGGFWHSISFAPGDQLDGDY..VNAVTREGFKIAHDISSYSFVAMAKACRSML..NFGSALLTLSYLGAERAIPNYNVMGLAKASLEANVRYMANA
                                        +                +

LSPKQIIVNAVSGGAIDTDALKHFPNREDLLEDARQNTPAGRMVEIKDMVDTVEFLV.SSKADMIREQTIIVDGGRSLLV-----
LGEFNIRVNAVSGGPIDIDALKAFPDYVEIKEKVEEQSPLKRMGNPNDLAGAAYFLCDETQSGMLSQTIVDGGTIFK-------
MGPEGVRVNAISAGPIRTLAASGIKDFRKMLAHCEAVTPIRRTVTIEDVGNSAAFLCSDLSAG.ISGEVHVDGGFSIAAMNELELK
        +       +
```

FIG. 3

SEQUENCE LISTING

```
<160> NUMBER OF SEQ ID NOS: 62

<210> SEQ ID NO 1
<211> LENGTH: 975
<212> TYPE: DNA
<213> ORGANISM: Streptococcus pneumoniae

<400> SEQUENCE: 1
atgaaaacgc gtattacaga attattgaag attgattatc ctattttcca aggagggatg      60 gcctggpttg ctgatggtga tttggcaggg gctgtttcca aggctggagg attaggaatt     120
atcggtgggg gaaatgcccc gaaagaagtt gtcaaggcca atattgataa aatcaaatca     180
ttgactgata aacccttggg ggtcaacatc atgctcttat ctcccttgt ggaagacatc      240 gtggatctcg ttattgaaga aggtgttaaa gttgtcacaa caggagcagg aaatccaagc     300
aagtatatgg aacgtttcca tgaagctggg ataatcgtta ttcctgttgt tcctagtgtc     360
gctttagcta aacgcatgga aaaaatcggt gcagacgctg ttattgcaga aggaatggaa     420 gctgggggc atatcggtaa attaacaacc atgaccttgg tgcgacaggt agccacagct     480
atatctattc ctgttattgc tgcaggagga attgcggatg gtgaaggtgc tgcggctggc     540
tttatgctag gtgcagaggc tgtacaggtg gggacacggt tgtagttgc aaaagagtcg     600 aatgcccatc caaactacaa ggagaaaatt ttaaaagcaa gggatattga tactacgatt     660
tcagctcagc actttggtca tgctgttcgt gctattaaaa atcagttgac tagagatttt     720
gaactggctg aaaaagatgc ctttaagcaa gaagatcctg atttagaaat ctttgaacaa     780
atgggagcag gtgctctagc caaagcagtt gttcacggtg atgtggatgg tggctctgtt     840
```

-continued

```
atggcaggtc aaatcgcagg gcttgtttct aaagaagaaa cagctgaaga aatcctaaaa      900
gatttgtatt acggagccgc taagaaaatt caagaagaag cctctcgctg gacaggagtt      960
gtaagaaatg actaa                                                       975
```

<210> SEQ ID NO 2
<211> LENGTH: 324
<212> TYPE: PRT
<213> ORGANISM: Streptococcus pneumoniae

<400> SEQUENCE: 2

```
Met Lys Thr Arg Ile Thr Glu Leu Leu Lys Ile Asp Tyr Pro Ile Phe
 1               5                  10                  15

Gln Gly Gly Met Ala Trp Val Ala Asp Gly Asp Leu Ala Gly Ala Val
            20                  25                  30

Ser Lys Ala Gly Leu Gly Ile Ile Gly Gly Asn Ala Pro Lys
        35                  40                  45

Glu Val Val Lys Ala Asn Ile Asp Lys Ile Lys Ser Leu Thr Asp Lys
    50                  55                  60

Pro Phe Gly Val Asn Ile Met Leu Leu Ser Pro Phe Val Glu Asp Ile
65                  70                  75                  80

Val Asp Leu Val Ile Glu Glu Gly Val Lys Val Thr Thr Gly Ala
                85                  90                  95

Gly Asn Pro Ser Lys Tyr Met Glu Arg Phe His Glu Ala Gly Ile Ile
            100                 105                 110

Val Ile Pro Val Val Pro Ser Val Ala Leu Ala Lys Arg Met Glu Lys
        115                 120                 125

Ile Gly Ala Asp Ala Val Ile Ala Glu Gly Met Glu Ala Gly Gly His
    130                 135                 140

Ile Gly Lys Leu Thr Thr Met Thr Leu Val Arg Gln Val Ala Thr Ala
145                 150                 155                 160

Ile Ser Ile Pro Val Ile Ala Ala Gly Gly Ile Ala Asp Gly Glu Gly
                165                 170                 175

Ala Ala Ala Gly Phe Met Leu Gly Ala Glu Ala Val Gln Val Gly Thr
            180                 185                 190

Arg Phe Val Val Ala Lys Glu Ser Asn Ala His Pro Asn Tyr Lys Glu
        195                 200                 205

Lys Ile Leu Lys Ala Arg Asp Ile Asp Thr Thr Ile Ser Ala Gln His
    210                 215                 220

Phe Gly His Ala Val Arg Ala Ile Lys Asn Gln Leu Thr Arg Asp Phe
225                 230                 235                 240

Glu Leu Ala Glu Lys Asp Ala Phe Lys Gln Glu Asp Pro Asp Leu Glu
                245                 250                 255

Ile Phe Glu Gln Met Gly Ala Gly Ala Leu Ala Lys Ala Val Val His
            260                 265                 270

Gly Asp Val Asp Gly Gly Ser Val Met Ala Gly Gln Ile Ala Gly Leu
        275                 280                 285

Val Ser Lys Glu Glu Thr Ala Glu Glu Ile Leu Lys Asp Leu Tyr Tyr
    290                 295                 300

Gly Ala Ala Lys Lys Ile Gln Glu Glu Ala Ser Arg Trp Thr Gly Val
305                 310                 315                 320

Val Arg Asn Asp
```

<210> SEQ ID NO 3

<211> LENGTH: 966
<212> TYPE: DNA
<213> ORGANISM: Streptococcus mutans

<400> SEQUENCE: 3

| | | | | | |
|---|---|---|---|---|---|
| atgaaaacgc | gtattacaga | attattagat | attgaatatc | ctattttttca | aggaggaatg | 60 |
| gcttgggtag | ctgatggtga | tttagcggga | gctgtatcaa | aagctggcgg | tttaggaatt | 120 |
| atcggtggtg | gaaatgcgcc | caaagaagtt | gttaaggcga | atattgacaa | gatcaaagct | 180 |
| gtgacaaata | aaccatttgg | agtcaatatt | atgcttttat | ctccttttgc | tgatgatatt | 240 |
| gttgacttgg | ttattgaaga | aggtgtcaaa | gttgtcacaa | ctggtgcagg | taacccaggt | 300 |
| aaatatatag | aacgtttcca | tgaagcaggt | attactgtca | ttcctgttgt | tcctagtgtt | 360 |
| gctcttgcta | gacgtatgga | aaaattaggt | gctgatgccg | ttattgctga | aggaatggaa | 420 |
| gcaggtggac | atattggtaa | attaacaaca | atgactttag | tcgtcaagt | tgtagatgcc | 480 |
| gtcaacattc | ctgttatcgg | agctggtggt | gtagccgatg | gtcgtggtgc | agcggcagta | 540 |
| tttatgcttg | gtgctgaagc | cattcaggta | ggaacacgtt | ttgcagttgc | caaagaatcg | 600 |
| aatgcccatg | cgaattttaa | aaagaaaatt | ttaaaagcca | aagatattga | tactgttatt | 660 |
| tccgcgtcta | ttgttggtca | tcctgtacgt | gcaatcaaaa | ataaattatc | ttctgcctat | 720 |
| gcaactgcag | aaaagaatt | cttgcgtggt | gaaaagagtc | aagaagatat | tgaagttctt | 780 |
| ggtgctggag | ctctccgcaa | tgctgttgtt | gacggtgatg | ttgataatgg | ttctgttatg | 840 |
| gcaggtcaaa | ttgcaggatt | tgttactaaa | gaagaaactt | gtgaagaaat | tttgaaagat | 900 |
| ttatattatg | gtgcagcaaa | agtcattaag | gctgaagcag | cacgctgggc | agacgtggag | 960 |
| aaataa | | | | | | 966 |

<210> SEQ ID NO 4
<211> LENGTH: 321
<212> TYPE: PRT
<213> ORGANISM: Streptococcus mutans

<400> SEQUENCE: 4

Met Lys Thr Arg Ile Thr Glu Leu Leu Asp Ile Glu Tyr Pro Ile Phe
1               5                   10                  15

Gln Gly Gly Met Ala Trp Val Ala Asp Gly Asp Leu Ala Gly Ala Val
                20                  25                  30

Ser Lys Ala Gly Gly Leu Gly Ile Ile Gly Gly Asn Ala Pro Lys
            35                  40                  45

Glu Val Val Lys Ala Asn Ile Asp Lys Ile Lys Ala Val Thr Asn Lys
    50                  55                  60

Pro Phe Gly Val Asn Ile Met Leu Leu Ser Pro Phe Ala Asp Asp Ile
65                  70                  75                  80

Val Asp Leu Val Ile Glu Glu Gly Val Lys Val Thr Thr Gly Ala
                85                  90                  95

Gly Asn Pro Gly Lys Tyr Ile Glu Arg Phe His Glu Ala Gly Ile Thr
                100                 105                 110

Val Ile Pro Val Val Pro Ser Val Ala Leu Ala Arg Arg Met Glu Lys
            115                 120                 125

Leu Gly Ala Asp Ala Val Ile Ala Glu Gly Met Glu Ala Gly Gly His
        130                 135                 140

Ile Gly Lys Leu Thr Thr Met Thr Leu Val Arg Gln Val Val Asp Ala
145                 150                 155                 160

Val Asn Ile Pro Val Ile Gly Ala Gly Gly Val Ala Asp Gly Arg Gly

```
                    165                 170                 175
Ala Ala Ala Val Phe Met Leu Gly Ala Glu Ala Ile Gln Val Gly Thr
                180                 185                 190
Arg Phe Ala Val Ala Lys Glu Ser Asn Ala His Ala Asn Phe Lys Lys
            195                 200                 205
Lys Ile Leu Lys Ala Lys Asp Ile Asp Thr Val Ile Ser Ala Ser Ile
        210                 215                 220
Val Gly His Pro Val Arg Ala Ile Lys His Lys Leu Ser Ser Ala Tyr
225                 230                 235                 240
Ala Thr Ala Glu Lys Glu Phe Leu Arg Gly Glu Lys Ser Gln Glu Asp
                245                 250                 255
Ile Glu Val Leu Gly Ala Gly Ala Leu Arg Asn Ala Val Val Asp Gly
                260                 265                 270
Asp Val Asp Asn Gly Ser Val Met Ala Gly Gln Ile Ala Gly Phe Val
                275                 280                 285
Thr Lys Glu Glu Thr Cys Glu Glu Ile Leu Lys Asp Leu Tyr Tyr Gly
            290                 295                 300
Ala Ala Lys Val Ile Lys Ala Glu Ala Ala Arg Trp Ala Asp Val Glu
305                 310                 315                 320
Lys
```

<210> SEQ ID NO 5
<211> LENGTH: 972
<212> TYPE: DNA
<213> ORGANISM: Streptococcus pyogenes

<400> SEQUENCE: 5

| | | |
|---|---|---|
| atgaaaacac gtattacaga attacttaat attgattacc ccattttca aggaggaatg | 60 |
| gcttggttg ctgatggtga tttagcaggt gcagtttcta atgctggtgg tttaggcatt | 120 |
| ataggtggtg gcaatgctcc caaagaagtc gttaaagcta atattgatcg tgtcaaagct | 180 |
| attactgata gaccttttgg ggttaatatc atgcttttat ctccttttgc tgatgatatc | 240 |
| gttgatctgg tcattgaaga aggtgttaaa gtagtaacaa caggcgcagg aaatccagga | 300 |
| aagtatatgg aaagactgca ccaggcgggt ataatcgttg ttcctgttgt cccaagcgtt | 360 |
| gcgctagcca acgtatgga aaagcttggg gtagatgctg ttattgctga gggtatggaa | 420 |
| gctggaggac atattggcaa gttaacgact atgtctttag taagacaagt tgttgaagcg | 480 |
| gtttcgattc ctgtcattgc ggcaggtggt atagctgatg tcatggtgc agcagcagca | 540 |
| tttatgttag gagcagaggc tgttcaaatt ggaactcgct tgttgttgc taagaatcc | 600 |
| aatgctcacc aaaattttaa agataaaatc ttagcagcaa aagatattga tacggtgatt | 660 |
| tctgcgcagg ttgtgggcca ccctgtccgt tctattaaaa ataaattgac ctcagcttac | 720 |
| gctaaagcag aaaaagcatt tttaattggt caaaaaacag ctactgatat tgaagaaatg | 780 |
| ggagcaggat cgcttcgaca cgctgttatt gaaggcgatg tagtcaatgg atctgttatg | 840 |
| gctggccaaa ttgcagggct tgtgagaaaa gaagaaagct gtgaaacgat tttaaaagat | 900 |
| atttattatg gtgcagctcg tgttattcaa aatgaagcta agcgctggca atctgtttca | 960 |
| atagaaaagt ag | 972 |

<210> SEQ ID NO 6
<211> LENGTH: 323
<212> TYPE: PRT
<213> ORGANISM: Streptococcus pyogenes

<400> SEQUENCE: 6

| | | | | | | | | | | | | | | |
|---|---|---|---|---|---|---|---|---|---|---|---|---|---|---|
Met Lys Thr Arg Ile Thr Glu Leu Leu Asn Ile Asp Tyr Pro Ile Phe
1               5                   10                  15
Gln Gly Gly Met Ala Trp Val Ala Asp Gly Asp Leu Ala Gly Ala Val
                20                  25                  30
Ser Asn Ala Gly Gly Leu Gly Ile Ile Gly Gly Asn Ala Pro Lys
            35                  40                  45
Glu Val Val Lys Ala Asn Ile Asp Arg Val Lys Ala Ile Thr Asp Arg
50                  55                  60
Pro Phe Gly Val Asn Ile Met Leu Leu Ser Pro Phe Ala Asp Asp Ile
65                      70                  75                  80
Val Asp Leu Val Ile Glu Glu Gly Val Lys Val Val Thr Thr Gly Ala
                85                  90                  95
Gly Asn Pro Gly Lys Tyr Met Glu Arg Leu His Gln Ala Gly Ile Ile
            100                 105                 110
Val Val Pro Val Val Pro Ser Val Ala Leu Ala Lys Arg Met Glu Lys
        115                 120                 125
Leu Gly Val Asp Ala Val Ile Ala Glu Gly Met Glu Ala Gly Gly His
    130                 135                 140
Ile Gly Lys Leu Thr Thr Met Ser Leu Val Arg Gln Val Val Glu Ala
145                 150                 155                 160
Val Ser Ile Pro Val Ile Ala Ala Gly Gly Ile Ala Asp Gly His Gly
                165                 170                 175
Ala Ala Ala Ala Phe Met Leu Gly Ala Glu Ala Val Gln Ile Gly Thr
            180                 185                 190
Arg Phe Val Val Ala Lys Glu Ser Asn Ala His Gln Asn Phe Lys Asp
        195                 200                 205
Lys Ile Leu Ala Ala Lys Asp Ile Asp Thr Val Ile Ser Ala Gln Val
210                 215                 220
Val Gly His Pro Val Arg Ser Ile Lys Asn Lys Leu Thr Ser Ala Tyr
225                 230                 235                 240
Ala Lys Ala Glu Lys Ala Phe Leu Ile Gly Gln Lys Thr Ala Thr Asp
                245                 250                 255
Ile Glu Glu Met Gly Ala Gly Ser Leu Arg His Ala Val Ile Glu Gly
            260                 265                 270
Asp Val Val Asn Gly Ser Val Met Ala Gly Gln Ile Ala Gly Leu Val
        275                 280                 285
Arg Lys Glu Glu Ser Cys Glu Thr Ile Leu Lys Asp Ile Tyr Tyr Gly
    290                 295                 300
Ala Ala Arg Val Ile Gln Asn Glu Ala Lys Arg Trp Gln Ser Val Ser
305                 310                 315                 320
Ile Glu Lys

<210> SEQ ID NO 7
<211> LENGTH: 1068
<212> TYPE: DNA
<213> ORGANISM: Staphylococcus aureus COL

<400> SEQUENCE: 7

```
atgtggaata agaatcgact tactcaaatg ttaagtattg aatatccaat tatacaagca       60
ggtatggcag gaagtacgac accgaaatta gttgcatcag taagtaacag tggtgggtta      120
ggcacaatag gcgcaggtta ctttaatacg cagcaattgg aagatgaaat agattatgta      180
cgccaattaa cgtcaaattc ttttggcgta aatgtctttg taccaagtca acaatcatat      240
```

-continued

```
accagtagtc aaattgaaaa tatgaatgca tggttaaaac cttatcgacg cgcattacat    300
ttagaagagc cggttgtaaa aattaccgaa gaacaacaat ttaagtgtca tattgatacg    360
ataattaaaa agcaagtgcc tgtatgttgt tttactttg gaattccaag cgaacagatt    420
ataagcaggt tgaaagcagc gaatgtcaaa cttataggta cagcaacaag tgttgatgaa    480
gctattgcga atgaaaaagc gggtatggat gctatcgttg ctcaaggtag tgaagcaggt    540
ggacatcgtg gttcattttt aaaacctaaa atcaattac ctatggttgg aacaatatct    600
ttagtgccac aaattgtaga tgtcgtttca attccggtca ttgccgctgg tggaattatg    660
gatggtagag gagttttggc aagtattgtc ttaggtgcag aagggtaca atgggcacc    720 gcatttttaa catcacaaga cagtaatgca tcagaactac tgcgagatgc aattataaat    780
agtaaagaaa cagatacagt cattacaaaa gcgtttagtg aaagcttgc acgcggtatc    840 aacaataggt ttatcgaaga aatgtcccaa tacgaaggcg atatcccaga ttatccaata    900
caaaatgagc taacaagtag cataagaaaa gccgcagcaa acatcggcga caaagagtta    960
atacatatgt ggagtggaca aagcccgcga ctagcaacaa cgcatcccgc caacaccatc    1020
atgtccaata taatcaatca aattaatcaa atcatgcaat ataaataa                 1068
```

<210> SEQ ID NO 8
<211> LENGTH: 355
<212> TYPE: PRT
<213> ORGANISM: Staphylococcus aureus COL

<400> SEQUENCE: 8

```
Met Trp Asn Lys Asn Arg Leu Thr Gln Met Leu Ser Ile Glu Tyr Pro
1               5                   10                  15

Ile Ile Gln Ala Gly Met Ala Gly Ser Thr Thr Pro Lys Leu Val Ala
            20                  25                  30

Ser Val Ser Asn Ser Gly Gly Leu Gly Thr Ile Gly Ala Gly Tyr Phe
        35                  40                  45

Asn Thr Gln Gln Leu Glu Asp Glu Ile Asp Tyr Val Arg Gln Leu Thr
    50                  55                  60

Ser Asn Ser Phe Gly Val Asn Val Phe Val Pro Ser Gln Gln Ser Tyr
65                  70                  75                  80

Thr Ser Ser Gln Ile Glu Asn Met Asn Ala Trp Leu Lys Pro Tyr Arg
                85                  90                  95

Arg Ala Leu His Leu Glu Glu Pro Val Val Lys Ile Thr Glu Glu Gln
            100                 105                 110

Gln Phe Lys Cys His Ile Asp Thr Ile Ile Lys Gln Val Pro Val
        115                 120                 125

Cys Cys Phe Thr Phe Gly Ile Pro Ser Glu Gln Ile Ile Ser Arg Leu
    130                 135                 140

Lys Ala Ala Asn Val Lys Leu Ile Gly Thr Ala Thr Ser Val Asp Glu
145                 150                 155                 160

Ala Ile Ala Asn Glu Lys Ala Gly Met Asp Ala Ile Val Ala Gln Gly
                165                 170                 175

Ser Glu Ala Gly Gly His Arg Gly Ser Phe Leu Lys Pro Lys Asn Gln
            180                 185                 190

Leu Pro Met Val Gly Thr Ile Ser Leu Val Pro Gln Ile Val Asp Val
        195                 200                 205

Val Ser Ile Pro Val Ile Ala Ala Gly Gly Ile Met Asp Gly Arg Gly
    210                 215                 220
```

```
Val Leu Ala Ser Ile Val Leu Gly Ala Glu Gly Val Gln Met Gly Thr
225                 230                 235                 240

Ala Phe Leu Thr Ser Gln Asp Ser Asn Ala Ser Glu Leu Leu Arg Asp
            245                 250                 255

Ala Ile Ile Asn Ser Lys Glu Thr Asp Thr Val Ile Thr Lys Ala Phe
                260                 265                 270

Ser Gly Lys Leu Ala Arg Gly Ile Asn Asn Arg Phe Ile Glu Glu Met
            275                 280                 285

Ser Gln Tyr Glu Gly Asp Ile Pro Asp Tyr Pro Ile Gln Asn Glu Leu
        290                 295                 300

Thr Ser Ser Ile Arg Lys Ala Ala Asn Ile Gly Asp Lys Glu Leu
305                 310                 315                 320

Ile His Met Trp Ser Gly Gln Ser Pro Arg Leu Ala Thr Thr His Pro
                325                 330                 335

Ala Asn Thr Ile Met Ser Asn Ile Ile Asn Gln Ile Asn Gln Ile Met
            340                 345                 350

Gln Tyr Lys
        355

<210> SEQ ID NO 9
<211> LENGTH: 999
<212> TYPE: DNA
<213> ORGANISM: Enterococcus faecalis

<400> SEQUENCE: 9
atgaagtgta cttatcttag aactaaagga cgtataaaat caatgaatca agagttatgt    60
gagttgcttg gaatcaatta tcccattttt caaggcggta tggcttgggt agccgatgct   120
tcattagcaa gtgccgtgtc aaacgctggt ggattaggga ttattgctgg cggcaatgcc   180
ccaaaagaag tcgtaaaaaa agaaattaaa aaagttaaag aattaacgga gcaacccttt   240
ggtgtcaata ttatgttact ttcaccttttt gccgatgaaa ttgtcgattt ggtttgtgaa   300
gaacaggttc ctgtcgtaac gacaggtgca ggcaatccag ccaaatacat ggctcgtttt   360
aaagaacata acattaaagt aatcccagta gttccttcag ttgctttagc aaaaagaatg   420
gaaaaaattg gtgccgatgc tgtcattttt gaaggaatgg aagctggtgg acatattggc   480
aagttaacca ctatgagtgg cttaccgcaa atcgttgacg ctgtgtcaat tcctgtgatt   540
gcagcaggtg ggattggtga tggtcgtggt atggctgcgg cctttatgtt aggtgctgaa   600
gcagtccagt taggcacacg tttttaatt gccaaagaat gcaacgttca tccagattat   660
aaacagaaag tttaaaggc acgtgattta gatgcagtaa ttacctgtca acattttggc   720
catccagtgc gtactttaaa aaataaatta accgctcaat ataatcaatt agaaaagcaa   780
gaactccaaa aagaagtgcc tgatttagaa atgtttgaaa aaattggtca gggcgctttg   840
cgcaaagctg tcgttgacgg ggatatggat tacggttccg tcatggcggg acaaattgcc   900
gggttaataa aaaagaaga aacagcccaa gaaatcattg attcactcat gtctgaatgc   960
aaagcgattg tacataagat gaatcagcgt tggggctaa                          999

<210> SEQ ID NO 10
<211> LENGTH: 332
<212> TYPE: PRT
<213> ORGANISM: Enterococcus faecalis

<400> SEQUENCE: 10

Met Lys Cys Thr Tyr Leu Arg Thr Lys Gly Arg Ile Lys Ser Met Asn
1               5                   10                  15
```

```
Gln Glu Leu Cys Glu Leu Leu Gly Ile Asn Tyr Pro Ile Phe Gln Gly
             20                  25                  30

Gly Met Ala Trp Val Ala Asp Ala Ser Leu Ala Ser Ala Val Ser Asn
         35                  40                  45

Ala Gly Gly Leu Gly Ile Ile Ala Gly Gly Asn Ala Pro Lys Glu Val
     50                  55                  60

Val Lys Lys Glu Ile Lys Lys Val Lys Glu Leu Thr Glu Gln Pro Phe
 65                  70                  75                  80

Gly Val Asn Ile Met Leu Leu Ser Pro Phe Ala Asp Glu Ile Val Asp
                 85                  90                  95

Leu Val Cys Glu Glu Gln Val Pro Val Val Thr Thr Gly Ala Gly Asn
            100                 105                 110

Pro Ala Lys Tyr Met Ala Arg Phe Lys Glu His Asn Ile Lys Val Ile
        115                 120                 125

Pro Val Pro Ser Val Ala Leu Ala Lys Arg Met Glu Lys Ile Gly
    130                 135                 140

Ala Asp Ala Val Ile Phe Glu Gly Met Glu Ala Gly Gly His Ile Gly
145                 150                 155                 160

Lys Leu Thr Thr Met Ser Gly Leu Pro Gln Ile Val Asp Ala Val Ser
                165                 170                 175

Ile Pro Val Ile Ala Ala Gly Gly Ile Gly Asp Gly Arg Gly Met Ala
            180                 185                 190

Ala Ala Phe Met Leu Gly Ala Glu Ala Val Gln Leu Gly Thr Arg Phe
        195                 200                 205

Leu Ile Ala Lys Glu Cys Asn Val His Pro Asp Tyr Lys Gln Lys Val
    210                 215                 220

Leu Lys Ala Arg Asp Leu Asp Ala Val Ile Thr Cys Gln His Phe Gly
225                 230                 235                 240

His Pro Val Arg Thr Leu Lys Asn Lys Leu Thr Ala Gln Tyr Asn Gln
                245                 250                 255

Leu Glu Lys Gln Glu Leu Gln Lys Glu Val Pro Asp Leu Glu Met Phe
            260                 265                 270

Glu Lys Ile Gly Gln Gly Ala Leu Arg Lys Ala Val Val Asp Gly Asp
        275                 280                 285

Met Asp Tyr Gly Ser Val Met Ala Gly Gln Ile Ala Gly Leu Ile Lys
    290                 295                 300

Lys Glu Glu Thr Ala Gln Glu Ile Ile Asp Ser Leu Met Ser Glu Cys
305                 310                 315                 320

Lys Ala Ile Val His Lys Met Asn Gln Arg Trp Gly
                325                 330

<210> SEQ ID NO 11
<211> LENGTH: 933
<212> TYPE: DNA
<213> ORGANISM: Clostridium acetobutylicum

<400> SEQUENCE: 11
atgttaaaaa ctcagttttg tgatataatt ggaataaaat atccaataat tcaaggtgga      60
atggcatggg ttgcagatag ttcacttgca gcgggagttt caaatgcagg aggactcgga     120
ataatagcag cagcaaatgc accagttgag tatgtaagag atgaaataag gaaggcaaaa     180
aaacttacgg ataagccatt cggagttaat ataatgctct aagtgataa tgcagaagaa      240 gttgcaaaaa tggtctgtga ggaaggcgta aaggtagtta ccacaggagc aggaaatcca     300
```

-continued

```
ggtaagtata tagatatgtg aaggaacac gacatcaagg ttattcctgt tgtagcatct    360
gtagcgcttg caaggagaat ggaaagatgt ggagtagatg ctgtagtagc tgaaggttgt    420
gaatcaggag gtcatgtagg agaattaact acaatggcat tagtgccaca agtagtagat    480
gctataaaca ttcctgtaat tgcagctgga ggaataggtg acggaagagg tgttgcagct    540
gcatttgcac ttggagcatc aggagttcag gttggaacaa gattttttaat agcaaaagag    600 tgtactgtac accaaaatta caagaataaa gttttgaaag ctaaggacat cgatacagaa    660
gtaacaggaa gaagtacagg acacccagta agagttctta gaaacaagct tgctagaaaa    720
tataagctaa tggaaaaaga aggagcatcg ccagaggaaa tggaagagtt aggaagagga    780
gcgcttccaa gagcagtaag agaagggat gtggataatg gttctgtaat ggcagggcaa    840
attgcaggac taattaataa agaagaaact tgtgatgaaa tagttgaaag catgtttaaa    900
gaagcagtag aagttataga tagaattaaa tag                                 933
```

<210> SEQ ID NO 12
<211> LENGTH: 310
<212> TYPE: PRT
<213> ORGANISM: Clostridium acetobutylicum

<400> SEQUENCE: 12

```
Met Leu Lys Thr Gln Phe Cys Asp Ile Ile Gly Ile Lys Tyr Pro Ile
  1               5                  10                  15

Ile Gln Gly Gly Met Ala Trp Val Ala Asp Ser Ser Leu Ala Ala Gly
             20                  25                  30

Val Ser Asn Ala Gly Gly Leu Gly Ile Ile Ala Ala Asn Ala Pro
         35                  40                  45

Val Glu Tyr Val Arg Asp Glu Ile Arg Lys Ala Lys Lys Leu Thr Asp
     50                  55                  60

Lys Pro Phe Gly Val Asn Ile Met Leu Leu Ser Asp Asn Ala Glu Glu
 65                  70                  75                  80

Val Ala Lys Met Val Cys Glu Glu Gly Val Lys Val Val Thr Thr Gly
                 85                  90                  95

Ala Gly Asn Pro Gly Lys Tyr Ile Asp Met Trp Lys Glu His Asp Ile
            100                 105                 110

Lys Val Ile Pro Val Val Ala Ser Val Ala Leu Ala Arg Arg Met Glu
        115                 120                 125

Arg Cys Gly Val Asp Ala Val Val Ala Glu Gly Cys Glu Ser Gly Gly
    130                 135                 140

His Val Gly Glu Leu Thr Thr Met Ala Leu Val Pro Gln Val Val Asp
145                 150                 155                 160

Ala Ile Asn Ile Pro Val Ile Ala Ala Gly Ile Gly Asp Gly Arg
                165                 170                 175

Gly Val Ala Ala Ala Phe Ala Leu Gly Ala Ser Gly Val Gln Val Gly
            180                 185                 190

Thr Arg Phe Leu Ile Ala Lys Glu Cys Thr Val His Gln Asn Tyr Lys
        195                 200                 205

Asn Lys Val Leu Lys Ala Lys Asp Ile Asp Thr Glu Val Thr Gly Arg
    210                 215                 220

Ser Thr Gly His Pro Val Arg Val Leu Arg Asn Lys Leu Ala Arg Lys
225                 230                 235                 240

Tyr Lys Leu Met Glu Lys Glu Gly Ala Ser Pro Glu Glu Met Glu Glu
                245                 250                 255

Leu Gly Arg Gly Ala Leu Pro Arg Ala Val Arg Glu Gly Asp Val Asp
```

```
                260                 265                 270
Asn Gly Ser Val Met Ala Gly Gln Ile Ala Gly Leu Ile Asn Lys Glu
            275                 280                 285

Glu Thr Cys Asp Glu Ile Val Glu Ser Met Phe Lys Glu Ala Val Glu
        290                 295                 300

Val Ile Asp Arg Ile Lys
305                 310

<210> SEQ ID NO 13
<211> LENGTH: 930
<212> TYPE: DNA
<213> ORGANISM: Clostridium difficile

<400> SEQUENCE: 13
atgaataaaa tttgcaaaat attaaatata aaatacccag ttatccaagg gggaatggca      60
tgggtagcta ctgcatcatt agcaagtgct gtatctaatg caggaggact tggcataata    120
gcagcaggaa acgcaccaaa agaagctata agaaagaaa ttgttgagtg taaaaaatta    180
acagataaac cttttggagt aaatgtaatg cttatgtcgc catttgttga tgatataatt    240
gatttgatta tagaagaaaa agttcaagtt attactactg gtgctggaaa tcctgcaaag    300
tatatggata gattaaagga agctggaaca aaggttattc ctgtagtacc tacaatagct    360
ttggcacaaa gaatggaaaa gctaggagct acagcagtaa tagcagaagg tactgaaggt    420
ggaggacata taggagaact actactatgg gtcttagttc cacaagttgc tgatgctgta    480
aacataccta taatagctgc tggaggaatt gtagatggta gaggaattgc agcatcattt    540
gcattaggtg ccagtgcagt tcaagtagga actagattta tttgcagtga agagtgttct    600
gtccattcaa actataaaaa cttagtacta aaagcaaaag atagagatgc aattgtaaca    660
ggaagagta ctggtcatcc agtaagaaca ttaaaaaata aactatcaaa gaattttta    720
aagatggaac aaaatggagc tactcctgaa gaattggata aaaaaggtac aggagcttta    780
agatttgcaa cagtagatgg agacatagaa aaaggttcat ttatggcagg tcaaagtgct    840
gctatggtaa aagaaataac accttgtaag gaaattatag aggctatggt aaatcaagca    900
agagagatta tgccagcaat agaactgtaa                                      930

<210> SEQ ID NO 14
<211> LENGTH: 309
<212> TYPE: PRT
<213> ORGANISM: Clostridium difficile

<400> SEQUENCE: 14

Met Asn Lys Ile Cys Lys Ile Leu Asn Ile Lys Tyr Pro Val Ile Gln
1               5                   10                  15

Gly Gly Met Ala Trp Val Ala Thr Ala Ser Leu Ala Ser Ala Val Ser
            20                  25                  30

Asn Ala Gly Gly Leu Gly Ile Ile Ala Ala Gly Asn Ala Pro Lys Glu
        35                  40                  45

Ala Ile Lys Lys Glu Ile Val Glu Cys Lys Lys Leu Thr Asp Lys Pro
    50                  55                  60

Phe Gly Val Asn Val Met Leu Met Ser Pro Phe Val Asp Asp Ile Ile
65                  70                  75                  80

Asp Leu Ile Ile Glu Glu Lys Val Gln Val Ile Thr Thr Gly Ala Gly
                85                  90                  95

Asn Pro Ala Lys Tyr Met Asp Arg Leu Lys Glu Ala Gly Thr Lys Val
            100                 105                 110
```

| | | | | | | | | | | | |
|---|---|---|---|---|---|---|---|---|---|---|---|
|Ile|Pro|Val|Val|Pro|Thr|Ile|Ala|Leu|Ala|Gln|Arg|Met|Glu|Lys|Leu|
| | |115| | | |120| | | |125| |

Ile Pro Val Val Pro Thr Ile Ala Leu Ala Gln Arg Met Glu Lys Leu
            115                 120                 125
Gly Ala Thr Ala Val Ile Ala Glu Gly Thr Glu Gly Gly His Ile
130                 135                 140
Gly Glu Leu Thr Thr Met Val Leu Val Pro Gln Val Ala Asp Ala Val
145                 150                 155                 160
Asn Ile Pro Val Ile Ala Ala Gly Ile Val Asp Gly Arg Gly Ile
            165                 170                 175
Ala Ala Ser Phe Ala Leu Gly Ala Ser Ala Val Gln Val Gly Thr Arg
            180                 185                 190
Phe Ile Cys Ser Glu Glu Cys Ser Val His Ser Asn Tyr Lys Asn Leu
            195                 200                 205
Val Leu Lys Ala Lys Asp Arg Asp Ala Ile Val Thr Gly Arg Ser Thr
    210                 215                 220
Gly His Pro Val Arg Thr Leu Lys Asn Lys Leu Ser Lys Glu Phe Leu
225                 230                 235                 240
Lys Met Glu Gln Asn Gly Ala Thr Pro Glu Glu Leu Asp Lys Lys Gly
                245                 250                 255
Thr Gly Ala Leu Arg Phe Ala Thr Val Asp Gly Asp Ile Glu Lys Gly
            260                 265                 270
Ser Phe Met Ala Gly Gln Ser Ala Ala Met Val Lys Glu Ile Thr Pro
        275                 280                 285
Cys Lys Glu Ile Ile Glu Ala Met Val Asn Gln Ala Arg Glu Ile Met
    290                 295                 300
Pro Ala Ile Glu Leu
305

<210> SEQ ID NO 15
<211> LENGTH: 873
<212> TYPE: DNA
<213> ORGANISM: Porphyromonas gingivalis W83

<400> SEQUENCE: 15

```
atgaatagaa tttgcgaatt attgggtatc gaacatccga tcatatcggg aggcatggtg    60
tggtgcagcg gttggaaact ggcttctgct gtgagcaact gcggtggttt gggacttatt   120
ggtgccggat ccatgcatcc ggacaatctg agcatcaca tccgttcgtg taaagctgct   180
acagacaagc ctttcggtgt gaacgtgcct cttctctatc cggagatgga caaaatcatg   240
gagattatca tgagggaaca tgtgcccgta gtggtaacgt cagccggtag tccaaaggtg   300
tggacagcca agttgaaagc tgccggtagc aaggtgatac atgtagtgag cagtgccaca   360
ttcgctcgca aatcagaggc agccggtgta gacgccatcg tggccgaagg gttcgaagcc   420
ggcggacata atggacgaga ggagactacg accctctgtt tgatacctga gtagtggat    480
gctgtgaaca ttcctgtggt tgctgccgga gggattgctt ccggccgtgc agttgccgct   540
gctttggctt tgggtgccga tgccgtacaa gtgggaccc gttttgctct gagtgaggaa    600
agttcggcgc atgaagactt taaggcacat tgccgccggt cggtggaggg agatacgatg   660
ctttcgctca aggctgtatc gcctacgcga ctgctgaaga acaaattcta tcaggatgta   720
ttcgctgccg agcagcgcgg tgcttccgtg aagagctgc gcgagctgct cggtcgtggt    780
cgtgccaagc aaggtatttt cgaaggcgac ctgcacgagg gcgaattgga gataggccag   840
gcagtatcgc agataagtca tgcggagacg gtg                                873
```

<210> SEQ ID NO 16
<211> LENGTH: 313
<212> TYPE: PRT
<213> ORGANISM: Porphyromonas gingivalis W83

<400> SEQUENCE: 16

```
Met Asn Arg Ile Cys Glu Leu Leu Gly Ile Glu His Pro Ile Ile Ser
1               5                   10                  15
Gly Gly Met Val Trp Cys Ser Gly Trp Lys Leu Ala Ser Ala Val Ser
            20                  25                  30
Asn Cys Gly Gly Leu Gly Leu Ile Gly Ala Gly Ser Met His Pro Asp
        35                  40                  45
Asn Leu Glu His His Ile Arg Ser Cys Lys Ala Ala Thr Asp Lys Pro
    50                  55                  60
Phe Gly Val Asn Val Pro Leu Leu Tyr Pro Glu Met Asp Lys Ile Met
65                  70                  75                  80
Glu Ile Ile Met Arg Glu His Val Pro Val Val Thr Ser Ala Gly
                85                  90                  95
Ser Pro Lys Val Trp Thr Ala Lys Leu Lys Ala Ala Gly Ser Lys Val
            100                 105                 110
Ile His Val Val Ser Ser Ala Thr Phe Ala Arg Lys Ser Glu Ala Ala
        115                 120                 125
Gly Val Asp Ala Ile Val Ala Glu Gly Phe Glu Ala Gly Gly His Asn
    130                 135                 140
Gly Arg Glu Glu Thr Thr Thr Leu Cys Leu Ile Pro Glu Val Val Asp
145                 150                 155                 160
Ala Val Asn Ile Pro Val Val Ala Ala Gly Gly Ile Ala Ser Gly Arg
                165                 170                 175
Ala Val Ala Ala Ala Leu Ala Leu Gly Ala Asp Ala Val Gln Val Gly
            180                 185                 190
Thr Arg Phe Ala Leu Ser Glu Glu Ser Ser Ala His Glu Asp Phe Lys
        195                 200                 205
Ala His Cys Arg Arg Ser Val Gly Asp Thr Met Leu Ser Leu Lys
    210                 215                 220
Ala Val Ser Pro Thr Arg Leu Leu Lys Asn Lys Phe Tyr Gln Asp Val
225                 230                 235                 240
Phe Ala Ala Glu Gln Arg Gly Ala Ser Val Glu Glu Leu Arg Glu Leu
                245                 250                 255
Leu Gly Arg Gly Arg Ala Lys Gln Gly Ile Phe Glu Gly Asp Leu His
            260                 265                 270
Glu Gly Glu Leu Glu Ile Gly Gln Ala Val Ser Gln Ile Ser His Ala
        275                 280                 285
Glu Thr Val Ala Glu Ile Met Val Asp Leu Val Asp Gly Tyr Lys Arg
    290                 295                 300
Ser Leu Ala Gly Met Pro Thr Glu Ile
305                 310
```

<210> SEQ ID NO 17
<211> LENGTH: 966
<212> TYPE: DNA
<213> ORGANISM: Caulobacter crescentus

<400> SEQUENCE: 17

```
atgggcctgc gcacgccgct gtgtgatctg ctggatatcg agcatccgat cctgctggcc    60
ggcatgggcg gggtctccta cgccccgctg gccgccgccg tctccaacgc cggcggctat   120
```

-continued

```
ggcgtcctgg gcatggccgg caccagcccg gacttcatcc gcgcccagat gcgcgaggtc    180
aaaagcctga ccgacaagcc gttcggggtg gacctgctgg ccgccacgcc ggatgcgctg    240
accgcgtccg tcgaggtcat catcgaggag ggcgcctcct catttgtcgc gggcctgggc    300
gtgcccctgc cgatcatcga acgactcaag gccgccggcc tgaaggtcat ggtcgtctgc    360
ggagccgtga agcacgcggt caaggccgag caggcgggct cgacgcggt gatctgccaa     420 ggcggcgagg gcggtggtca cacgggtctc gtcggcaccc tgccgctggt ggcccaggcc    480
gtggaggcgt gaagatcccc ggtggtcgcc gccggcggcc tgcatgacgg ccgcgggctg    540
gcggcggccc tggctctggg cgcgcagggc gtctggatgg gcacgcggtt catcgcctcg    600
cacgaggccc atgcgggcga tctctaccgc caggcggtgg tcgaggccgc cgacgaggac    660
acggtgcgca cgcgctgcta ctcgggcaag ccgatgcggg tgaagaagaa ccctatgtc    720 gacgactggg aagcgcgtcc cggcgacatc cagccttcc cgcagcaggc catggtctcg     780
atccgcaatg cgccatggg cggcatcggc ggccagatca agggcctgga cgcggccaag    840
tcctgcttcg ccatgggcca gagccgcggc ggcgtgcgcg agatcttgcc ggccggcgag    900
atcgtcaagc ggctgatggc cgaggccgag acggcgctgg ccaaggcctc ggccttcagg   960
acctga                                                             966
```

<210> SEQ ID NO 18
<211> LENGTH: 321
<212> TYPE: PRT
<213> ORGANISM: Caulobacter crescentus
<400> SEQUENCE: 18

```
Met Gly Leu Arg Thr Pro Leu Cys Asp Leu Leu Asp Ile Glu His Pro
1               5                   10                  15

Ile Leu Leu Ala Gly Met Gly Gly Val Ser Tyr Ala Pro Leu Ala Ala
            20                  25                  30

Ala Val Ser Asn Ala Gly Gly Tyr Gly Val Leu Gly Met Ala Gly Thr
        35                  40                  45

Ser Pro Asp Phe Ile Arg Ala Gln Met Arg Glu Val Lys Ser Leu Thr
    50                  55                  60

Asp Lys Pro Phe Gly Val Asp Leu Leu Ala Ala Thr Pro Asp Ala Leu
65                  70                  75                  80

Thr Ala Ser Val Glu Val Ile Ile Glu Glu Gly Ala Ser Ser Phe Val
                85                  90                  95

Ala Gly Leu Gly Val Pro Leu Pro Ile Ile Glu Arg Leu Lys Ala Ala
            100                 105                 110

Gly Leu Lys Val Met Val Cys Gly Ala Val Lys His Ala Val Lys
        115                 120                 125

Ala Glu Gln Ala Gly Cys Asp Ala Val Ile Cys Gln Gly Gly Glu Gly
    130                 135                 140

Gly Gly His Thr Gly Leu Val Gly Thr Leu Pro Leu Val Ala Gln Ala
145                 150                 155                 160

Val Glu Ala Val Lys Ile Pro Val Val Ala Gly Gly Leu His Asp
                165                 170                 175

Gly Arg Gly Leu Ala Ala Ala Leu Ala Leu Gly Ala Gln Gly Val Trp
            180                 185                 190

Met Gly Thr Arg Phe Ile Ala Ser His Glu Ala His Ala Gly Asp Leu
        195                 200                 205

Tyr Arg Gln Ala Val Val Glu Ala Ala Asp Glu Asp Thr Val Arg Thr
    210                 215                 220
```

```
Arg Cys Tyr Ser Gly Lys Pro Met Arg Val Lys Lys Asn Pro Tyr Val
225                 230                 235                 240

Asp Asp Trp Glu Ala Arg Pro Gly Asp Ile Gln Pro Phe Pro Gln Gln
            245                 250                 255

Ala Met Val Ser Ile Arg Asn Gly Ala Met Gly Gly Ile Gly Gly Gln
        260                 265                 270

Ile Glu Gly Leu Asp Ala Ala Lys Ser Cys Phe Ala Met Gly Gln Ser
    275                 280                 285

Ala Gly Gly Val Arg Glu Ile Leu Pro Ala Gly Glu Ile Val Lys Arg
    290                 295                 300

Leu Met Ala Glu Ala Glu Thr Ala Leu Ala Lys Ala Ser Ala Phe Arg
305                 310                 315                 320

Thr
```

<210> SEQ ID NO 19
<211> LENGTH: 987
<212> TYPE: DNA
<213> ORGANISM: Pseudomonas aeruginosa

<400> SEQUENCE: 19

```
atgggcgtgt tcaggacccg tttcaccgag accttcggcg tcgaacaccc gatcatgcag      60
ggcggcatgc agtgggtcgg ccgtgccgag atggctgcgg cggtggccaa cgccggtggc     120
ctggcgacgt tgtcggcgtt gacccagccg agcccgagg cactggctgc ggagattgcc      180
cgctgccgcg agctgaccga tcggccgttc ggggtcaacc tgaccttgct gccgacgcag     240
aagccggtgc cctatgccga atatcgcgca gccatcatcg aggcgggaat ccgcgtcgtc     300
gaaaccgccg gcaacgaccc cggcgagcac atcgccgaat ccgtcgaca cggcgtcaag      360
gtgatccaca gtgcaccgc cgtgcgccat gcgctcaagg ccgagcgact gggcgtggac      420
gccgtctcca tcgacggctt cgagtgtgcc ggccacccgg gcgaggacga catccccggc     480
ctggtgttgc tgccggccgc ggccaaccgg ctacgcgtgc cgatcatcgc ctccggcggt     540
ttcgccgatg gacgtggcct ggtcgcggcg ctggcgctgg gtgccgacgc gatcaacatg     600
ggcacgcgct tcctggccac tcgcgaatgt ccgatacacc ctgcggtgaa ggcggcgatc     660
cgtgcggccg acgagcgttc caccgacctg atcatgcgtt ccctgcgcaa taccgcgcgg     720
gtggcgcgca acgcgatcag ccaggaagta ctggcgatcg aggcacgcgg cggcgccggc     780
tacgccgata tcgccgcgct ggtcagcggc agcgcggtc gccaggtgta ccagcagggc     840
gataccgacc tggggatctg gtcggccggc atggtccagg gcctgatcga cgacgaaccg     900
gcctgcgccg agttgctcag ggacatcgtc gagcaggcgc gccaactggt gcgtcaacgc     960
ctggagggca tgctcgccgg ggtctga                                         987
```

<210> SEQ ID NO 20
<211> LENGTH: 328
<212> TYPE: PRT
<213> ORGANISM: Pseudomonas aeruginosa

<400> SEQUENCE: 20

```
Met Gly Val Phe Arg Thr Arg Phe Thr Glu Thr Phe Gly Val Glu His
1               5                   10                  15

Pro Ile Met Gln Gly Gly Met Gln Trp Val Gly Arg Ala Glu Met Ala
            20                  25                  30

Ala Ala Val Ala Asn Ala Gly Gly Leu Ala Thr Leu Ser Ala Leu Thr
        35                  40                  45
```

```
Gln Pro Ser Pro Glu Ala Leu Ala Ala Glu Ile Ala Arg Cys Arg Glu
     50                  55                  60

Leu Thr Asp Arg Pro Phe Gly Val Asn Leu Thr Leu Leu Pro Thr Gln
 65                  70                  75                  80

Lys Pro Val Pro Tyr Ala Glu Tyr Arg Ala Ala Ile Ile Glu Ala Gly
                 85                  90                  95

Ile Arg Val Val Glu Thr Ala Gly Asn Asp Pro Gly Glu His Ile Ala
                100                 105                 110

Glu Phe Arg Arg His Gly Val Lys Val Ile His Lys Cys Thr Ala Val
            115                 120                 125

Arg His Ala Leu Lys Ala Glu Arg Leu Gly Val Asp Ala Val Ser Ile
        130                 135                 140

Asp Gly Phe Glu Cys Ala Gly His Pro Gly Glu Asp Ile Pro Gly
145                 150                 155                 160

Leu Val Leu Pro Ala Ala Ala Asn Arg Leu Arg Val Pro Ile Ile
                165                 170                 175

Ala Ser Gly Gly Phe Ala Asp Gly Arg Gly Leu Val Ala Ala Leu Ala
            180                 185                 190

Leu Gly Ala Asp Ala Ile Asn Met Gly Thr Arg Phe Leu Ala Thr Arg
        195                 200                 205

Glu Cys Pro Ile His Pro Ala Val Lys Ala Ala Ile Arg Ala Ala Asp
    210                 215                 220

Glu Arg Ser Thr Asp Leu Ile Met Arg Ser Leu Arg Asn Thr Ala Arg
225                 230                 235                 240

Val Ala Arg Asn Ala Ile Ser Gln Glu Val Leu Ala Ile Glu Ala Arg
                245                 250                 255

Gly Gly Ala Gly Tyr Ala Asp Ile Ala Ala Leu Val Ser Gly Gln Arg
            260                 265                 270

Gly Arg Gln Val Tyr Gln Gln Gly Asp Thr Asp Leu Gly Ile Trp Ser
        275                 280                 285

Ala Gly Met Val Gln Gly Leu Ile Asp Asp Glu Pro Ala Cys Ala Glu
    290                 295                 300

Leu Leu Arg Asp Ile Val Glu Gln Ala Arg Gln Leu Val Arg Gln Arg
305                 310                 315                 320

Leu Glu Gly Met Leu Ala Gly Val
                325

<210> SEQ ID NO 21
<211> LENGTH: 1044
<212> TYPE: DNA
<213> ORGANISM: Bacillus subtilis

<400> SEQUENCE: 21
atgaatgaat ttatgaaaaa gttttcttta acaaaaccga ttattcaagc tccaatggct      60
ggcggtatta caaagccccg acttgcatct gcagtttcga atcaaggtgc tcttggcagc     120
ttagcatcgg ggtatcttac gccagacctc ctagaacaac aaataaaaga aatatttgag     180
ctgacagacg ctccttttca aattaatgtg tttgttccgc taggtctaga gatgccacca     240
aaagatcaga ttaaaagtg gaaagaaaac ataccgttag ctaatcaagt aaatcaattc     300
acatctgtac aagaagagtg ggatgacttc tatcaaaaaa ttgatctaat tttaaaatac     360
aaggttaagg cttgctcatt cacttttgat ctgccgcctg aagacgcagt aaaggagcta     420
aaaaccgctg gatgctgttt aataggaacc gcttcaacag tagaagaagc attgttaatg     480
```

-continued

```
gaagaacggg gaatggatat agtagtcctt caaggaagtg aagccggtgg acatcgcgga    540
gcattcttac cttccaaagg tgaatctgcc gtaggtttaa tggctctgat ccacaagca    600 gcagatgcac tgagcgtacc tgtcatagct gctgggggaa tgatagacca cagaggagta    660
aaagcagctt taaccctcgg agcccaaggc gttcaaatcg gttctgcctt tttaatttgt    720
cacgagagta acgcacatcc agtgcataaa cagaaaatac tagaagcaaa cgaagcagat    780
acaaagctta cgacattatt ttcaggtaaa gaggccagag gaatcgtaaa taaatggatg    840
gaagaaaatg aacagtttga gacacaaacc cttccgtacc cttatcaaaa tacactaacg    900
aaggcaatga gacagaaggc ttcacttcaa ataaccatg atcagatgtc tttatgggca    960
ggtcaaggga tacggtcatt gactgaggaa atttcggtta agcagctttt aaatcagctt    1020
tgccaagagg atataaaaat atag                                          1044
```

<210> SEQ ID NO 22
<211> LENGTH: 347
<212> TYPE: PRT
<213> ORGANISM: Bacillus subtilis

<400> SEQUENCE: 22

```
Met Asn Glu Phe Met Lys Lys Phe Ser Leu Thr Lys Pro Ile Ile Gln
1               5                   10                  15

Ala Pro Met Ala Gly Gly Ile Thr Lys Pro Arg Leu Ala Ser Ala Val
                20                  25                  30

Ser Asn Gln Gly Ala Leu Gly Ser Leu Ala Ser Gly Tyr Leu Thr Pro
            35                  40                  45

Asp Leu Leu Glu Gln Gln Ile Lys Glu Ile Phe Glu Leu Thr Asp Ala
        50                  55                  60

Pro Phe Gln Ile Asn Val Phe Val Pro Leu Gly Leu Glu Met Pro Pro
65                  70                  75                  80

Lys Asp Gln Ile Lys Lys Trp Lys Glu Asn Ile Pro Leu Ala Asn Gln
                85                  90                  95

Val Asn Gln Phe Thr Ser Val Gln Glu Glu Trp Asp Asp Phe Tyr Gln
            100                 105                 110

Lys Ile Asp Leu Ile Leu Lys Tyr Lys Val Lys Ala Cys Ser Phe Thr
        115                 120                 125

Phe Asp Leu Pro Pro Glu Asp Ala Val Lys Glu Leu Lys Thr Ala Gly
    130                 135                 140

Cys Cys Leu Ile Gly Thr Ala Ser Thr Val Glu Glu Ala Leu Leu Met
145                 150                 155                 160

Glu Glu Arg Gly Met Asp Ile Val Val Leu Gln Gly Ser Glu Ala Gly
                165                 170                 175

Gly His Arg Gly Ala Phe Leu Pro Ser Lys Gly Glu Ser Ala Val Gly
            180                 185                 190

Leu Met Ala Leu Ile Pro Gln Ala Ala Asp Ala Leu Ser Val Pro Val
        195                 200                 205

Ile Ala Ala Gly Gly Met Ile Asp His Arg Gly Val Lys Ala Ala Leu
    210                 215                 220

Thr Leu Gly Ala Gln Gly Val Gln Ile Gly Ser Ala Phe Leu Ile Cys
225                 230                 235                 240

His Glu Ser Asn Ala His Pro Val His Lys Gln Lys Ile Leu Glu Ala
                245                 250                 255

Asn Glu Ala Asp Thr Lys Leu Thr Leu Phe Ser Gly Lys Glu Ala
            260                 265                 270
```

```
Arg Gly Ile Val Asn Lys Trp Met Glu Glu Asn Glu Gln Phe Glu Thr
            275                 280                 285

Gln Thr Leu Pro Tyr Pro Tyr Gln Asn Thr Leu Thr Lys Ala Met Arg
        290                 295                 300

Gln Lys Ala Ser Leu Gln Asn Asn His Asp Gln Met Ser Leu Trp Ala
305                 310                 315                 320

Gly Gln Gly Ile Arg Ser Leu Thr Glu Glu Ile Ser Val Lys Gln Leu
                325                 330                 335

Leu Asn Gln Leu Cys Gln Glu Asp Ile Lys Ile
            340                 345

<210> SEQ ID NO 23
<211> LENGTH: 1128
<212> TYPE: DNA
<213> ORGANISM: Mycobacterium tuberculosis rv1533

<400> SEQUENCE: 23
atgcggacca gagtcgccga gctgctcggt gctgagtttc caatatgcgc gttcagccac     60
tgccgggatg tggtggcggc ggtgtccaat gcgggcgggt tcgggatcct cggtgccgtc    120
gcacatagcc ccaaacggct ggagagcgag ctgacctgga tcgaggagca cacgggtggc    180
aagccgtacg gagtcgacgt gctgctgccg cccaaataca tcggcgccga gcaaggcggt    240
atcgatgccc agcaggcccg ggagctcata cccgaaggc atcgcacctt cgtcgacgac    300
ttgctggttc gctatggcat ccccgcggtc accgaccggc agcgttcgtc ctcggccggt    360
gggctgcaca tctcgcccaa gggttatcag ccgttgctgg atgtggcctt cgcccatgac    420
atccggttga tcgccagcgc gctcgggccg ccgccaccgg atctcgtgga gcgcgcccac    480
aaccatgacg tgctggttgc cgccctagcc ggcacggcgc agcacgcgcg gcgacacgcg    540
gctgcgggtg ttgacctgat cgtcgcgcag ggcaccgagg ccggaggcca caccggcgag    600
gtggcgacca tggttctggt tcccgaagtc gtcgatgcgg tgtcgccaac gccggtgctg    660
gccgcgggcg ggatcgcccg tggccgccaa atcgctgcgg cgttggccct ggggcggaa    720 ggcgtctggt gcgggtcggt ctggttgacc accgaagaag ccgaaacgcc cccggtggtc    780
aaggacaagt ttctggccgc aacatcctcg gacacggtgc ggtcccggtc gctaaccggc    840
aagccggcgc gcatgctgcg cacggcctgg accgacgaat gggatcggcc tgacagcccc    900
gacccgcttg gcatgccgct gcagagcgcg ctggtcagcg acccgcagtt gcgcatcaac    960
caggccgccg ccagcccggg gccaaggct cgtgagctgg cgacctactt cgtcggacag   1020
gtcgtcggct cactcgaccg ggtgcggtcg gcccgctcgg tggtgcttga catggtcgag   1080
gagttcatcg acaccgtcgg gcaactgcag gggttggtgc aaaggtga                1128

<210> SEQ ID NO 24
<211> LENGTH: 375
<212> TYPE: PRT
<213> ORGANISM: Mycobacterium tuberculosis rv1533

<400> SEQUENCE: 24

Met Arg Thr Arg Val Ala Glu Leu Leu Gly Ala Glu Phe Pro Ile Cys
1               5                   10                  15

Ala Phe Ser His Cys Arg Asp Val Val Ala Val Ser Asn Ala Gly
            20                  25                  30

Gly Phe Gly Ile Leu Gly Ala Val Ala His Ser Pro Lys Arg Leu Glu
        35                  40                  45

Ser Glu Leu Thr Trp Ile Glu Glu His Thr Gly Gly Lys Pro Tyr Gly
```

```
              50                  55                  60
Val Asp Val Leu Leu Pro Pro Lys Tyr Ile Gly Ala Glu Gln Gly Gly
 65                  70                  75                  80

Ile Asp Ala Gln Gln Ala Arg Glu Leu Ile Pro Glu Gly His Arg Thr
                 85                  90                  95

Phe Val Asp Asp Leu Leu Val Arg Tyr Gly Ile Pro Ala Val Thr Asp
            100                 105                 110

Arg Gln Arg Ser Ser Ser Ala Gly Gly Leu His Ile Ser Pro Lys Gly
            115                 120                 125

Tyr Gln Pro Leu Leu Asp Val Ala Phe Ala His Asp Ile Arg Leu Ile
            130                 135                 140

Ala Ser Ala Leu Gly Pro Pro Pro Asp Leu Val Glu Arg Ala His
145                 150                 155                 160

Asn His Asp Val Leu Val Ala Ala Leu Ala Gly Thr Ala Gln His Ala
                165                 170                 175

Arg Arg His Ala Ala Ala Gly Val Asp Leu Ile Val Ala Gln Gly Thr
            180                 185                 190

Glu Ala Gly Gly His Thr Gly Glu Val Ala Thr Met Val Leu Val Pro
            195                 200                 205

Glu Val Val Asp Ala Val Ser Pro Thr Pro Val Leu Ala Ala Gly Gly
210                 215                 220

Ile Ala Arg Gly Arg Gln Ile Ala Ala Leu Ala Leu Gly Ala Glu
225                 230                 235                 240

Gly Val Trp Cys Gly Ser Val Trp Leu Thr Thr Glu Ala Glu Thr
                245                 250                 255

Pro Pro Val Val Lys Asp Lys Phe Leu Ala Ala Thr Ser Ser Asp Thr
            260                 265                 270

Val Arg Ser Arg Ser Leu Thr Gly Lys Pro Ala Arg Met Leu Arg Thr
            275                 280                 285

Ala Trp Thr Asp Glu Trp Asp Arg Pro Asp Ser Pro Asp Pro Leu Gly
            290                 295                 300

Met Pro Leu Gln Ser Ala Leu Val Ser Asp Pro Gln Leu Arg Ile Asn
305                 310                 315                 320

Gln Ala Ala Gly Gln Pro Gly Ala Lys Ala Arg Glu Leu Ala Thr Tyr
                325                 330                 335

Phe Val Gly Gln Val Val Gly Ser Leu Asp Arg Val Arg Ser Ala Arg
            340                 345                 350

Ser Val Val Leu Asp Met Val Glu Glu Phe Ile Asp Thr Val Gly Gln
            355                 360                 365

Leu Gln Gly Leu Val Gln Arg
            370                 375

<210> SEQ ID NO 25
<211> LENGTH: 1035
<212> TYPE: DNA
<213> ORGANISM: Mycobacterium tuberculosis rv2781c

<400> SEQUENCE: 25
atggtgttgg gcttctggga catcgcggtg ccgatcgtcg gcgccccgat ggccggcggc      60
ccgagcaccc cggcgttggc cgcggcggtg tccaacgctg gcgggcttgg tttcgtcgcc     120
ggcggctatc tgagcgcgga ccggctcgcc gacgatatcg ccgctgcgcg cgccgccact     180
accggtccta tcggagccaa tctgtttgtg ccccaaccca gcgtcgccga ctgggcgcag     240
ctggagtatt acgcggacga gctcgaagag gtcgccgagt actaccacac cgaggtgggc     300
```

```
cagcccgtct atggtgacga cgacgactgg gtgcgcaaac tcgaggtggt agccgatgtt    360
cgtccggagg tggtgtcgtt caccttcggc gcgccgccgc cggatgtcgt gcagcggttg    420
agcgcgctgg gactgttggt ctcgatcacc gtgacgtcgg tctacgaggc cggtgtggcc    480
attgccgcgg gcgcggacag cctggtggtc cagggcccgg ctgccggcgg caccgcgga    540
acgttcgcgc cggacatgga acccggtacg gagtcgctgc accaactcct cgatcggatt    600
ggcagcgccc atgatgtgcc gctggttgca gccggtggcc tgggcacggc tgaggacgtg    660
gccgccgtgc tgcgccgcgg agcgatcgcc gcgcaggttg gtaccgcatt gctgctggcc    720
gacgaagccg gtaccaatgc cgcacaccgt gccgcgctga gaatccaga gttcgatgcc     780
accctggtca ctcgggcgtt ctcgggtagg tatgcgcgcg gtctggccaa caacttcact    840
cgcctgctcg accacgtggc gccgctgggt tatccggagg tccaccagat gacgaagccg    900
atacgggcgg cggcggtgca ggcggacgac ccgcacggaa caaacctttg gcgggatcg     960
gcgcaccgga agaccggcc gggacccgcg gccgacatca tcgcttccct tactcccgac    1020
gtgtgctcgg cgtaa                                                    1035
```

<210> SEQ ID NO 26
<211> LENGTH: 344
<212> TYPE: PRT
<213> ORGANISM: Mycobacterium tuberculosis rv2781c

<400> SEQUENCE: 26

```
Met Val Leu Gly Phe Trp Asp Ile Ala Val Pro Ile Val Gly Ala Pro
1               5                   10                  15
Met Ala Gly Gly Pro Ser Thr Pro Ala Leu Ala Ala Ala Val Ser Asn
                20                  25                  30
Ala Gly Gly Leu Gly Phe Val Ala Gly Tyr Leu Ser Ala Asp Arg
            35                  40                  45
Leu Ala Asp Asp Ile Ala Ala Ala Arg Ala Ala Thr Thr Gly Pro Ile
    50                  55                  60
Gly Ala Asn Leu Phe Val Pro Gln Pro Ser Val Ala Asp Trp Ala Gln
65                  70                  75                  80
Leu Glu Tyr Tyr Ala Asp Glu Leu Glu Glu Val Ala Glu Tyr Tyr His
                85                  90                  95
Thr Glu Val Gly Gln Pro Val Tyr Gly Asp Asp Asp Trp Val Arg
                100                 105                 110
Lys Leu Glu Val Val Ala Asp Val Arg Pro Glu Val Val Ser Phe Thr
            115                 120                 125
Phe Gly Ala Pro Pro Pro Asp Val Val Gln Arg Leu Ser Ala Leu Gly
        130                 135                 140
Leu Leu Val Ser Ile Thr Val Thr Ser Val Tyr Glu Ala Gly Val Ala
145                 150                 155                 160
Ile Ala Ala Gly Ala Asp Ser Leu Val Val Gln Gly Pro Ala Ala Gly
                165                 170                 175
Gly His Arg Gly Thr Phe Ala Pro Asp Met Glu Pro Gly Thr Glu Ser
            180                 185                 190
Leu His Gln Leu Leu Asp Arg Ile Gly Ser Ala His Asp Val Pro Leu
        195                 200                 205
Val Ala Ala Gly Gly Leu Gly Thr Ala Glu Asp Val Ala Ala Val Leu
    210                 215                 220
Arg Arg Gly Ala Ile Ala Ala Gln Val Gly Thr Ala Leu Leu Leu Ala
225                 230                 235                 240
```

-continued

```
Asp Glu Ala Gly Thr Asn Ala Ala His Arg Ala Ala Leu Lys Asn Pro
            245                 250                 255

Glu Phe Asp Ala Thr Leu Val Thr Arg Ala Phe Ser Gly Arg Tyr Ala
        260                 265                 270

Arg Gly Leu Ala Asn Asn Phe Thr Arg Leu Leu Asp His Val Ala Pro
    275                 280                 285

Leu Gly Tyr Pro Glu Val His Gln Met Thr Lys Pro Ile Arg Ala Ala
    290                 295                 300

Ala Val Gln Ala Asp Asp Pro His Gly Thr Asn Leu Trp Ala Gly Ser
305                 310                 315                 320

Ala His Arg Lys Thr Arg Pro Gly Pro Ala Ala Asp Ile Ile Ala Ser
            325                 330                 335

Leu Thr Pro Asp Val Cys Ser Ala
        340
```

<210> SEQ ID NO 27
<211> LENGTH: 1068
<212> TYPE: DNA
<213> ORGANISM: Mycobacterium tuberculosis rv3553

<400> SEQUENCE: 27

```
atgaggctgc gtacgccgct gaccgagctc atcggcatcg agcacccggt ggtgcagacc      60
gggatgggct gggtggccgg tgcccggctg gtgtcggcca ccgccaacgc gggcgggctg     120
ggcatcttgg cctcggccac catgacgctg gacgagctgg cggcggcgat cacaaaggtc     180
aaggccgtca ccgacaagcc attcggggtg aacatccgcg ccgacgcagc cgacgcgggc     240
gaccgcgtcg agttgatgat ccgcgagggg gtgcgggtgg cctcgttcgc gttggcaccc     300
aaacagcagc tgatcgcccg gctcaaagaa gccggcgcgg tggtcatacc gtcgatcggc     360
gcggccaaac atgcgcgcaa ggtggcggcc tggggcgccg acgcgatgat cgtgcagggc     420
ggcgagggcg gcggccacac cgggccggtc gccaccacgc tgctgttgcc gtcggtgctg     480
gacgccgtgg cgggcaccgg catcccggtg atcgccgccg gcggcttctt cgacgggcgc     540
gggctagccg cggcgttgtg ctacggcgcc gccggggtgg ccatgggcac ccggtttctg     600
ctcacctcgg attccaccgt gcccgacgcg gtcaaacggc gttacctgca ggccggcttg     660
gacggcaccg tggtcaccac ccgcgtcgac gggatgccgc accgggtgct gcgcaccgag     720
ctggtcgaga agctggaaag cggctcgcgg gcacgaggtt tcgcggccgc gctgcgcaat     780
gccggcaagt ttagacggat gtcgcagatg acctggcggt cgatgatccg agacggcctg     840
accatgcgcc acggcaagga attgacctgg tcacaggtgc tgatggcggc aaacaccccg     900
atgctgctca aagccggcct ggtcgacggc aacaccgagg ccggggtgct ggcatcgggc     960
caggtagcgg gcattcttga cgacctaccg tcgtgcaaag agctgatcga gtcgatcgtg    1020
cttgacgcca tcacacattt acaaaccgca tctgcgctgg tggagtga                 1068
```

<210> SEQ ID NO 28
<211> LENGTH: 355
<212> TYPE: PRT
<213> ORGANISM: Mycobacterium tuberculosis rv3553

<400> SEQUENCE: 28

```
Met Arg Leu Arg Thr Pro Leu Thr Glu Leu Ile Gly Ile Glu His Pro
1               5                   10                  15

Val Val Gln Thr Gly Met Gly Trp Val Ala Gly Ala Arg Leu Val Ser
            20                  25                  30
```

| | | | | | | | | | | | |
|---|---|---|---|---|---|---|---|---|---|---|---|
|Ala|Thr|Ala|Asn|Ala|Gly|Gly|Leu|Gly|Ile|Leu|Ala|Ser|Ala|Thr|Met|
| |35| | | |40| | | |45| | |

Ala Thr Ala Asn Ala Gly Gly Leu Gly Ile Leu Ala Ser Ala Thr Met
            35                  40                  45

Thr Leu Asp Glu Leu Ala Ala Ala Ile Thr Lys Val Lys Ala Val Thr
 50                  55                  60

Asp Lys Pro Phe Gly Val Asn Ile Arg Ala Asp Ala Asp Ala Gly
 65                  70                  75                  80

Asp Arg Val Glu Leu Met Ile Arg Glu Gly Val Arg Val Ala Ser Phe
                 85                  90                  95

Ala Leu Ala Pro Lys Gln Gln Leu Ile Ala Arg Leu Lys Glu Ala Gly
            100                 105                 110

Ala Val Val Ile Pro Ser Ile Gly Ala Ala Lys His Ala Arg Lys Val
            115                 120                 125

Ala Ala Trp Gly Ala Asp Ala Met Ile Val Gln Gly Gly Glu Gly Gly
130                 135                 140

Gly His Thr Gly Pro Val Ala Thr Thr Leu Leu Leu Pro Ser Val Leu
145                 150                 155                 160

Asp Ala Val Ala Gly Thr Gly Ile Pro Val Ile Ala Ala Gly Gly Phe
                165                 170                 175

Phe Asp Gly Arg Gly Leu Ala Ala Ala Leu Cys Tyr Gly Ala Ala Gly
            180                 185                 190

Val Ala Met Gly Thr Arg Phe Leu Leu Thr Ser Asp Ser Thr Val Pro
            195                 200                 205

Asp Ala Val Lys Arg Arg Tyr Leu Gln Ala Gly Leu Asp Gly Thr Val
            210                 215                 220

Val Thr Thr Arg Val Asp Gly Met Pro His Arg Val Leu Arg Thr Glu
225                 230                 235                 240

Leu Val Glu Lys Leu Glu Ser Gly Ser Arg Ala Arg Gly Phe Ala Ala
                245                 250                 255

Ala Leu Arg Asn Ala Gly Lys Phe Arg Arg Met Ser Gln Met Thr Trp
            260                 265                 270

Arg Ser Met Ile Arg Asp Gly Leu Thr Met Arg His Gly Lys Glu Leu
            275                 280                 285

Thr Trp Ser Gln Val Leu Met Ala Ala Asn Thr Pro Met Leu Leu Lys
290                 295                 300

Ala Gly Leu Val Asp Gly Asn Thr Glu Ala Gly Val Leu Ala Ser Gly
305                 310                 315                 320

Gln Val Ala Gly Ile Leu Asp Asp Leu Pro Ser Cys Lys Glu Leu Ile
            325                 330                 335

Glu Ser Ile Val Leu Asp Ala Ile Thr His Leu Gln Thr Ala Ser Ala
            340                 345                 350

Leu Val Glu
      355

<210> SEQ ID NO 29
<211> LENGTH: 969
<212> TYPE: DNA
<213> ORGANISM: Mycobacterium tuberculosis rv0021c

<400> SEQUENCE: 29

```
gtggtgctat cgacggcctt tagccagatg ttcggaatcg actatccgat agtgtccgcg    60
ccaatggact tgatcgccgg cggtgagctg gctgccgcgg taagtggcgc aggggactc   120
ggcctcatcg ggggcggcta tgggaccgg gattggttgg cccggcagtt cgatctcgcc   180
gctggagcgc cggtgggctg cgggttcatc acctggtctt tggcccgcca accgcagctg   240
```

```
ctcgacctcg cgctgcagta tgagccggtg gcggtgatgc tgtcgttcgg ggaccccgcg    300
gttttcgctg acgccatcaa gtccgccgga acgcggttgg tctgccagat ccaaaaccgg    360
acccaggccg agcgagccct gcaggtcggc gccgatgtgt tggtggctca gggcaccgag    420
gccggtgggc acggccacgg tccacgttcc accctgacct tggtacccga aatcgtcgac    480
ctggtcaccg cgcggggaac tgatatcccg gtgatcgccg ccgggggcat cgccgacggc    540
cggggccttg ccgccgcgtt gatgttgggc gccgccgggg tattggtcgg tacgcgcttc    600
tacgccacgt tcgaagcgtt atccacaccg caggcgcggg acccgctgct ggcggccact    660
ggcgacgaca tgtgccgcac cactatctac gatcagctac ggcgctatcc ctggccgcaa    720
ggacacacga tgagcgtgct aagcaacgcc ctcaccgacc aattcgagga caccgaactc    780
gacattctcc atcgcgaaga agccatggcc agatattggc gagccgttgc tgcgcgtgac    840
tacagcatcc caatgtcac cgccggtcaa gccgcgggcc tggtcaatgc cgtcctgcca    900
gccgccgacg tgataaccgg tatggcgcaa caagcggcga ggacgctgac cgcgatgcgc    960
gccgtgtaa                                                            969
```

<210> SEQ ID NO 30
<211> LENGTH: 322
<212> TYPE: PRT
<213> ORGANISM: Mycobacterium tuberculosis rv0021c

<400> SEQUENCE: 30

```
Met Val Leu Ser Thr Ala Phe Ser Gln Met Phe Gly Ile Asp Tyr Pro
1               5                   10                  15

Ile Val Ser Ala Pro Met Asp Leu Ile Ala Gly Gly Glu Leu Ala Ala
            20                  25                  30

Ala Val Ser Gly Ala Gly Gly Leu Gly Leu Ile Gly Gly Tyr Gly
        35                  40                  45

Asp Arg Asp Trp Leu Ala Arg Gln Phe Asp Leu Ala Ala Gly Ala Pro
    50                  55                  60

Val Gly Cys Gly Phe Ile Thr Trp Ser Leu Ala Arg Gln Pro Gln Leu
65                  70                  75                  80

Leu Asp Leu Ala Leu Gln Tyr Glu Pro Val Ala Val Met Leu Ser Phe
                85                  90                  95

Gly Asp Pro Ala Val Phe Ala Asp Ala Ile Lys Ser Ala Gly Thr Arg
            100                 105                 110

Leu Val Cys Gln Ile Gln Asn Arg Thr Gln Ala Glu Arg Ala Leu Gln
        115                 120                 125

Val Gly Ala Asp Val Leu Val Ala Gln Gly Thr Glu Ala Gly Gly His
    130                 135                 140

Gly His Gly Pro Arg Ser Thr Leu Thr Leu Val Pro Glu Ile Val Asp
145                 150                 155                 160

Leu Val Thr Ala Arg Gly Thr Asp Ile Pro Val Ile Ala Ala Gly Gly
                165                 170                 175

Ile Ala Asp Gly Arg Gly Leu Ala Ala Leu Met Leu Gly Ala Ala
            180                 185                 190

Gly Val Leu Val Gly Thr Arg Phe Tyr Ala Thr Val Glu Ala Leu Ser
        195                 200                 205

Thr Pro Gln Ala Arg Asp Pro Leu Leu Ala Ala Thr Gly Asp Asp Met
    210                 215                 220

Cys Arg Thr Thr Ile Tyr Asp Gln Leu Arg Arg Tyr Pro Trp Pro Gln
225                 230                 235                 240
```

```
Gly His Thr Met Ser Val Leu Ser Asn Ala Leu Thr Asp Gln Phe Glu
            245                 250                 255

Asp Thr Glu Leu Asp Ile Leu His Arg Glu Glu Ala Met Ala Arg Tyr
        260                 265                 270

Trp Arg Ala Val Ala Ala Arg Asp Tyr Ser Ile Ala Asn Val Thr Ala
        275                 280                 285

Gly Gln Ala Ala Gly Leu Val Asn Ala Val Leu Pro Ala Ala Asp Val
        290                 295                 300

Ile Thr Gly Met Ala Gln Gln Ala Ala Arg Thr Leu Thr Ala Met Arg
305                 310                 315                 320

Ala Val
```

```
<210> SEQ ID NO 31
<211> LENGTH: 1131
<212> TYPE: DNA
<213> ORGANISM: Mycobacterium tuberculosis rv1894c

<400> SEQUENCE: 31
```

| | | | | | |
|---|---|---|---|---|---|
| atgcacactg | ccatttgcga | cgagctcggt | atcgagtttc | ctattttgc | cttcactcac | 60 |
| tgccgcgatg | tggtggtcgc | cgtcagcaaa | gctggtggtt | ttggtgtgct | cggagcagtt | 120 |
| gggttcacgc | cggagcagct | ggagatcgag | ctcaactgga | tcgatgaaca | catcggcgac | 180 |
| caccctacg | gggtcgacat | cgtgatcccg | aacaagtacg | agggcatgga | ctcccagctg | 240 |
| tcggcggatg | agctcgccaa | gacgctgcgg | tcgatggtcc | cgcaggagca | tctggacttc | 300 |
| gcccgcaaga | tcctcgccga | tcatggtgtc | ccggtcgagg | acgccgacga | ggacagtctg | 360 |
| cagctgctcg | gttggaccga | ggcgacggcc | accccacagg | tcgacgcggc | gctgaagcac | 420 |
| cccaagatga | cgatggtcgc | caacgcgctt | ggcaccccc | cagcggacat | gatcaagcac | 480 |
| atccacgact | cgggtcgcaa | ggtggccgca | ttgtgcggct | caccctcgca | ggcccgcaag | 540 |
| cacgccgatg | cgggcgtcga | catcatcatc | gcccagggcg | gcgaggccgg | cgggcactgt | 600 |
| ggcgaggtgg | gctccattgt | gttgtggcct | caggtcgtca | aggaggtagc | gccggttccg | 660 |
| gtgttggcgg | cgggtggcat | cggcagcggt | cagcagatcg | ctgcagcgtt | ggcgctgggg | 720 |
| acccaagggg | catggaccgg | ttcgcagtgg | ctgatggtcg | aggaagccgc | aaacaccgcg | 780 |
| gttcaacagg | ccgcatacgt | caaggcgacc | agccgcgaca | ccgtgcgcag | tcgttccttc | 840 |
| acgggtaagc | cggcccggat | gctgcgcaac | gactggactg | aggcctggga | gcaaccggag | 900 |
| agcccgaagc | cgctcggtat | gccgttgcaa | tacatggtct | ccggcatggc | cgtcaaagcc | 960 |
| acacataaat | acccgaacga | gaccgtcgac | gtcgcgttca | acccggtggg | gcaggttgtt | 1020 |
| gggcagttca | ccaaggtgga | aaagacggct | accgttatcg | aacgctgggt | gcaggagtac | 1080 |
| ctcgaggcga | ccgcccggtt | ggacgcactc | aatgctgccg | cgtccgtttg | a | 1131 |

```
<210> SEQ ID NO 32
<211> LENGTH: 376
<212> TYPE: PRT
<213> ORGANISM: Mycobacterium tuberculosis rv1894c

<400> SEQUENCE: 32
```

```
Met His Thr Ala Ile Cys Asp Glu Leu Gly Ile Glu Phe Pro Ile Phe
1               5                   10                  15

Ala Phe Thr His Cys Arg Asp Val Val Ala Val Ser Lys Ala Gly
            20                  25                  30

Gly Phe Gly Val Leu Gly Ala Val Gly Phe Thr Pro Glu Gln Leu Glu
```

```
                35                  40                  45
Ile Glu Leu Asn Trp Ile Asp Glu His Ile Gly Asp His Pro Tyr Gly
             50                  55                  60
Val Asp Ile Val Ile Pro Asn Lys Tyr Glu Gly Met Asp Ser Gln Leu
 65                  70                  75                  80
Ser Ala Asp Glu Leu Ala Lys Thr Leu Arg Ser Met Val Pro Gln Glu
                 85                  90                  95
His Leu Asp Phe Ala Arg Lys Ile Leu Ala Asp His Gly Val Pro Val
                100                 105                 110
Glu Asp Ala Asp Glu Asp Ser Leu Gln Leu Leu Gly Trp Thr Glu Ala
            115                 120                 125
Thr Ala Thr Pro Gln Val Asp Ala Ala Leu Lys His Pro Lys Met Thr
        130                 135                 140
Met Val Ala Asn Ala Leu Gly Thr Pro Pro Ala Asp Met Ile Lys His
145                 150                 155                 160
Ile His Asp Ser Gly Arg Lys Val Ala Ala Leu Cys Gly Ser Pro Ser
                165                 170                 175
Gln Ala Arg Lys His Ala Asp Ala Gly Val Asp Ile Ile Ile Ala Gln
            180                 185                 190
Gly Gly Glu Ala Gly Gly His Cys Gly Glu Val Gly Ser Ile Val Leu
        195                 200                 205
Trp Pro Gln Val Val Lys Glu Val Ala Pro Val Pro Val Leu Ala Ala
210                 215                 220
Gly Gly Ile Gly Ser Gly Gln Gln Ile Ala Ala Ala Leu Ala Leu Gly
225                 230                 235                 240
Thr Gln Gly Ala Trp Thr Gly Ser Gln Trp Leu Met Val Glu Glu Ala
                245                 250                 255
Ala Asn Thr Ala Val Gln Gln Ala Ala Tyr Val Lys Ala Thr Ser Arg
            260                 265                 270
Asp Thr Val Arg Ser Arg Ser Phe Thr Gly Lys Pro Ala Arg Met Leu
        275                 280                 285
Arg Asn Asp Trp Thr Glu Ala Trp Glu Gln Pro Glu Ser Pro Lys Pro
290                 295                 300
Leu Gly Met Pro Leu Gln Tyr Met Val Ser Gly Met Ala Val Lys Ala
305                 310                 315                 320
Thr His Lys Tyr Pro Asn Glu Thr Val Asp Val Ala Phe Asn Pro Val
                325                 330                 335
Gly Gln Val Val Gly Gln Phe Thr Lys Val Glu Lys Thr Ala Thr Val
            340                 345                 350
Ile Glu Arg Trp Val Gln Glu Tyr Leu Glu Ala Thr Ala Arg Leu Asp
        355                 360                 365
Ala Leu Asn Ala Ala Ala Ser Val
    370                 375

<210> SEQ ID NO 33
<211> LENGTH: 945
<212> TYPE: DNA
<213> ORGANISM: Thermotoga maritima

<400> SEQUENCE: 33
atgaccgtga gaacaagagt gacagatctt ctggaaatag agcatccaat cctcatgggt      60
ggaatggcct gggcgggaac tcccacccte gcagcagcgg tatcggaggc gggaggactt     120
ggaatcatcg gatccggagc catgaagccg gacgacctga gaaaagcgat ctccgaactc     180
```

-continued

```
agacagaaga cggacaaacc cttcggtgta aacataatcc ttgtctctcc gtgggcggac      240
gatctcgtca aggtgtgcat agaagagaaa gtacccgtcg tcacgttcgg tgcgggaaac      300
ccaacgaagt acataaggga actcaaggaa acggaacaa aggtgatacc cgttgtcgcc      360
tccgactctc tggcaaggat ggtggaaaga gcgggagcgg atgcggtgat agcggaaggg      420
atggagtccg gtggacacat agtgaagtc acaaccttcg ttctcgtcaa caaagtctcc      480
aggagtgtga acatccccgt gatcgcagcg ggaggcatcg ccgacggaag aggtatggca      540
gccgccttcg cactcggagc ggaagccgtt cagatgggaa ccaggtttgt ggcgagtgtg      600
gaaagcgacg tgcacccggt ttacaaagaa aagatcgtca aggcttccat aagagacacc      660
gttgtgacgg gagccaaact tggacacccc gcgcgcgttc tcagaactcc ctttgcaagg      720
aagatccagg agatggagtt tgaaaacccc atgcaggctg aagaaatgct ggtgggaagt      780
ctcagaagag cggtcgttga aggcgatctg gagagaggat ccttcatggt gggacagagc      840
gccggcttga tcgatgagat aaaaccggtg aagcagatca tagaggatat cctgaaggag      900
ttcaaagaaa cggtggagaa gctgaggggg tacatcgaag agtga                      945
```

<210> SEQ ID NO 34
<211> LENGTH: 314
<212> TYPE: PRT
<213> ORGANISM: Thermotoga maritima

<400> SEQUENCE: 34

```
Met Thr Val Arg Thr Arg Val Thr Asp Leu Leu Glu Ile Glu His Pro
1               5                   10                  15

Ile Leu Met Gly Gly Met Ala Trp Ala Gly Thr Pro Thr Leu Ala Ala
            20                  25                  30

Ala Val Ser Glu Ala Gly Gly Leu Gly Ile Ile Gly Ser Gly Ala Met
        35                  40                  45

Lys Pro Asp Asp Leu Arg Lys Ala Ile Ser Glu Leu Arg Gln Lys Thr
    50                  55                  60

Asp Lys Pro Phe Gly Val Asn Ile Ile Leu Val Ser Pro Trp Ala Asp
65                  70                  75                  80

Asp Leu Val Lys Val Cys Ile Glu Glu Lys Val Pro Val Val Thr Phe
                85                  90                  95

Gly Ala Gly Asn Pro Thr Lys Tyr Ile Arg Glu Leu Lys Glu Asn Gly
            100                 105                 110

Thr Lys Val Ile Pro Val Ala Ser Asp Ser Leu Ala Arg Met Val
        115                 120                 125

Glu Arg Ala Gly Ala Asp Ala Val Ile Ala Glu Gly Met Glu Ser Gly
    130                 135                 140

Gly His Ile Gly Glu Val Thr Thr Phe Val Leu Val Asn Lys Val Ser
145                 150                 155                 160

Arg Ser Val Asn Ile Pro Val Ile Ala Ala Gly Gly Ile Ala Asp Gly
                165                 170                 175

Arg Gly Met Ala Ala Ala Phe Ala Leu Gly Ala Glu Ala Val Gln Met
            180                 185                 190

Gly Thr Arg Phe Val Ala Ser Val Glu Ser Asp Val His Pro Val Tyr
        195                 200                 205

Lys Glu Lys Ile Val Lys Ala Ser Ile Arg Asp Thr Val Thr Gly
    210                 215                 220

Ala Lys Leu Gly His Pro Ala Arg Val Leu Arg Thr Pro Phe Ala Arg
225                 230                 235                 240
```

Lys Ile Gln Glu Met Glu Phe Glu Asn Pro Met Gln Ala Glu Met
                245                 250                 255

Leu Val Gly Ser Leu Arg Arg Ala Val Val Glu Gly Asp Leu Glu Arg
            260                 265                 270

Gly Ser Phe Met Val Gly Gln Ser Ala Gly Leu Ile Asp Glu Ile Lys
        275                 280                 285

Pro Val Lys Gln Ile Ile Glu Asp Ile Leu Lys Glu Phe Lys Glu Thr
    290                 295                 300

Val Glu Lys Leu Arg Gly Tyr Ile Glu Glu
305                 310

<210> SEQ ID NO 35
<211> LENGTH: 1092
<212> TYPE: DNA
<213> ORGANISM: Helicobacter pylori

<400> SEQUENCE: 35

```
atggtatcaa cactcaaacc gctaaaaatc ggtaaacaca ccataaaatt ccctattttt      60
caagggggca tgggtgtggg gattagctgg gatgaactag ctggaaatgt tgccaaagaa     120
ggggctttag gagtgatttc agccgtaggg actggttatt ataaaaacat gcgttttgta     180
gaaaggattg tggctaaaaa acccttttgaa gccttgaatt tttactccaa aaaagcgttg    240
aatgagattt ttgcaaacgc taggaaaatt tgcgggaaca agcctttggg ggcgaatatt    300
ttatacgcta tcaatgacta tggccgtgtt ttaagggact cttgtgaggc gggggcgaat    360
attatcatta caggggctgg tttgcccact aacatgcctg aattcgctaa ggattttagc    420
gatgtggcgc tcatccctat catttcctca gcgaaggctt taaaaatcct ttgtaaaaga    480
tggagcgatc gctataaaag aatcccggac gcattcattg tggaagggcc tttgagtggg    540
gggcatcagg gctttaaata cgaagattgt ttcaaagaag aattccaatt agaaaactta    600
gtgcctaaag tcgtggaagc ttctaaagaa tgggggaata tccctatcat cgccgcgggg    660
gggatttggg ataagaaaga tatagacacc atgttaagcc ttggagcgag tggggtgcaa    720
atggcgactc gttttttagg cacgaaagaa tgcgacgcta aagcgtatgc cgatcttttg    780
cccacgctca aaaagaaga tattttactc atcaaatcgc ctgtaggcta tccggctagg    840
gctatcaata cggggggtgat caaacgcatt gaagagggta acgcgcctaa aatcgcatgc    900
gtgagcaatt gtgtagcgcc ttgtaacagg ggtgaagaag ctaaaaaggt gggctattgt    960
atcgctgatg gtttggggcg cagttattta ggaaacagag aagagggct ttattttacc    1020
ggggctaatg gctatagagt ggataagatt atcagcgtgc atgaattgat taaagagctt    1080
acagagggtt aa                                                         1092
```

<210> SEQ ID NO 36
<211> LENGTH: 363
<212> TYPE: PRT
<213> ORGANISM: Helicobacter pylori

<400> SEQUENCE: 36

Met Val Ser Thr Leu Lys Pro Leu Lys Ile Gly Lys His Thr Ile Lys
1               5                   10                  15

Phe Pro Ile Phe Gln Gly Gly Met Gly Val Gly Ile Ser Trp Asp Glu
            20                  25                  30

Leu Ala Gly Asn Val Ala Lys Glu Gly Ala Leu Gly Val Ile Ser Ala
        35                  40                  45

Val Gly Thr Gly Tyr Tyr Lys Asn Met Arg Phe Val Glu Arg Ile Val

```
                50                      55                      60
Ala Lys Lys Pro Phe Glu Ala Leu Asn Phe Tyr Ser Lys Lys Ala Leu
65                      70                      75                      80

Asn Glu Ile Phe Ala Asn Ala Arg Lys Ile Cys Gly Asn Lys Pro Leu
                        85                      90                      95

Gly Ala Asn Ile Leu Tyr Ala Ile Asn Asp Tyr Gly Arg Val Leu Arg
                100                     105                     110

Asp Ser Cys Glu Ala Gly Ala Asn Ile Ile Ile Thr Gly Ala Gly Leu
            115                     120                     125

Pro Thr Asn Met Pro Glu Phe Ala Lys Asp Phe Ser Asp Val Ala Leu
        130                     135                     140

Ile Pro Ile Ile Ser Ser Ala Lys Ala Leu Lys Ile Leu Cys Lys Arg
145                     150                     155                     160

Trp Ser Asp Arg Tyr Lys Arg Ile Pro Asp Ala Phe Ile Val Glu Gly
                        165                     170                     175

Pro Leu Ser Gly Gly His Gln Gly Phe Lys Tyr Glu Asp Cys Phe Lys
                180                     185                     190

Glu Glu Phe Gln Leu Glu Asn Leu Val Pro Lys Val Val Glu Ala Ser
            195                     200                     205

Lys Glu Trp Gly Asn Ile Pro Ile Ile Ala Ala Gly Gly Ile Trp Asp
        210                     215                     220

Lys Lys Asp Ile Asp Thr Met Leu Ser Leu Gly Ala Ser Gly Val Gln
225                     230                     235                     240

Met Ala Thr Arg Phe Leu Gly Thr Lys Glu Cys Asp Ala Lys Ala Tyr
                        245                     250                     255

Ala Asp Leu Leu Pro Thr Leu Lys Lys Glu Asp Ile Leu Leu Ile Lys
                260                     265                     270

Ser Pro Val Gly Tyr Pro Ala Arg Ala Ile Asn Thr Gly Val Ile Lys
            275                     280                     285

Arg Ile Glu Glu Gly Asn Ala Pro Lys Ile Ala Cys Val Ser Asn Cys
        290                     295                     300

Val Ala Pro Cys Asn Arg Gly Glu Glu Ala Lys Lys Val Gly Tyr Cys
305                     310                     315                     320

Ile Ala Asp Gly Leu Gly Arg Ser Tyr Leu Gly Asn Arg Glu Glu Gly
                        325                     330                     335

Leu Tyr Phe Thr Gly Ala Asn Gly Tyr Arg Val Asp Lys Ile Ile Ser
                340                     345                     350

Val His Glu Leu Ile Lys Glu Leu Thr Glu Gly
            355                     360

<210> SEQ ID NO 37
<211> LENGTH: 825
<212> TYPE: DNA
<213> ORGANISM: Archaeoglobus fulgidus

<400> SEQUENCE: 37
atgaacagga ttgctaaact cctcaaaacg aagtatccga tagttcaggg cccgatggcc      60
ggaataactc tcggagaatt tgcttctaca gtgtctgagg ctggcgggct tggagttata     120
gcttctgccg gcctttcgcc tgaaaaacta aagaggaga tagagaaagt taagaacagg     180
actgataagc ccttcgccgt gaacattcca atatatcagc ccggctcgga agagaatctt     240
gagactgcac ttaaagctga tgttgggatt atttacacct ctgcaggaag cccggagaaa     300
tacactgaga gagtaaagga atccggggca aaagtcatac acaaggtgtc gaggttgaaa     360
```

-continued

```
gaggggctga aagcggagaa ggcgggagtg gatgctgtgg ttgcgatggg ctttgaggcg    420
ggagggatta tagggaggag tggtgtaaca tccttctgct tgattcctga gcttgccgac    480
aacctcagca ttccagttgt agccgctggc gggatagcag atgagagggg atttgctgca    540
gccctgattc tcggagcgga aggtgttgag attggcacga gactgcttgc aaccaaagag    600
tgtcccgtgc cggaaagcat taagcaagct attttaaaag ccacctgcga ctccacgatg    660
gttattgaga gcccggttgt aatgagagct ctcaagccag agctgagcgg agattctgag    720
aatcctgctc tggagggca ggtttcaggg ctgattaagg agattcttac ggttgaagag    780
gtaatcagga aaattgcaga ggggctgaat aaagctaaat tctaa                   825
```

<210> SEQ ID NO 38
<211> LENGTH: 274
<212> TYPE: PRT
<213> ORGANISM: Archaeoglobus fulgidus

<400> SEQUENCE: 38

Met Asn Arg Ile Ala Lys Leu Leu Lys Thr Lys Tyr Pro Ile Val Gln
1               5                   10                  15

Gly Pro Met Ala Gly Ile Thr Leu Gly Glu Phe Ala Ser Thr Val Ser
                20                  25                  30

Glu Ala Gly Gly Leu Gly Val Ile Ala Ser Ala Gly Leu Ser Pro Glu
            35                  40                  45

Lys Leu Lys Glu Glu Ile Glu Lys Val Lys Asn Arg Thr Asp Lys Pro
        50                  55                  60

Phe Ala Val Asn Ile Pro Ile Tyr Gln Pro Gly Ser Glu Lys Asn Leu
65                  70                  75                  80

Glu Thr Ala Leu Lys Ala Asp Val Gly Ile Ile Tyr Thr Ser Ala Gly
                85                  90                  95

Ser Pro Glu Lys Tyr Thr Glu Arg Val Lys Glu Ser Gly Ala Lys Val
            100                 105                 110

Ile His Lys Val Ser Arg Leu Lys Glu Gly Leu Lys Ala Glu Lys Ala
        115                 120                 125

Gly Val Asp Ala Val Ala Met Gly Phe Glu Ala Gly Gly Ile Ile
    130                 135                 140

Gly Arg Ser Gly Val Thr Ser Phe Cys Leu Ile Pro Glu Leu Ala Asp
145                 150                 155                 160

Asn Leu Ser Ile Pro Val Val Ala Ala Gly Gly Ile Ala Asp Glu Arg
                165                 170                 175

Gly Phe Ala Ala Ala Leu Ile Leu Gly Ala Glu Gly Val Glu Ile Gly
            180                 185                 190

Thr Arg Leu Leu Ala Thr Lys Glu Cys Pro Val Pro Glu Ser Ile Lys
        195                 200                 205

Gln Ala Ile Leu Lys Ala Thr Cys Asp Ser Thr Met Val Ile Glu Ser
    210                 215                 220

Pro Val Val Met Arg Ala Leu Lys Pro Glu Leu Ser Gly Asp Ser Glu
225                 230                 235                 240

Asn Pro Ala Leu Gly Gly Gln Val Ser Gly Leu Ile Lys Glu Ile Leu
                245                 250                 255

Thr Val Glu Glu Val Ile Arg Lys Ile Ala Glu Gly Leu Asn Lys Ala
            260                 265                 270

Lys Phe

<210> SEQ ID NO 39

```
<211> LENGTH: 1125
<212> TYPE: DNA
<213> ORGANISM: Williopsis saturnus

<400> SEQUENCE: 39
atgagatcac aaatacagag cttcctaaag acgtttgaag tcaggtatcc tattattcag      60
gccccaatgg ctggcgcttc gaccttggaa ctcgcagcca ccgtaaccag actcggaggc     120
attggttcga tccctatggg ctcgctgagt gagaagtgtg atgctattga acccagctg      180
gaaaattttg atgaattggt tggtgattct ggaaggatag tcaacttgaa cttctttgct     240
cataaggagc ctcgttctgg gagagctgat gtcaacgagg aatggctcaa gaagtatgac     300
aagatatatg gcaaagccgg aattgagttt gacaaaaagg agctgaagtt gttatatcca     360
tcttttaggt ccattgttga tccacaacat ccgactgtgc ggctactgaa gaatctcaag     420
ccaaagattg tcagtttcca ctttgggtta ccccatgagg cggtgattga atctctccag     480
gcaagcgata ttaagatctt tgtcactgtc acaaatctac aggagtttca gcaggcttat     540
gagtctaaat tggatggtgt cgtcctacaa ggatgggaag ctggtggaca tcgtggtaat     600
ttcaaggcta atgacgtcga agatggacaa ctgaagacgt tggatctcgt tagtactatt     660
gttgattaca ttgactcggc tagtatctcc aatccaccat ttatcattgc agcgggtggt     720
attcatgatg atgagtccat caaagaattg cttcaattca acattgctgc cgttcagttg     780
ggtactgttt ggttaccatc gagccaggcc acaatatctc ctgaacattt gaagatgttt     840
caatccccaa aaagtgacac gatgatgacc gcagccattt caggacgtaa cttgagaacg     900
atcagtacac ctttcttgag ggatcttcat caatcttcac cattggcctc gatccctgat     960
tatccattac cttacgacag cttttaagtca cttgctaatg acgctaagca agtggaaaa    1020
gggcctcagt actccgcatt tcttgctgga tctaactatc acaaatcttg gaaggatacg    1080
agatccactg aagagatatt ctcgatatta gtacaggatc tataa                    1125

<210> SEQ ID NO 40
<211> LENGTH: 374
<212> TYPE: PRT
<213> ORGANISM: Williopsis saturnus

<400> SEQUENCE: 40

Met Arg Ser Gln Ile Gln Ser Phe Leu Lys Thr Phe Glu Val Arg Tyr
1               5                   10                  15

Pro Ile Ile Gln Ala Pro Met Ala Gly Ala Ser Thr Leu Glu Leu Ala
            20                  25                  30

Ala Thr Val Thr Arg Leu Gly Gly Ile Gly Ser Ile Pro Met Gly Ser
        35                  40                  45

Leu Ser Glu Lys Cys Asp Ala Ile Glu Thr Gln Leu Glu Asn Phe Asp
    50                  55                  60

Glu Leu Val Gly Asp Ser Gly Arg Ile Val Asn Leu Asn Phe Phe Ala
65                  70                  75                  80

His Lys Glu Pro Arg Ser Gly Arg Ala Asp Val Asn Glu Glu Trp Leu
                85                  90                  95

Lys Lys Tyr Asp Lys Ile Tyr Gly Lys Ala Gly Ile Glu Phe Asp Lys
            100                 105                 110

Lys Glu Leu Lys Leu Leu Tyr Pro Ser Phe Arg Ser Ile Val Asp Pro
        115                 120                 125

Gln His Pro Thr Val Arg Leu Leu Lys Asn Leu Lys Pro Lys Ile Val
    130                 135                 140
```

```
Ser Phe His Phe Gly Leu Pro His Glu Ala Val Ile Glu Ser Leu Gln
145                 150                 155                 160

Ala Ser Asp Ile Lys Ile Phe Val Thr Val Thr Asn Leu Gln Glu Phe
            165                 170                 175

Gln Gln Ala Tyr Glu Ser Lys Leu Asp Gly Val Val Leu Gln Gly Trp
                180                 185                 190

Glu Ala Gly Gly His Arg Gly Asn Phe Lys Ala Asn Asp Val Glu Asp
            195                 200                 205

Gly Gln Leu Lys Thr Leu Asp Leu Val Ser Thr Ile Val Asp Tyr Ile
    210                 215                 220

Asp Ser Ala Ser Ile Ser Asn Pro Pro Phe Ile Ile Ala Ala Gly Gly
225                 230                 235                 240

Ile His Asp Asp Glu Ser Ile Lys Glu Leu Leu Gln Phe Asn Ile Ala
                245                 250                 255

Ala Val Gln Leu Gly Thr Val Trp Leu Pro Ser Ser Gln Ala Thr Ile
            260                 265                 270

Ser Pro Glu His Leu Lys Met Phe Gln Ser Pro Lys Ser Asp Thr Met
    275                 280                 285

Met Thr Ala Ala Ile Ser Gly Arg Asn Leu Arg Thr Ile Ser Thr Pro
290                 295                 300

Phe Leu Arg Asp Leu His Gln Ser Ser Pro Leu Ala Ser Ile Pro Asp
305                 310                 315                 320

Tyr Pro Leu Pro Tyr Asp Ser Phe Lys Ser Leu Ala Asn Asp Ala Lys
                325                 330                 335

Gln Ser Gly Lys Gly Pro Gln Tyr Ser Ala Phe Leu Ala Gly Ser Asn
            340                 345                 350

Tyr His Lys Ser Trp Lys Asp Thr Arg Ser Thr Glu Glu Ile Phe Ser
    355                 360                 365

Ile Leu Val Gln Asp Leu
    370

<210> SEQ ID NO 41
<211> LENGTH: 1215
<212> TYPE: DNA
<213> ORGANISM: Saccharomyces cerevisiae

<400> SEQUENCE: 41
atgtactttt taaaccaact aatatttcaa gacgtttccg taatgtcggt ggataaaaga    60
gaagatatga gcagatcttt ccaaaaatgt ttaaacttga tacccctat catccaggcc   120 cctatggcgg gggtcacgac tattgaaatg gccgctaagg cttgtattgc gggcgccata   180
gcttcactac ccctatccca cttagacttc agaaaggtca atgatattga aaagcttaaa   240
ctgatggttt cacaattcag agatcaagta gccgatgaat ctttagaggg caatctcaac   300
ctaaactttt tttgccatga tatcgttgat aaaccgaccg atcttcaaac agctaactgg   360
gcgaagctat acagaaagtc tatgaatgtg ccgattgata tgaatgagat taaattcgat   420
aatggtaatg tatcttttaa ggcatttgaa aagaaaatg ctcttcaaga ttttttccag   480
tacctatcag atggctttag gcctaaaatc attagtttcc attttggcca tccgtcgaaa   540
tctacaatag aatatttaca aaaaattgga attctaattt ttgtgactgc cacctctgta   600
agagaagttc gattgttagc acgtctcggc attaatggca tagtgtgtca aggctatgaa   660 gcggaggac atagaggaaa tttcttagta aatgaccccca agatgatga aaacttatca   720 actgtacaat tggtgaaaag aacagttgat gaacttgctg aaatgaaaaa taaaggtctt   780
```

-continued

```
atacatgcta ctcccttttgt cattgcagca ggtggtataa tggattccaa agatatatca    840
tacatgttat cacagcaagc agacgctgtt caagtgggga ctgcttttct tggttgcagt    900
gaatccaatg catcaaaaaa cttttcaagc cccttcactc gagaaacaac aactaaaatg    960
gttaatataa tatcaggaaa gcctgcaagg accatctcta ctccttttat cgaaaaagtc   1020
attgctaatt ttcaaggtga ggagcttcct ccatatggct acatgtatag tgctttcaag   1080
caagtaagaa aaaagtatcc agaattggct aactttattt tagctggaca aggatttcag   1140
aatgtccaat caggaatcac aacagacaag aaaattgaaa ctatgggcgc aagattgaaa   1200
attgtcggaa aataa                                                    1215
```

<210> SEQ ID NO 42
<211> LENGTH: 404
<212> TYPE: PRT
<213> ORGANISM: Saccharomyces cerevisiae

<400> SEQUENCE: 42

```
Met Tyr Phe Leu Asn Gln Leu Ile Phe Gln Asp Val Ser Val Met Ser
1               5                   10                  15

Val Asp Lys Arg Glu Asp Met Ser Arg Ser Phe Gln Lys Cys Leu Asn
            20                  25                  30

Leu Arg Tyr Pro Ile Ile Gln Ala Pro Met Ala Gly Val Thr Thr Ile
        35                  40                  45

Glu Met Ala Ala Lys Ala Cys Ile Ala Gly Ala Ile Ala Ser Leu Pro
 50                  55                  60

Leu Ser His Leu Asp Phe Arg Lys Val Asn Asp Ile Glu Lys Leu Lys
65                  70                  75                  80

Leu Met Val Ser Gln Phe Arg Asp Gln Val Ala Asp Glu Ser Leu Glu
                85                  90                  95

Gly Asn Leu Asn Leu Asn Phe Phe Cys His Asp Ile Val Asp Lys Pro
            100                 105                 110

Thr Asp Leu Gln Thr Ala Asn Trp Ala Lys Leu Tyr Arg Lys Ser Met
        115                 120                 125

Asn Val Pro Ile Asp Met Asn Glu Ile Lys Phe Asp Asn Gly Asn Val
    130                 135                 140

Ser Phe Lys Ala Phe Glu Lys Glu Asn Ala Leu Gln Asp Phe Phe Gln
145                 150                 155                 160

Tyr Leu Ser Asp Gly Phe Arg Pro Lys Ile Ile Ser Phe His Phe Gly
                165                 170                 175

His Pro Ser Lys Ser Thr Ile Glu Tyr Leu Gln Lys Ile Gly Ile Leu
            180                 185                 190

Ile Phe Val Thr Ala Thr Ser Val Arg Glu Val Arg Leu Leu Ala Arg
        195                 200                 205

Leu Gly Ile Asn Gly Ile Val Cys Gln Gly Tyr Glu Ala Gly His
    210                 215                 220

Arg Gly Asn Phe Leu Val Asn Asp Pro Lys Asp Asp Glu Asn Leu Ser
225                 230                 235                 240

Thr Val Gln Leu Val Lys Arg Thr Val Asp Glu Leu Ala Glu Met Lys
                245                 250                 255

Asn Lys Gly Leu Ile His Ala Thr Pro Phe Val Ile Ala Ala Gly Gly
            260                 265                 270

Ile Met Asp Ser Lys Asp Ile Ser Tyr Met Leu Ser Gln Gln Ala Asp
        275                 280                 285

Ala Val Gln Val Gly Thr Ala Phe Leu Gly Cys Ser Glu Ser Asn Ala
```

```
                290                    295                    300
Ser Lys Asn Phe Ser Ser Pro Phe Thr Arg Glu Thr Thr Lys Met
305                 310                 315                 320

Val Asn Ile Ile Ser Gly Lys Pro Ala Arg Thr Ile Ser Thr Pro Phe
                325                 330                 335

Ile Glu Lys Val Ile Ala Asn Phe Gln Gly Glu Glu Leu Pro Pro Tyr
            340                 345                 350

Gly Tyr Met Tyr Ser Ala Phe Lys Gln Val Arg Lys Tyr Pro Glu
            355                 360                 365

Leu Ala Asn Phe Ile Leu Ala Gly Gln Gly Phe Gln Asn Val Gln Ser
        370                 375                 380

Gly Ile Thr Thr Asp Lys Lys Ile Glu Thr Met Gly Ala Arg Leu Lys
385                 390                 395                 400

Ile Val Gly Lys

<210> SEQ ID NO 43
<211> LENGTH: 1137
<212> TYPE: DNA
<213> ORGANISM: Neurospora crassa

<400> SEQUENCE: 43
atgcacttcc caggccacag cagcaagaag gaggaatctg cccaagcggc cctcacgaag      60
ctgaactcct ggttccccac caccaagaac cccgtcatca tcagcgcccc catgtatctc     120
atcgccaacg gcactcttgc ggccgaggta tccaaggccg gcggtattgg ctttgtcgcc     180
ggcggctccg acttccgccc cggctcctcc cacctaaccg ccctctctac cgaactcgcc     240
tccgcccgca gccgctcgg tcttaccgac cgccccctca ccctctccc cggcattggc     300 gtcggcctca ttttaaccca caccatctcc gttccctacg taaccgacac cgtcctgccc     360
atcctgatcg aacactcccc gcaagcagtc tggctcttcg ccaacgaccc ggatttcgag     420
gcctcttccg agcctggcgc aaagggaaca gcaaagcaaa tcatcgaggc ccttcacgct     480
tcggggttcg tggtattctt tcaagtaggc acggtgaaa atgcaaggaa ggcggcggca     540
gatggggcag atgtgattgt tgcgcaaggg atcgatgcgg agggcatca gcttgctaca     600 gggagtggga ttgtgagttt ggtaccggag gttaggata tgcttgatag agagttcaag     660
gaacgagagg tggtggttgt ggcggcggga ggtgtggcgg atgggagggg ggttgtaggg     720
gcgctgggtc taggcgccga gggtgtggta ttgggtacta ggttcaccgt agcagtcgaa     780
gcttccaccc ccgagttccg caggaaggtc atcctcgaga caaacgatgg tggtctcaac     840
accgtcaaat cccatttcca cgaccaaatc aactgcaaca caatctggca caacgtctac     900
gacgggcgag ccgttcgcaa tgcctcctac gacgaccacg cggccggtgt cccctttgaa     960
gagaatcaca agaagttcaa ggaggcagcg agctctgggg ataactcgcg ggctgtgact    1020
tggtccggga ctgctgtggg tctgataaag gaccagaggc cggctggcga tattgttagg    1080
gagttgaggg aagaggccaa agagaggatc aagaagattc aggcttttgc tgcttaa      1137

<210> SEQ ID NO 44
<211> LENGTH: 378
<212> TYPE: PRT
<213> ORGANISM: Neurospora crassa

<400> SEQUENCE: 44

Met His Phe Pro Gly His Ser Ser Lys Lys Glu Glu Ser Ala Gln Ala
1               5                   10                  15
```

-continued

```
Ala Leu Thr Lys Leu Asn Ser Trp Phe Pro Thr Thr Lys Asn Pro Val
             20                  25                  30

Ile Ile Ser Ala Pro Met Tyr Leu Ile Ala Asn Gly Thr Leu Ala Ala
         35                  40                  45

Glu Val Ser Lys Ala Gly Gly Ile Gly Phe Val Ala Gly Gly Ser Asp
     50                  55                  60

Phe Arg Pro Gly Ser Ser His Leu Thr Ala Leu Ser Thr Glu Leu Ala
 65                  70                  75                  80

Ser Ala Arg Ser Arg Leu Gly Leu Thr Asp Arg Pro Leu Thr Pro Leu
                 85                  90                  95

Pro Gly Ile Gly Val Gly Leu Ile Leu Thr His Thr Ile Ser Val Pro
                100                 105                 110

Tyr Val Thr Asp Thr Val Leu Pro Ile Leu Ile Glu His Ser Pro Gln
            115                 120                 125

Ala Val Trp Leu Phe Ala Asn Asp Pro Asp Phe Glu Ala Ser Ser Glu
        130                 135                 140

Pro Gly Ala Lys Gly Thr Ala Lys Gln Ile Ile Glu Ala Leu His Ala
145                 150                 155                 160

Ser Gly Phe Val Val Phe Phe Gln Val Gly Thr Val Lys Asp Ala Arg
                165                 170                 175

Lys Ala Ala Asp Gly Ala Asp Val Ile Val Ala Gln Gly Ile Asp
                180                 185                 190

Ala Gly Gly His Gln Leu Ala Thr Gly Ser Gly Ile Val Ser Leu Val
            195                 200                 205

Pro Glu Val Arg Asp Met Leu Asp Arg Glu Phe Lys Glu Arg Glu Val
        210                 215                 220

Val Val Val Ala Ala Gly Gly Val Ala Asp Gly Arg Gly Val Val Gly
225                 230                 235                 240

Ala Leu Gly Leu Gly Ala Glu Gly Val Val Leu Gly Thr Arg Phe Thr
                245                 250                 255

Val Ala Val Glu Ala Ser Thr Pro Glu Phe Arg Arg Lys Val Ile Leu
            260                 265                 270

Glu Thr Asn Asp Gly Gly Leu Asn Thr Val Lys Ser His Phe His Asp
        275                 280                 285

Gln Ile Asn Cys Asn Thr Ile Trp His Asn Val Tyr Asp Gly Arg Ala
    290                 295                 300

Val Arg Asn Ala Ser Tyr Asp Asp His Ala Ala Gly Val Pro Phe Glu
305                 310                 315                 320

Glu Asn His Lys Lys Phe Lys Glu Ala Ala Ser Ser Gly Asp Asn Ser
                325                 330                 335

Arg Ala Val Thr Trp Ser Gly Thr Ala Val Gly Leu Ile Lys Asp Gln
            340                 345                 350

Arg Pro Ala Gly Asp Ile Val Arg Glu Leu Arg Glu Glu Ala Lys Glu
        355                 360                 365

Arg Ile Lys Lys Ile Gln Ala Phe Ala Ala
    370                 375

<210> SEQ ID NO 45
<211> LENGTH: 195
<212> TYPE: PRT
<213> ORGANISM: Unknown
<220> FEATURE:
<223> OTHER INFORMATION: Description of Unknown Organism: A FabK
      Consensus Sequence
<220> FEATURE:
<221> NAME/KEY: MISC_FEATURE
```

```
<222> LOCATION: (2)..(2)
<223> OTHER INFORMATION: X=Ile or Ala
<220> FEATURE:
<221> NAME/KEY: MISC_FEATURE
<222> LOCATION: (3)..(4)
<223> OTHER INFORMATION: X=any amino acid
<220> FEATURE:
<221> NAME/KEY: MISC_FEATURE
<222> LOCATION: (5)..(5)
<223> OTHER INFORMATION: X=Gly or Ala
<220> FEATURE:
<221> NAME/KEY: MISC_FEATURE
<222> LOCATION: (6)..(6)
<223> OTHER INFORMATION: X=Gly or Pro
<220> FEATURE:
<221> NAME/KEY: MISC_FEATURE
<222> LOCATION: (8)..(16)
<223> OTHER INFORMATION: X=any amino acid and up to 3 may be absent
<220> FEATURE:
<221> NAME/KEY: MISC_FEATURE
<222> LOCATION: (18)..(19)
<223> OTHER INFORMATION: X=Pro, Ala, Gly, Ser or Thr
<220> FEATURE:
<221> NAME/KEY: MISC_FEATURE
<222> LOCATION: (21)..(21)
<223> OTHER INFORMATION: X=Ser or Ala
<220> FEATURE:
<221> NAME/KEY: MISC_FEATURE
<222> LOCATION: (22)..(23)
<223> OTHER INFORMATION: X=any amino acid
<220> FEATURE:
<221> NAME/KEY: MISC_FEATURE
<222> LOCATION: (26)..(53)
<223> OTHER INFORMATION: X=any amino acid and up to 6 may be absent
<220> FEATURE:
<221> NAME/KEY: MISC_FEATURE
<222> LOCATION: (55)..(55)
<223> OTHER INFORMATION: X=Gln, Asn, Glu or Asp
<220> FEATURE:
<221> NAME/KEY: MISC_FEATURE
<222> LOCATION: (56)..(56)
<223> OTHER INFORMATION: X=any amino acid
<220> FEATURE:
<221> NAME/KEY: MISC_FEATURE
<222> LOCATION: (59)..(59)
<223> OTHER INFORMATION: X=Gly or Ala
<220> FEATURE:
<221> NAME/KEY: MISC_FEATURE
<222> LOCATION: (61)..(165)
<223> OTHER INFORMATION: X=any amino acid and up to 15 may be absent
<220> FEATURE:
<221> NAME/KEY: MISC_FEATURE
<222> LOCATION: (167)..(168)
<223> OTHER INFORMATION: X=Ile or Val
<220> FEATURE:
<221> NAME/KEY: MISC_FEATURE
<222> LOCATION: (169)..(169)
<223> OTHER INFORMATION: X=Ala or Gly
<220> FEATURE:
<221> NAME/KEY: MISC_FEATURE
<222> LOCATION: (170)..(170)
<223> OTHER INFORMATION: X=Ala or Ser
<220> FEATURE:
<221> NAME/KEY: MISC_FEATURE
<222> LOCATION: (173)..(180)
<223> OTHER INFORMATION: X=any amino acid
<220> FEATURE:
<221> NAME/KEY: MISC_FEATURE
<222> LOCATION: (182)..(182)
<223> OTHER INFORMATION: X=any amino acid
<220> FEATURE:
<221> NAME/KEY: MISC_FEATURE
<222> LOCATION: (183)..(183)
<223> OTHER INFORMATION: X=Phe or Leu
<220> FEATURE:
<221> NAME/KEY: MISC_FEATURE
<222> LOCATION: (184)..(184)
<223> OTHER INFORMATION: X=any amino acid
<220> FEATURE:
```

<220> FEATURE:
<221> NAME/KEY: MISC_FEATURE
<222> LOCATION: (188)..(192)
<223> OTHER INFORMATION: X=any amino acid

<400> SEQUENCE: 45

Pro Xaa Xaa Xaa Xaa Met Xaa Xaa Xaa Xaa Xaa Xaa Xaa Xaa Xaa
1               5                   10                  15

Ala Xaa Xaa Val Xaa Xaa Xaa Gly Gly Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Thr Xaa Xaa Pro Phe Xaa Val Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Pro Xaa Xaa Xaa Gly Gly Xaa Xaa Xaa Xaa
                165                 170                 175

Xaa Xaa Xaa Xaa Ala Xaa Xaa Xaa Leu Gly Ala Xaa Xaa Xaa Xaa
            180                 185                 190

Gly Thr Arg
        195

<210> SEQ ID NO 46
<211> LENGTH: 60
<212> TYPE: PRT
<213> ORGANISM: Unknown
<220> FEATURE:
<223> OTHER INFORMATION: Description of Unknown Organism: A FabK
      Consensus Sequence
<220> FEATURE:
<221> NAME/KEY: MISC_FEATURE
<222> LOCATION: (2)..(2)
<223> OTHER INFORMATION: X=Ile or Val
<220> FEATURE:
<221> NAME/KEY: MISC_FEATURE
<222> LOCATION: (3)..(4)
<223> OTHER INFORMATION: X=any amino acid
<220> FEATURE:
<221> NAME/KEY: MISC_FEATURE
<222> LOCATION: (5)..(5)
<223> OTHER INFORMATION: X=Gly or Ala
<220> FEATURE:
<221> NAME/KEY: MISC_FEATURE
<222> LOCATION: (6)..(6)
<223> OTHER INFORMATION: X=Gly or Pro
<220> FEATURE:
<221> NAME/KEY: MISC_FEATURE
<222> LOCATION: (8)..(16)
<223> OTHER INFORMATION: X=any amino acid and up to 3 may be absent
<220> FEATURE:
<221> NAME/KEY: MISC_FEATURE
<222> LOCATION: (18)..(19)
<223> OTHER INFORMATION: X=Pro, Ala, Gly, Ser, or Thr
<220> FEATURE:
<221> NAME/KEY: MISC_FEATURE

```
<222> LOCATION: (21)..(21)
<223> OTHER INFORMATION: X=Ser or Ala
<220> FEATURE:
<221> NAME/KEY: MISC_FEATURE
<222> LOCATION: (22)..(23)
<223> OTHER INFORMATION: X=any amino acid
<220> FEATURE:
<221> NAME/KEY: MISC_FEATURE
<222> LOCATION: (26)..(53)
<223> OTHER INFORMATION: X=any amino acid and up to 6 may be absent
<220> FEATURE:
<221> NAME/KEY: MISC_FEATURE
<222> LOCATION: (55)..(55)
<223> OTHER INFORMATION: X=Gln, Asn, Glu, or Asp
<220> FEATURE:
<221> NAME/KEY: MISC_FEATURE
<222> LOCATION: (56)..(56)
<223> OTHER INFORMATION: X=any amino acid
<220> FEATURE:
<221> NAME/KEY: MISC_FEATURE
<222> LOCATION: (59)..(59)
<223> OTHER INFORMATION: X=Gly or Ala

<400> SEQUENCE: 46

Pro Xaa Xaa Xaa Xaa Met Xaa Xaa Xaa Xaa Xaa Xaa Xaa Xaa Xaa
1               5                   10                  15

Ala Xaa Xaa Val Xaa Xaa Xaa Gly Gly Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Thr Xaa Xaa Pro Phe Xaa Val
    50                  55                  60

<210> SEQ ID NO 47
<211> LENGTH: 1167
<212> TYPE: DNA
<213> ORGANISM: Staphylococcus aureus NCTC 8325

<400> SEQUENCE: 47
atgagatgga taaaaggaa aagaaaaac tttctcaaca gcaaattcaa tttcaacaac        60
ggaaaaatcg caacgtatct atataaggag cgaacagcta tgtggaataa gaatcgactt    120
actcaaatgt taagtattga atatccaatt attacagcag gtttggcagg aagtacgacc    180
cccaaattag ttgcattaat taataacagt ggtgggttag gcacaatagg cgcaggttac    240
tttaatacgc agcaattgga agatgaaata gattatgtac gccaattaac gtcaaattct    300
tttggcgtaa atgtctttgt accaagtcaa caatcatata ccagtagtca aattgaaaat    360
atgaatgcat ggttaaaacc ttatcgacgc gcattacatt tagaagagcc ggttgtaaaa    420
attaccgaag aacaacaatt taagtgtcat attgatacga taattaaaaa gcaagtgcct    480
gtatgttgtt ttacttttgg aattccaagc gaacagatta taagcaggtt gaaagcagcg    540
aatgtcaaac ttataggtac agcaacaagt gttgatgaag ctattgcgaa tgaaaaagcg    600
ggtatggatg ctatcgttgc tcaaggtagt gaagcaggtg acatcgtgg ttcatttta     660 aaacctaaaa atcaattacc tatggttgga acaatatctt tagtgccaca aattgtagat    720
gtcgtttcaa ttccggtcat tgccgctggt ggaattatgg atggtagagg agttttggca    780
agtattgtct taggtgcaga aggggtacaa atgggcaccg catttttaac atcacaagac    840
agtaatgcat cagaactact gcgagatgca attataaata gtaaagaaac agatacagtc    900
attacaaaag cgtttagtgg aaagcttgca cgcggtatca acataggtt tatcgaagaa    960 atgtcccaat acgaaggcga tatcccagat tatccaatac aaaatgagct aacaagtagc   1020
```

-continued

```
ataagaaaag ccgcagcaaa catcggcgac aaagagttaa tacatatgtg gagtggacaa    1080
agcccgcgac tagcaacaac gcatcccgcc aacaccatca tgtccaatat aatcaatcaa    1140
attaatcaaa tcatgcaata taaataa                                         1167
```

<210> SEQ ID NO 48
<211> LENGTH: 355
<212> TYPE: PRT
<213> ORGANISM: Staphylococcus aureus NCTC 8325

<400> SEQUENCE: 48

```
Met Trp Asn Lys Asn Arg Leu Thr Gln Met Leu Ser Ile Glu Tyr Pro
1               5                   10                  15

Ile Ile Thr Ala Gly Leu Ala Gly Ser Thr Thr Pro Lys Leu Val Ala
            20                  25                  30

Leu Ile Asn Asn Ser Gly Gly Leu Gly Thr Ile Gly Ala Gly Tyr Phe
        35                  40                  45

Asn Thr Gln Gln Leu Glu Asp Glu Ile Asp Tyr Val Arg Gln Leu Thr
    50                  55                  60

Ser Asn Ser Phe Gly Val Asn Val Phe Val Pro Ser Gln Gln Ser Tyr
65                  70                  75                  80

Thr Ser Ser Gln Ile Glu Asn Met Asn Ala Trp Leu Lys Pro Tyr Arg
                85                  90                  95

Arg Ala Leu His Leu Glu Glu Pro Val Val Lys Ile Thr Glu Glu Gln
            100                 105                 110

Gln Phe Lys Cys His Ile Asp Thr Ile Ile Lys Lys Gln Val Pro Val
        115                 120                 125

Cys Cys Phe Thr Phe Gly Ile Pro Ser Glu Gln Ile Ile Ser Arg Leu
130                 135                 140

Lys Ala Ala Asn Val Lys Leu Ile Gly Thr Ala Thr Ser Val Asp Glu
145                 150                 155                 160

Ala Ile Ala Asn Glu Lys Ala Gly Met Asp Ala Ile Val Ala Gln Gly
                165                 170                 175

Ser Glu Ala Gly Gly His Arg Gly Ser Phe Leu Lys Pro Lys Asn Gln
            180                 185                 190

Leu Pro Met Val Gly Thr Ile Ser Leu Val Pro Gln Ile Val Asp Val
        195                 200                 205

Val Ser Ile Pro Val Ile Ala Ala Gly Gly Ile Met Asp Gly Arg Gly
    210                 215                 220

Val Leu Ala Ser Ile Val Leu Gly Ala Glu Gly Val Gln Met Gly Thr
225                 230                 235                 240

Ala Phe Leu Thr Ser Gln Asp Ser Asn Ala Ser Glu Leu Leu Arg Asp
                245                 250                 255

Ala Ile Ile Asn Ser Lys Glu Thr Asp Thr Val Ile Thr Lys Ala Phe
            260                 265                 270

Ser Gly Lys Leu Ala Arg Gly Ile Asn Asn Arg Phe Ile Glu Glu Met
        275                 280                 285

Ser Gln Tyr Glu Gly Asp Ile Pro Asp Tyr Pro Ile Gln Asn Glu Leu
    290                 295                 300

Thr Ser Ser Ile Arg Lys Ala Ala Ala Asn Ile Gly Asp Lys Glu Leu
305                 310                 315                 320

Ile His Met Trp Ser Gly Gln Ser Pro Arg Leu Ala Thr Thr His Pro
                325                 330                 335

Ala Asn Thr Ile Met Ser Asn Ile Ile Asn Gln Ile Asn Gln Ile Met
            340                 345                 350
```

Gln Tyr Lys
     355

<210> SEQ ID NO 49
<211> LENGTH: 753
<212> TYPE: DNA
<213> ORGANISM: FabI Bacillus subtilis

<400> SEQUENCE: 49

| | | | | | |
|---|---|---|---|---|---|
| atggaacaaa | ataaatgtgc | actcgtaaca | ggaagcagcc | gcggtgtcgg | aaaagcggcc | 60 |
| gcgatcagac | ttgctgagaa | cggctataac | atcgtcatta | actatgcacg | cagcaaaaaa | 120 |
| gcagcattag | aaacagcgga | agaaatcgaa | aagcttggcg | ttaaagtgct | tgtcgtaaaa | 180 |
| gcaaacgtag | gacagcctgc | aaaaatcaaa | gaaatgtttc | agcaaattga | tgaaacgttc | 240 |
| ggcagacttg | atgtttttgt | caataatgcc | gcttcaggag | tactaagacc | tgtcatggaa | 300 |
| ttagaagaaa | cacactggga | ctggacgatg | aacattaatg | cgaaagcatt | gcttttctgc | 360 |
| gctcaggaag | ctgccaagct | aatggagaag | aacggtggcg | ggcatattgt | cagcattagt | 420 |
| tcattaggct | ctatccgcta | tcttgaaaac | tacaccacgg | tcggtgtatc | aaaagcagcg | 480 |
| ttagaggctt | taacccgtta | tcttgccgtt | gagctttcac | caaaacaaat | tatcgtcaat | 540 |
| gctgtttcag | gcggagcgat | cgacacagat | gcgctgaagc | acttcccgaa | tagagaagat | 600 |
| ctgcttgagg | atgcgcgcca | aaatacgccg | gcgggacgca | tggtcgaaat | taagacatg | 660 |
| gttgatactg | tggagtttct | agtgtcttcc | aaggctgaca | tgatccgcgg | acagacaatt | 720 |
| atcgttgacg | gcggacgctc | actgctcgtt | taa | | | 753 |

<210> SEQ ID NO 50
<211> LENGTH: 250
<212> TYPE: PRT
<213> ORGANISM: FabI Bacillus subtilis

<400> SEQUENCE: 50

Met Glu Gln Asn Lys Cys Ala Leu Val Thr Gly Ser Ser Arg Gly Val
1               5                   10                  15

Gly Lys Ala Ala Ala Ile Arg Leu Ala Glu Asn Gly Tyr Asn Ile Val
            20                  25                  30

Ile Asn Tyr Ala Arg Ser Lys Lys Ala Ala Leu Glu Thr Ala Glu Glu
        35                  40                  45

Ile Glu Lys Leu Gly Val Lys Val Leu Val Val Lys Ala Asn Val Gly
    50                  55                  60

Gln Pro Ala Lys Ile Lys Glu Met Phe Gln Gln Ile Asp Glu Thr Phe
65                  70                  75                  80

Gly Arg Leu Asp Val Phe Val Asn Asn Ala Ala Ser Gly Val Leu Arg
                85                  90                  95

Pro Val Met Glu Leu Glu Glu Thr His Trp Asp Trp Thr Met Asn Ile
            100                 105                 110

Asn Ala Lys Ala Leu Leu Phe Cys Ala Gln Glu Ala Ala Lys Leu Met
        115                 120                 125

Glu Lys Asn Gly Gly Gly His Ile Val Ser Ile Ser Ser Leu Gly Ser
    130                 135                 140

Ile Arg Tyr Leu Glu Asn Tyr Thr Thr Val Gly Val Ser Lys Ala Ala
145                 150                 155                 160

Leu Glu Ala Leu Thr Arg Tyr Leu Ala Val Glu Leu Ser Pro Lys Gln
                165                 170                 175

```
Ile Ile Val Asn Ala Val Ser Gly Gly Ala Ile Asp Thr Asp Ala Leu
            180                 185                 190

Lys His Phe Pro Asn Arg Glu Asp Leu Leu Glu Asp Ala Arg Gln Asn
            195                 200                 205

Thr Pro Ala Gly Arg Met Val Glu Ile Lys Asp Met Val Asp Thr Val
            210                 215                 220

Glu Phe Leu Val Ser Ser Lys Ala Asp Met Ile Arg Gly Gln Thr Ile
225                 230                 235                 240

Ile Val Asp Gly Gly Arg Ser Leu Leu Val
                245                 250

<210> SEQ ID NO 51
<211> LENGTH: 780
<212> TYPE: DNA
<213> ORGANISM: Campylobacter jejuni NCTC 11168 FabI

<400> SEQUENCE: 51
atgaatacag aatttcaagg aaaaacttta gtgattagcg gtggaactcg cgggataggc      60
aaagctatag tttatgaatt tgctaaagtg ggtgcaaata tagcttttac ttataattct     120
aatgcgcaaa ttgctgatga aatggttcaa gatttggaga aaattataa atcaaagct      180
agagcttatg aatttaatat cttagaacct gaaacctata agaacttttt tgaaaaaatt     240
gatgtggatt ttgatagagt ggattatttt atctcaaatg ctatcatttc aggacgtgcg     300
gttgtaggtg gctataccaa atttatgaag ttaaaaccaa agggaattaa taacattttt     360
acagccacag taaatgcttt tgttgtgggc gcacaagaag cagctaaaag gatggaaaaa     420
gtaggggtg gaagcattat ttctatctca tctacaggaa atttagtgta tatagaaaat      480
tattcaggtc acggtacagc aaaagccgct gtagaagcta tggcaagata tgcggctact     540
gaacttggag aaaaaaatat ccgtgtaaat gtcgtaagtg gtgggcctat taaaactgat     600
gctttaagag cttttacaaa ttatgaagaa gtaaaacagg ctactataaa tttaagccct     660
ttaaatcgca tggggcagcc tgaagatttg gctggagcat gtcttttttct ttgttcaagt     720
aaggcaagtt gggttacagg acatactttc atcgttgatg gtggtacaac ttttaaataa     780

<210> SEQ ID NO 52
<211> LENGTH: 259
<212> TYPE: PRT
<213> ORGANISM: Campylobacter jejuni FabI

<400> SEQUENCE: 52

Met Asn Thr Glu Phe Gln Gly Lys Thr Leu Val Ile Ser Gly Gly Thr
1               5                   10                  15

Arg Gly Ile Gly Lys Ala Ile Val Tyr Glu Phe Ala Lys Val Gly Ala
            20                  25                  30

Asn Ile Ala Phe Thr Tyr Asn Ser Asn Ala Gln Ile Ala Asp Glu Met
            35                  40                  45

Val Gln Asp Leu Glu Lys Asn Tyr Lys Ile Lys Ala Arg Ala Tyr Glu
        50                  55                  60

Phe Asn Ile Leu Glu Pro Glu Thr Tyr Lys Glu Leu Phe Glu Lys Ile
65                  70                  75                  80

Asp Val Asp Phe Asp Arg Val Asp Tyr Phe Ile Ser Asn Ala Ile Ile
                85                  90                  95

Ser Gly Arg Ala Val Val Gly Gly Tyr Thr Lys Phe Met Lys Leu Lys
            100                 105                 110

Pro Lys Gly Ile Asn Asn Ile Phe Thr Ala Thr Val Asn Ala Phe Val
```

```
                    115                 120                     125
Val Gly Ala Gln Glu Ala Ala Lys Arg Met Glu Lys Val Gly Gly
        130                 135                 140

Ser Ile Ile Ser Ile Ser Ser Thr Gly Asn Leu Val Tyr Ile Glu Asn
145                 150                 155                 160

Tyr Ser Gly His Gly Thr Ala Lys Ala Ala Val Glu Ala Met Ala Arg
                165                 170                 175

Tyr Ala Ala Thr Glu Leu Gly Glu Lys Asn Ile Arg Val Asn Val Val
                180                 185                 190

Ser Gly Gly Pro Ile Lys Thr Asp Ala Leu Arg Ala Phe Thr Asn Tyr
                195                 200                 205

Glu Glu Val Lys Gln Ala Thr Ile Asn Leu Ser Pro Leu Asn Arg Met
        210                 215                 220

Gly Gln Pro Glu Asp Leu Ala Gly Ala Cys Leu Phe Leu Cys Ser Ser
225                 230                 235                 240

Lys Ala Ser Trp Val Thr Gly His Thr Phe Ile Val Asp Gly Thr
                245                 250                 255

Thr Phe Lys
```

<210> SEQ ID NO 53
<211> LENGTH: 789
<212> TYPE: DNA
<213> ORGANISM: Helicobacter pylori FabI

<400> SEQUENCE: 53

```
atgaatggtt ccaatcacat gaaaaataaa accctagtga tcagcggcgc gactagaggg      60
attggcaagg cgatatttgt acgcttcgct caaagcggcg tgaatatcgc tttcacttac    120
aataaaaatg ttgaagaagc aacaaaatc atagaagatg tggagcaaaa atattccatt    180
aaagccaaag cctactctct taatgtttta gagcctgagc aatacacgga cttttcaag    240
caaattgacg ctgattttga cagagtggat tttttttattt ctaacgctat tatttatggg    300
cgttctgtcg tgggggatt tgcaccgttt atgcgattaa aacctaaggg gttaaacaac    360
atttacacag ccaccgtgtt agcgttcgtc gtagggctc aagaagcggc aaaacgcatg    420
caaaaaatag gcgtgggc gatcgtgagc ttaagttcta ccgggaatct agtttatatg    480
cctaattacg ccgggcatgg caattccaaa aacgccgtag aaaccatggt caaatacgct    540
gccgtggatt taggcgaatt taacattaga gtgaatgcgg ttagtggcgg gcctattgat    600
acggacgctt tgaaagcctt ccctgattat gtggagatta agaaaaagt agaagagcaa    660
tcgccctaa aacgcatggg caatcctaac gatctagccg gagcggctta ttttttatgc    720
gatgagaccc aaagcggttg gcttacaggg caaacgatcg ttgtagatgg cgggactact    780
tttaaataa                                                            789
```

<210> SEQ ID NO 54
<211> LENGTH: 262
<212> TYPE: PRT
<213> ORGANISM: Helicobacter pylori FabI

<400> SEQUENCE: 54

```
Met Asn Gly Ser Asn His Met Lys Asn Lys Thr Leu Val Ile Ser Gly
1                 5                   10                  15

Ala Thr Arg Gly Ile Gly Lys Ala Ile Phe Val Arg Phe Ala Gln Ser
                20                  25                  30

Gly Val Asn Ile Ala Phe Thr Tyr Asn Lys Asn Val Glu Glu Ala Asn
```

```
                35                  40                  45
Lys Ile Ile Glu Asp Val Glu Gln Lys Tyr Ser Ile Lys Ala Lys Ala
             50                  55                  60

Tyr Ser Leu Asn Val Leu Glu Pro Glu Gln Tyr Thr Glu Leu Phe Lys
 65                  70                  75                  80

Gln Ile Asp Ala Asp Phe Asp Arg Val Asp Phe Phe Ile Ser Asn Ala
                 85                  90                  95

Ile Ile Tyr Gly Arg Ser Val Val Gly Phe Ala Pro Phe Met Arg
            100                 105                 110

Leu Lys Pro Lys Gly Leu Asn Asn Ile Tyr Thr Ala Thr Val Leu Ala
            115                 120                 125

Phe Val Val Gly Ala Gln Glu Ala Ala Lys Arg Met Gln Lys Ile Gly
130                 135                 140

Gly Gly Ala Ile Val Ser Leu Ser Ser Thr Gly Asn Leu Val Tyr Met
145                 150                 155                 160

Pro Asn Tyr Ala Gly His Gly Asn Ser Lys Asn Ala Val Glu Thr Met
                165                 170                 175

Val Lys Tyr Ala Ala Val Asp Leu Gly Glu Phe Asn Ile Arg Val Asn
            180                 185                 190

Ala Val Ser Gly Gly Pro Ile Asp Thr Asp Ala Leu Lys Ala Phe Pro
            195                 200                 205

Asp Tyr Val Glu Ile Lys Glu Lys Val Glu Glu Gln Ser Pro Leu Lys
            210                 215                 220

Arg Met Gly Asn Pro Asn Asp Leu Ala Gly Ala Ala Tyr Phe Leu Cys
225                 230                 235                 240

Asp Glu Thr Gln Ser Gly Trp Leu Thr Gly Gln Thr Ile Val Val Asp
                245                 250                 255

Gly Gly Thr Thr Phe Lys
            260

<210> SEQ ID NO 55
<211> LENGTH: 843
<212> TYPE: DNA
<213> ORGANISM: FabI Streptomyces collinus

<400> SEQUENCE: 55
atgaacagcc ctcaccagca gcagaccgcc gaccgccggc aggtctccct gatcaccggg      60
gcctcgcgcg gcatcggccg caccctggcc ctcaccctcg cccgccgggg tggcaccgtg     120
gtcgtcaact acaagaagaa cgccgacctg cacagaagac cgtcgccga ggtcgaggag     180 gccggtggcc agggcttcgc ggtccaggcg gacgtcgaga ccaccgaggg ggtcacggcg     240
ctgttcgacg aggtggcgca gcgctgcggg aggctcgatc acttcgtctc caacgcggcg     300
gcgagcgcgt tcaagaacat cgtcgatctc ggcccgcacc acctggaccg ctcgtacgcg     360
atgaacctgc ggcccttcgt gctggggcg caacaggccg tgaagctgat ggacaacggc     420
ggacggatcg tcgcgctgtc ctcctacggc tcggtccgcg cctacccac ctacgcgatg     480 ctcggcggca tgaaagccgc catcgagtca tgggtgcggt acatggcggt ggagttcgct     540
ccttacggca tcaacgtcaa cgcggtcaac ggcggcctga tcgactccga ttcgctggag     600
ttcttctaca acgtcgaggg catgccgccc atgcagggcg tcctcgaccg catcccgcg     660 cgccgtccgg gcaccgtaca ggagatggc gacaccatcg ccttcctgct cggcgacgga     720
gcgggttaca tcaccgggca gaccctcgtg gtcgacggcg ggctcagcat cgtcgcgccg     780
ccgttcttcg cggacgcggg tgaggcgctc gagctgccgc ccggccgac gcgagacgcc     840
``` tga                                                                                                            843

<210> SEQ ID NO 56
<211> LENGTH: 280
<212> TYPE: PRT
<213> ORGANISM: FabI Streptomyces collinus

<400> SEQUENCE: 56

Met Asn Ser Pro His Gln Gln Thr Ala Asp Arg Arg Gln Val Ser
1               5                   10                  15

Leu Ile Thr Gly Ala Ser Arg Gly Ile Gly Arg Thr Leu Ala Leu Thr
                20                  25                  30

Leu Ala Arg Arg Gly Gly Thr Val Val Asn Tyr Lys Lys Asn Ala
                35              40                  45

Asp Leu Ala Gln Lys Thr Val Ala Glu Val Glu Ala Gly Gly Gln
        50                  55                  60

Gly Phe Ala Val Gln Ala Asp Val Glu Thr Thr Gly Val Thr Ala
65                  70                  75                  80

Leu Phe Asp Glu Val Ala Gln Arg Cys Gly Arg Leu Asp His Phe Val
                85                  90                  95

Ser Asn Ala Ala Ala Ser Ala Phe Lys Asn Ile Val Asp Leu Gly Pro
                100                 105                 110

His His Leu Asp Arg Ser Tyr Ala Met Asn Leu Arg Pro Phe Val Leu
                115                 120                 125

Gly Ala Gln Gln Ala Val Lys Leu Met Asp Asn Gly Gly Arg Ile Val
        130                 135                 140

Ala Leu Ser Ser Tyr Gly Ser Val Arg Ala Tyr Pro Thr Tyr Ala Met
145                 150                 155                 160

Leu Gly Gly Met Lys Ala Ala Ile Glu Ser Trp Val Arg Tyr Met Ala
                165                 170                 175

Val Glu Phe Ala Pro Tyr Gly Ile Asn Val Asn Ala Val Asn Gly Gly
                180                 185                 190

Leu Ile Asp Ser Asp Ser Leu Glu Phe Phe Tyr Asn Val Glu Gly Met
                195                 200                 205

Pro Pro Met Gln Gly Val Leu Asp Arg Ile Pro Ala Arg Arg Pro Gly
        210                 215                 220

Thr Val Gln Glu Met Ala Asp Thr Ile Ala Phe Leu Leu Gly Asp Gly
225                 230                 235                 240

Ala Gly Tyr Ile Thr Gly Gln Thr Leu Val Val Asp Gly Gly Leu Ser
                245                 250                 255

Ile Val Ala Pro Pro Phe Phe Ala Asp Ala Gly Glu Ala Leu Glu Leu
                260                 265                 270

Pro Pro Arg Pro Thr Arg Asp Ala
        275                 280

<210> SEQ ID NO 57
<211> LENGTH: 176
<212> TYPE: PRT
<213> ORGANISM: Unknown
<220> FEATURE:
<223> OTHER INFORMATION: Description of Unknown Organism: A FabI
      Consensus Sequence
<220> FEATURE:
<221> NAME/KEY: MISC_FEATURE
<222> LOCATION: (2)..(2)
<223> OTHER INFORMATION: X=Ala, Gly, Ser, Pro, or Thr
<220> FEATURE:
<221> NAME/KEY: MISC_FEATURE

```
<222> LOCATION: (3)..(3)
<223> OTHER INFORMATION: X=Pro, Ala, Gly, Thr, or Ser
<220> FEATURE:
<221> NAME/KEY: MISC_FEATURE
<222> LOCATION: (6)..(6)
<223> OTHER INFORMATION: X=Ile, Val, Leu, or Met
<220> FEATURE:
<221> NAME/KEY: MISC_FEATURE
<222> LOCATION: (8)..(127)
<223> OTHER INFORMATION: X=any amino acid and up to 20 may be absent
<220> FEATURE:
<221> NAME/KEY: MISC_FEATURE
<222> LOCATION: (130)..(130)
<223> OTHER INFORMATION: X=Glu, Gln, Asn, or Asp
<220> FEATURE:
<221> NAME/KEY: MISC_FEATURE
<222> LOCATION: (132)..(132)
<223> OTHER INFORMATION: X=any amino acid
<220> FEATURE:
<221> NAME/KEY: MISC_FEATURE
<222> LOCATION: (134)..(134)
<223> OTHER INFORMATION: X=any amino acid
<220> FEATURE:
<221> NAME/KEY: MISC_FEATURE
<222> LOCATION: (136)..(159)
<223> OTHER INFORMATION: X=any amino acid and up to 6 may be absent
<220> FEATURE:
<221> NAME/KEY: MISC_FEATURE
<222> LOCATION: (161)..(166)
<223> OTHER INFORMATION: X=any amino acid
<220> FEATURE:
<221> NAME/KEY: MISC_FEATURE
<222> LOCATION: (168)..(168)
<223> OTHER INFORMATION: X=any amino acid
<220> FEATURE:
<221> NAME/KEY: MISC_FEATURE
<222> LOCATION: (170)..(170)
<223> OTHER INFORMATION: X=Val, Ile, Leu, or Met
<220> FEATURE:
<221> NAME/KEY: MISC_FEATURE
<222> LOCATION: (172)..(172)
<223> OTHER INFORMATION: X=Thr, Ala, Ser, Pro, or Gly
<220> FEATURE:
<221> NAME/KEY: MISC_FEATURE
<222> LOCATION: (173)..(174)
<223> OTHER INFORMATION: X=any amino acid
<220> FEATURE:
<221> NAME/KEY: MISC_FEATURE
<222> LOCATION: (175)..(175)
<223> OTHER INFORMATION: X=Lys, Arg, or His

<400> SEQUENCE: 57

Gly Xaa Xaa Arg Gly Xaa Gly Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Ala
        115                 120                 125

Gln Xaa Ala Xaa Lys Xaa Met Xaa Xaa Xaa Xaa Xaa Xaa Xaa Xaa
130                 135                 140
```

```
Xaa Xaa Xaa Xaa Xaa Xaa Xaa Xaa Xaa Xaa Xaa Xaa Xaa Xaa Tyr
145                 150                 155                 160

Xaa Xaa Xaa Xaa Xaa Xaa Lys Xaa Ala Xaa Glu Xaa Xaa Xaa Xaa Tyr
                165                 170                 175
```

<210> SEQ ID NO 58
<211> LENGTH: 8
<212> TYPE: PRT
<213> ORGANISM: Unknown
<220> FEATURE:
<223> OTHER INFORMATION: Description of Unknown Organism: A FabI
      Consensus Sequence
<220> FEATURE:
<221> NAME/KEY: MISC_FEATURE
<222> LOCATION: (2)..(2)
<223> OTHER INFORMATION: X=Ala, Gly, Ser, Pro, or Thr
<220> FEATURE:
<221> NAME/KEY: MISC_FEATURE
<222> LOCATION: (3)..(3)
<223> OTHER INFORMATION: X=Pro, Ala, Gly, Thr, or Ser
<220> FEATURE:
<221> NAME/KEY: MISC_FEATURE
<222> LOCATION: (6)..(6)
<223> OTHER INFORMATION: X=Ile, Val, Leu, or Met
<220> FEATURE:
<221> NAME/KEY: MISC_FEATURE
<222> LOCATION: (8)..(8)
<223> OTHER INFORMATION: X=any amino acid

<400> SEQUENCE: 58

```
Gly Xaa Xaa Arg Gly Xaa Gly Xaa
1               5
```

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 59
tctagacata tgaaaacgcg tattacagaa tta                              33

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 60
ggatcctaga tactgggcac cttgacc                                     27

<210> SEQ ID NO 61
<211> LENGTH: 5
<212> TYPE: PRT
<213> ORGANISM: Unknown
<220> FEATURE:
<223> OTHER INFORMATION: Description of Unknown Organism: A SDR
      Consensus Sequence
<220> FEATURE:
<221> NAME/KEY: MISC_FEATURE
<222> LOCATION: (2)..(4)
<223> OTHER INFORMATION: X=any amino acid

<400> SEQUENCE: 61

```
Tyr Xaa Xaa Xaa Lys
1               5
```

```
<210> SEQ ID NO 62
<211> LENGTH: 8
<212> TYPE: PRT
<213> ORGANISM: Unknown
<220> FEATURE:
<223> OTHER INFORMATION: Description of Unknown Organism: A Enoyl
      Reductase Consensus Sequence
<220> FEATURE:
<221> NAME/KEY: MISC_FEATURE
<222> LOCATION: (2)..(7)
<223> OTHER INFORMATION: X=any amino acid

<400> SEQUENCE: 62

Thr Xaa Xaa Xaa Xaa Xaa Xaa Lys
1               5
```

ENOYL REDUCTASES AND METHODS OF USE THEREOF

RESEARCH SUPPORT

The research leading to the present invention was supported in part by NIH Grant GM 34496 and Cancer Center CORE Support Grant 21765 from the National Cancer Institute. The government may have certain rights in the present invention. Support for this invention was also provided by the AMERICAN LEBANESE SYRIAN ASSOCIATED CHARITIES.

FIELD OF THE INVENTION

The present invention relates to novel enzymes that act as enoyl reductases. Two distinct families of enoyl reductases have been identified in bacteria, each of which have a consensus amino acid sequence. The enoyl reductases can be used as targets for designing both new prophylactics and treatments for bacterial infections. Nucleic acid and amino acid sequences of the novel enoyl reductases are also provided.

BACKGROUND OF THE INVENTION

Essentially all living organisms synthesize saturated fatty acids by the same biochemical mechanism. However, whereas vertebrates and yeast synthesize saturated fatty acids using either one or two multifunctional enzymes (i.e., type I fatty acid synthases, FASs), with the acyl carrier protein (ACP) being an integral part of the complex, most bacteria and plants synthesize saturated fatty acids through the use of a set of distinct enzymes that are each encoded by an individual gene (i.e., type II FASs). In the type II FAS system, ACP is also a distinct protein.

The initial step in the biosynthetic cycle of saturated fatty acids is performed by the enzyme FabH [Tsay et al., *J. Biol. Chem.* 267:6807–68014 (1992), and U.S. Pat. No: 5,759, 832, Issued Jun. 2, 1998, both of which are hereby incorporated by reference in their entireties] which catalyzes the condensation of malonyl-ACP with acetyl-COA. Malonyl-ACP is condensed with the growing-chain acyl-ACP in subsequent rounds by FabB synthase I or by FabF, synthase II. The next step is a ketoester reduction that is catalyzed by an NADPH-dependent β-ketoacyl-ACP reductase (FabG). A β-hydroxyacyl-ACP dehydrase (FabA, dehydrase I or FabZ, dehydrase II) catalyzes the subsequent dehydration forming trans-2-enoyl-ACP. FabI, an NADH-dependent enoyl-ACP reductase, then catalyzes the conversion of trans-2-enoyl-ACP to acyl-ACP to complete the elongation cycle. The addition of two carbon atoms per elongation cycle continues until palmitoyl-ACP is synthesized. Palmitoyl-ACP is one end-product of the pathway and acts as a feedback inhibitor for both FabH and FabI [Heath, et al, *J.Biol. Chem.* 271:1833–1836 (1996)].

Since an enoyl-ACP reductase catalyzes the final step in the biosynthetic pathway of saturated fatty acids, it is not surprising that it is also a key regulatory target for the pathway [Heath, and Rock, *J.Biol.Chem.* 271:1833–1836 (1996); Heath and Rock, *J.Biol.Chem.* 271:10996–11000 [(1996)]. Thus, pharmaceutical companies have placed considerable effort toward developing drugs that inhibit enoyl-ACP reductases and/or the reactions they catalyze. For example, the enoyl-ACP reductase of *Mycobacterium tuberculosis* (InhA) is a target for the drug isonaizid [Banerjee et al., *Science*, 263:227 (1994)] whereas, both diazaborines [Baldock et al., *Biochem. Phartmacol.*, 55:1541 (1998)] and triclosan [McMurray et al., *Nature* (London), 394:531 (1998) and Heath et al., *J. Biol. Chem.*, 273:30316 (1998)] inhibit the *Escherichia coli* enoyl-ACP reductase, FabI. All three drugs act through the formation of a high-affinity enzyme-NAD$^+$-drug ternary complex [Heath et al., *J. Biol. Chem.*, 274:11110–11114 (1999) and Rozwarski et al., *Science*, 279:98 (1998); Baldock et al., *Science*, 274:2107 (1996); Levy et al., *Nature* (London) 398:383 (1999); Stewart et al, *J. Mol. Biol.*, 290:859 (1999); and Ward et al., *Biochemistry*, 38:12514 (1999)]. Consistently, missense mutations resulting in single arnino acid substitutions in the active sites of the enoyl-ACP reductases prevent the formation of the ternary complexes and confer a resistant phenotype to bacteria expressing the mutant proteins [Banerjee et al., *Science*, 263:227 (1994); McMurray et al., *Nature* (London), 394:531 (1998); Heath et al., *J. Biol. Chem.*, 273:30316 (1998); Heath et al., *J. Biol. Chem.*, 274:11110–11114 (1999); and Bergler et al., *J. Gen. Microbiol.*, 138:2093 (1992) and Rouse et al.,*Antimicrobiol. Agents. Chem.*, 39:2472 (1995)].

Unfortunately, the toxicity of boron severely limits the pharmaceutical application of diazaborines [Baldock et al, *Biochem. Phannacol.*, 55:1541(1998)]. Triclosan, on the other hand, is widely employed as an antibacterial in consumer products for external use. Triclosan is a diphenyl ether (bis-phenyl) derivative, known as either 2,4,4'-Trichloro-2'-hydroxydiphenyl ether or 5-Chloro-2-(2,4-dichlorophenoxy) phenol, and is used as an antibacterial in antimicrobial creams, antiperspirants, body washes, cosmetics, deodorants, deodorant soaps, detergents, dish washing liquids, hand soaps, lotions, and toothpaste, as well as in plastics, polymers and textiles [see, Bhargava and Leonard, *Am. J. Infect. Control*, 24:209 (1996)]. However, the hydrophobic nature and chlorine content of triclosan makes it undesirable for internal use.

Bacterial infections remain among the most common and deadly causes of human disease. For example, Streptococci are known to cause otitis media, conjunctivitis, pneumonia, bacteremia, meningitis, sinusitis, pleural empyema and endocarditis. In addition, virulent strains of *E. coli* can cause severe diarrhea, a condition which worldwide kills a million more people (3 million) every year than malaria [D. Leff, *BIOWORLD TODAY*, 9:1,3 (1998)]. Indeed, infectious diseases are the third leading cause of death in the United States and the leading cause of death worldwide [Binder et al., *Science* 284:1311–1313 (1999)].

Although, there was initial optimism in the middle of the 20th century that diseases caused by bacteria would be quickly eradicated, it has become evident that the so-called "miracle drugs" are not sufficient to accomplish this task. Indeed, antibiotic resistant pathogenic strains of bacteria have become common-place, and bacterial resistance to the new variations of these drugs appears to be outpacing the ability of scientists to develop effective chemical analogs of the existing drugs [See, Stuart B. Levy, *The Challenge of Antibiotic Resistance*, in *Scientific American*, 46–53 (March, 1998)]. Therefore, new approaches to drug development are necessary to combat the ever-increasing number of antibiotic-resistant pathogens.

Classical penicillin-type antibiotics effect a single class of proteins known as autolysins. Therefore, the development of new drugs which effect an alternative bacterial target protein would be desirable. Such a target protein ideally would be indispensable for bacterial survival. Thus the identification of a new bacterial enzyme that is required for fatty acid synthesis would be a prime candidate for such drug development.

Therefore, there is a need to identify new proteins that have enzymatic activities that are crucial for bacterial growth. There is also a need to provide immunogenic compositions containing such enzymes or fragments thereof. In addition, there is a need to develop methods for identifying drugs that interfere with such enzymes. Finally, there is a need to employ such procedures to develop new antibacterial drugs.

The citation of any reference herein should not be construed as an admission that such reference is available as "Prior Art" to the instant application.

SUMMARY OF THE INVENTION

The present invention provides two families of enzymes that can act as enoyl reductases. One such family shares a common amino acid consensus sequence, SEQ ID NO:45 and binds a flavin cofactor. This family of enoyl reductases is exemplified by the *Streptococcus pneumoniae*, FabK having an amino acid sequence of SEQ ID NO:2 and is naturally encoded by SEQ ID NO:1, as disclosed herein. The other family of enoyl reductases shares a common amino acid consensus sequence, SEQ ID NO:57 and like the previously disclosed FabI does not contain a flavin cofactor. This second family of enoyl reductases is exemplified by the *Campylobacter jejuni* FabL having an amino acid sequence of SEQ ID NO:52 and is naturally encoded by SEQ ID NO:51, as disclosed herein.

As disclosed herein and exemplified below, bacteria can express either or both of two unique enoyl reductases, FabK and/or FabL each of which catalyze the identical reaction as the well-characterized Gram-negative bacterial enoyl-ACP reductase, FabI. Since FabI has been a useful target for the design of antibacterials, the identification of FabK and FabL provides another important target. Indeed, the disclosure of FabK and FabL and their related analogs should have a major impact on the development of new prophylactics and treatments for bacterial infections, including those pharmaceuticals that can be used to combat antibiotic resistant Streptococcus and *Enterococcus strains*.

Thus the present invention provides an isolated nucleic acid that encodes a polypeptide comprising the amino acid sequence of SEQ ID NO:45. The present invention further provides an isolated nucleic acid that encodes a polypeptide comprising the amino acid sequence of SEQ ID NO:57. Preferably the polypeptide acts enzymatically as an enoyl reductase. In the case of FabK enoyl reductases, such nucleic acids preferably encode a polypeptide that also binds a flavin prosthetic group. Although the enoyl reductase can be obtained form any source, particularly from fungus, bacteria or plants, in a preferred embodiment the enoyl reductase is not a yeast enzyme. More preferably, the polypeptide is a bacterial enzyme or an active fragment of the bacterial enzyme. The polypeptides encoded by the nucleic acids are also part of the present invention.

In one such embodiment the nucleic acid encodes a bacterial enzyme that comprises an amino acid sequence of SEQ ID NO:2. In another embodiment the nucleic acid encodes a bacterial enzyme that comprises the amino acid sequence of SEQ ID NO:2 comprising a conservative amino acid substitution. In related embodiments, the nucleic acid encodes a bacterial enzyme that comprises the amino acid sequence of SEQ ID NO:4 or the amino acid sequence of SEQ ID NO:4 comprising a conservative amino acid substitution, or the amino acid sequence of SEQ ID NO:6, or the amino acid sequence of SEQ ID NO:6 comprising a conservative amino acid substitution, or the amino acid sequence of SEQ ID NO:10, or the amino acid sequence of SEQ ID NO:10 comprising a conservative amino acid substitution, or the amino acid sequence of SEQ ID NO:12, or the amino acid sequence of SEQ ID NO:12 comprising a conservative amino acid substitution, or the amino acid sequence of SEQ ID NO:14, or the amino acid sequence of SEQ ID NO:14 comprising a conservative amino acid substitution, or the amino acid sequence of SEQ ID NO:16, or the amino acid sequence of SEQ ID NO:16 comprising a conservative amino acid substitution, or the amino acid sequence of SEQ ID NO:18, or the amino acid sequence of SEQ ID NO:18 comprising a conservative amino acid substitution, or the amino acid sequence of SEQ ID NO:20, or the amino acid sequence of SEQ ID NO:20 comprising a conservative amino acid substitution.

In other embodiments the nucleic acid encodes a bacterial enzyme that comprises the amino acid sequence of SEQ ID NO:28 or the amino acid sequence of SEQ ID NO:28 comprising a conservative amino acid substitution, or the amino acid sequence of SEQ ID NO:30, or the amino acid sequence of SEQ ID NO:30 comprising a conservative amino acid substitution, or the amino acid sequence of SEQ ID NO:34, or the amino acid sequence of SEQ ID NO:34 comprising a conservative amino acid substitution, or the amino acid sequence of SEQ ID NO:38, or the amino acid sequence of SEQ ID NO:38 comprising a conservative amino acid substitution. The present invention further provides a nucleic acid encoding a bacterial enzyme that comprises an amino acid sequence of SEQ ID NO:52. In another embodiment the nucleic acid encodes a bacterial enzyme that comprises the amino acid sequence of SEQ ID NO:52 comprising a conservative amino acid substitution. In related embodiments, the nucleic acid encodes a bacterial enzyme that comprises the amino acid sequence of SEQ ID NO:54 or the amino acid sequence of SEQ ID NO:54 comprising a conservative amino acid substitution, or the amino acid sequence of SEQ ID NO:56, or the amino acid sequence of SEQ ID NO:56 comprising a conservative amino acid substitution, or the amino acid sequence of SEQ ID NO:50, or the amino acid sequence of SEQ ID NO:50 comprising a conservative amino acid substitution.

In a particular embodiment the isolated nucleic acid comprises the nucleotide sequence of SEQ ID NO:1. In related embodiments the isolated nucleic acid comprises the nucleotide sequence of SEQ ID NO:3, or the nucleotide sequence of SEQ ID NO:5, or the nucleotide sequence of SEQ ID NO:9, or the nucleotide sequence of SEQ ID NO:1, or the nucleotide sequence of SEQ ID NO:13, or the nucleotide sequence of SEQ ID NO:15, or the nucleotide sequence of SEQ ID NO:17, or the nucleotide sequence of SEQ ID NO:19.

Still other related embodiments comprise the nucleotide sequence of SEQ ID NO:27, or the nucleotide sequence of SEQ ID NO:29, or the nucleotide sequence of SEQ ID NO:33, or the nucleotide sequence of SEQ ID NO:37.

In a particular embodiment the isolated nucleic acid comprises the nucleotide sequence of SEQ ID NO:51. In related embodiments the isolated nucleic acid comprises the nucleotide sequence of SEQ ID NO:53, or the nucleotide sequence of SEQ ID NO:55, or the nucleotide sequence of SEQ ID NO:49.

The polypeptides encoded by all of the novel nucleic acids disclosed above are also part of the present invention.

The present invention also includes an isolated nucleic acid that hybridizes under standard hybridization conditions to a nucleic acid (e.g., a cDNA) comprising one or more of the nucleotide sequences of the present invention. In a preferred embodiment the isolated nucleic acid hybridizes to the nucleotide sequence of SEQ ID NO:1. In another preferred embodiment the isolated nucleic acid hybridizes to the nucleotide sequence of SEQ ID NO:51. In related embodiments, the isolated nucleic acid hybridizes to the nucleotide sequence of SEQ ID NO:3, and/or the nucleotide sequence of SEQ ID NO:5, and/or the nucleotide sequence of SEQ ID NO:9, and/or the nucleotide sequence of SEQ ID NO:11, and/or the nucleotide sequence of SEQ ID NO:13, and/or the nucleotide sequence of SEQ ID NO:15, and/or the nucleotide sequence of SEQ ID NO:17, and/or the nucleotide sequence of SEQ ID NO:19. In still other related embodiments the isolated nucleic acid hybridizes to the nucleotide sequence of the nucleotide sequence of SEQ ID NO:53, and/or the nucleotide sequence of SEQ ID NO:55, and/or the nucleotide sequence of SEQ ID NO:49.

Such nucleic acids include those that can act as probes or primers for one or more of the nucleotide sequences of the present invention. The polypeptides encoded by the novel nucleic acids that hybridize to the nucleic acids described above are also part of the present invention.

The present invention further provides a recombinant DNA molecule that comprises an isolated nucleic acid of the present invention, as described above with or without a heterologous nucleotide sequence. Such a recombinant DNA molecule can be operatively linked to an expression control sequence and can be part of an expression vector. The present invention further provides a cell that comprises such an expression vector. The cell can be either a eukaryotic or preferably a prokaryotic cell. The present invention further provides a method of expressing a recombinant polypeptide of the present invention or fragment thereof in this cell. One such method comprises culturing the cell in an appropriate cell culture medium under conditions that provide for expression of the polypeptide by the cell. Preferably the recombinant polypeptide comprises the amino acid sequence of SEQ ID NO:45, can bind a flavin prosthetic group, and can act enzymatically as an enoyl reductase. In an alternative embodiment the recombinant polypeptide comprises the amino acid sequence of SEQ ID NO:57, does not contain a flavin prosthetic group, and can act enzymatically as an enoyl reductase. In a preferred embodiment the method comprises the step of purifying the recombinant polypeptide. The recombinant polypeptide purified by the method is also part of the present invention.

The present invention further provides a nucleic acid that encodes a polypeptide that binds a flavin prosthetic group, has enoyl reductase activity and has at least 30%, preferably 60%, more preferably 75%, even more preferably 90% and most preferably 95% amino acid identity with a bacterial enzyme comprising the amino acid sequence of SEQ ID NO:2. In a preferred embodiment the nucleic acid encodes a FabK. In related embodiments, the nucleic acid encodes a polypeptide that binds a flavin prosthetic group, has enoyl reductase activity and has at least 60%, preferably 80%, and more preferably 90% amino acid identity with a bacterial enzyme comprising the amino acid sequence of SEQ ID NO:4, and/or the amino acid sequence of SEQ ID NO:6, and/or the amino acid sequence of SEQ ID NO:10, and/or the amino acid sequence of SEQ ID NO:12, and/or the amino acid sequence of SEQ ID NO:14, and/or the amino acid sequence of SEQ ID NO:16, and/or the amino acid sequence of SEQ ID NO:18, and/or the amino acid sequence of SEQ ID NO:20. Again in preferred embodiments the nucleic acid encodes a FabK. The polypeptides encoded by the nucleic acids described above are also part of the present invention.

The present invention also provides a nucleic acid that encodes a polypeptide that does not contain a flavin prosthetic group, has enoyl reductase activity and has at least 40%, preferably 75%, more preferably 85%, even more preferably 90% and most preferably 95% amino acid identity with a bacterial enzyme comprising the amino acid sequence of SEQ ID NO:52. The polypeptides encoded by the nucleic acids described above are also part of the present invention.

The present invention also provides a nucleic acid that encodes a polypeptide that binds a flavin prosthetic group, has enoyl reductase activity and that comprises at least 8, preferably 12 and more preferably 16 consecutive amino acids of a bacterial enzyme that has an amino acid sequence of SEQ ID NO:2. In a preferred embodiment the nucleic acid encodes a FabK. In related embodiments, the nucleic acid encodes a polypeptide that binds a flavin prosthetic group, has enoyl reductase activity and comprises at least 8, preferably 12 and more preferably 16 consecutive amino acids of a bacterial enzyme that has an amino acid sequence of SEQ ID NO:4, and/or the amino acid sequence of SEQ ID NO:6, and/or the amino acid sequence of SEQ ID NO:10, and/or the amino acid sequence of SEQ ID NO:12, and/or the amino acid sequence of SEQ ID NO:14, and/or the amino acid sequence of SEQ ID NO:16, and/or the amino acid sequence of SEQ ID NO:18, and/or the amino acid sequence of SEQ ID NO:20. In preferred embodiments the nucleic acid encodes a FabK. The polypeptides encoded by the nucleic acids described above are also part of the present invention.

The present invention further provides a nucleic acid that encodes a polypeptide that does not contain a flavin prosthetic group, has enoyl reductase activity and that comprises at least 8, preferably 12 and more preferably 16 consecutive amino acids of a bacterial enzyme that has an amino acid sequence of SEQ ID NO:52. In a preferred embodiment the nucleic acid encodes a FabL. In related embodiments, the nucleic acid encodes a polypeptide that does not contain a flavin prosthetic group, has enoyl reductase activity and comprises at least 8, preferably 12 and more preferably 16 consecutive amino acids of a bacterial enzyme that has an amino acid sequence of SEQ ID NO:54, and/or the amino acid sequence of SEQ ID NO:56, and/or the amino acid sequence of SEQ ID NO:50. The polypeptides encoded by the nucleic acids described above are also part of the present invention.

The present invention further provides fragments of the polypeptides of the present invention and fusion proteins/peptides including chimeric proteins and intein fusion proteins/peptides. The fusion proteins/peptides can comprise any of the polypeptides of the present invention including the fragments of the polypeptides. Such fragments include antigenic fragments, proteolytic fragments, such as peptides prepared by treatment with a protease e.g., trypsin, active fragments that retain enoyl reductase activity, and peptides comprising at least 5, preferably 12 and more preferably 20 consecutive amino acids of a bacterial enzyme that has the amino acid sequence of SEQ ID NO:2 and/or the amino acid sequence of SEQ ID NO:4, and/or the amino acid sequence of SEQ ID NO:6, and/or the amino acid sequence of SEQ ID NO:10, and/or the amino acid sequence of SEQ ID NO:12, and/or the amino acid sequence of SEQ ID NO:14, and/or the amino acid sequence of SEQ ID NO:16, and/or the amino acid sequence of SEQ ID NO:18, and/or the amino acid sequence of SEQ ID NO:20. In a particular embodiment, the antigenic fragment comprises the amino acid sequence of SEQ ID NO:46 or SEQ ID NO:46 comprising a conservative amino acid substitution.

In a related embodiment such fragments comprise at least 5, preferably 12 and more preferably 20 consecutive amino acids of a bacterial enzyme that has the amino acid sequence has the amino acid sequence of SEQ ID NO:52 and/or the amino acid sequence of SEQ ID NO:54, and/or the amino acid sequence of SEQ ID NO:56, and/or the amino acid sequence of SEQ ID NO:50. In a particular embodiment, the antigenic fragment comprises the amino acid sequence of SEQ ID NO:58 or SEQ ID NO:58 comprising a conservative amino acid substitution.

The present invention also provides fragments and fusion proteins/peptides as defined above for the enoyl reductases having the amino acid sequence of SEQ ID NO:28, SEQ ID NO:30, SEQ ID NO:34, and SEQ ID NO:38.

In addition, the present invention provides proteins and fragments and fusion proteins/peptides as defined above having the amino acid sequences of SEQ ID NO:8, SEQ ID NO:22, SEQ ID NO:24, SEQ ID NO:32, SEQ ID NO:36 and SEQ ID NO:48.

The present invention also provides immunogenic compositions and vaccines. In a particular embodiment the vaccine comprises an antigenic fragment of the present invention. Antibodies to the enoyl reductases and antigenic fragments of the present invention are also included. Such antibodies can be monoclonal antibodies, and/or chimeric antibodies or polyclonal antibodies. The present invention further provides an immortal cell line that produces a monoclonal antibody of the present invention. In a particular embodiment, the monoclonal antibody is raised against a polypeptide or fragment thereof comprising SEQ ID NO:46. In another embodiment, the monoclonal antibody is raised against a polypeptide or fragment thereof comprising SEQ ID NO:58.

The present invention further provides methods for identifying agents that can modulate the enzymatic activity of an enoyl reductase of the present invention. One such embodiment comprises measuring the enzymatic activity of an enoyl reductase or active fragment thereof in the presence and absence of a compound. The compound is identified as an agent that modulates the enzymatic activity of an enoyl reductase when the enzymatic activity measured is different in the presence of the compound relative to in the absence of the compound. In a preferred embodiment of this type, the enoyl reductase comprises the amino acid sequence of SEQ ID NO:45 and contains a flavin prosthetic group. In another preferred embodiment of this type, the enoyl reductase comprises the amino acid sequence of SEQ ID NO:57 and does not contain a flavin prosthetic group. In a particular embodiment, the enzymatic activity is lower in the presence of the compound relative to in the absence of the compound. In this case the compound is identified as an inhibitor of the enoyl reductase. In another embodiment of this type, the enzymatic activity is higher in the presence of the compound relative to in the absence of the compound. In this case the compound is identified as an agonist of the enoyl reductase. In one particular embodiment, the enoyl reductase is a FabK. In another particular embodiment, the enoyl reductase is a FabL.

The present invention further provides methods for identifying an agent that can bind to an enoyl reductase. One such embodiment comprises contacting an enoyl reductase or active fragment thereof with a compound and determining whether the compound binds to the enoyl reductase. A compound is identified as an agent that can bind the enoyl reductase if the compound binds to the enoyl reductase. In a preferred embodiment of this type, the enoyl reductase comprises the amino acid sequence of SEQ ID NO:45 and contains a flavin prosthetic group. In another preferred embodiment of this type, the enoyl reductase comprises the amino acid sequence of SEQ ID NO:57 and does not contain a flavin prosthetic group.

In the in vitro studies involving the enoyl reductases of the present invention, the enoyl reductase preferably has the amino acid sequence of SEQ ID NO:2. However, in other embodiments of the present invention, the enoyl reductase has the amino acid sequence of SEQ ID NO:2 comprising a conservative amino acid substitution, or the amino acid sequence of SEQ ID NO:4, or the amino acid sequence of SEQ ID NO:4 comprising a conservative amino acid substitution, or the amino acid sequence of SEQ ID NO:6, or the amino acid sequence of SEQ ID NO:6 comprising a conservative amino acid substitution, or the amino acid sequence of SEQ ID NO10, or the amino acid sequence of SEQ ID NO:10 comprising a conservative amino acid substitution, or the amino acid sequence of SEQ ID NO:12, or the amino acid sequence of SEQ ID NO:12 comprising a conservative amino acid substitution, or the amino acid sequence of SEQ ID NO:14, or the amino acid sequence of SEQ ID NO:14 comprising a conservative amino acid substitution, or the amino acid sequence of SEQ ID NO:16, or the amino acid sequence of SEQ ID NO:16 comprising a conservative amino acid substitution, or the amino acid sequence of SEQ ID NO:18, or the amino acid sequence of SEQ ID NO:18 comprising a conservative amino acid substitution, or the amino acid sequence of SEQ ID NO:20, or the amino acid sequence of SEQ ID NO:20 comprising a conservative amino acid substitution SEQ ID NO:22.

Similarly, the enoyl reductase can comprise the amino acid sequence of SEQ ID NO:52. In another embodiment the enoyl reductase comprises the amino acid sequence of SEQ ID NO:52 comprising a conservative amino acid substitution. In related embodiments, the enoyl reductase comprises the amino acid sequence of SEQ ID NO:54 or the amino acid sequence of SEQ ID NO:54 comprising a conservative amino acid substitution, or the amino acid sequence of SEQ ID NO:56, or the amino acid sequence of SEQ ID NO:56 comprising a conservative amino acid substitution, or the amino acid sequence of SEQ ID NO:50, or the amino acid sequence of SEQ ID NO:50 comprising a conservative amino acid substitution.

As mentioned above, fusion proteins/peptides and/or fragments, and preferably active fragments of the enoyl reductases can also be used.

The present invention further provides methods for identifying a drug that inhibits bacterial growth. One such embodiment comprises administering an agent that is suspected of inhibiting an enoyl reductase of the present invention to a bacterial cell and then determining the growth of the cell. An agent that inhibits the growth of the cell relative to the growth in the absence of the agent is identified as a drug that inhibits bacterial growth. In a preferred embodiment of this type, the enoyl reductase comprises the amino acid sequence of SEQ ID NO:45 and contains a flavin prosthetic group. In a more preferred embodiment, the enoyl reductase is a FabK. Alternatively, the enoyl reductase comprises the amino acid sequence of SEQ ID NO:57 and does not contain a flavin prosthetic group. In a more preferred embodiment of this type, the enoyl reductase is a FabL.

As should be readily understood, any of the methods described above can be performed either alone, or in tandem including the combination of two or more of the above-described methods. For example, an agent could be first tested for binding, then tested for inhibiting the enoyl reductase. An agent that both binds the enoyl reductase and inhibits the enoyl reductase activity could then be tested to determine if it also inhibited bacterial cell growth. Further studies could be performed in an animal model to determine if the agent was effective in either preventing or treating a bacterial infection. An agent found to be effective in an animal model could then be used in a clinical study. Thus the present invention further provides the agents and drugs identified by the methods of the present invention and the corresponding pharmaceutical compositions, which can further comprise a pharmaceutically acceptable carrier.

Accordingly, it is a principal object of the present invention to provide novel enoyl reductases. Such enzymes can used as targets in drug discovery including for high throughput screening and/or rational drug design.

It is a further object of the present invention to provide methods of using these enoyl reductases to identify agents that will act against bacterial infections.

It is a further object of the present invention to provide antibacterial agents obtained by the methods of the present invention.

It is a further object of the present invention to provide structural and enzymatic characteristics and properties of the enoyl reductases, including their nucleic acid and amino acid sequences.

It is a further object of the present invention to provide an antibody specific for FabK.

It is a further object of the present invention to provide an antibody specific for FabL.

It is a further object of the present invention to provide an immunogenic composition comprising a FabK, or an antigenic fragment of FabK.

It is a further object of the present invention to provide a vaccine comprising a nucleic acid encoding a FabK or an antigenic fragment of a FabK.

It is a further object of the present invention to provide an immunogenic composition comprising a FabK, or an antigenic fragment of FabL It is a further object of the present invention to provide a vaccine comprising a nucleic acid encoding a FabK or an antigenic fragment of a FabL.

It is a further object of the present invention to provide a method of producing an enoyl reductase of the present invention, including through modification or fragmentation of an enoyl reductase through recombinant technology.

It is a further object of the present invention to provide a method of performing rational drug design with the use of an enoyl reductase of the present invention.

These and other aspects of the present invention will be better appreciated by reference to the following drawings and Detailed Description.

BRIEF DESCRIPTION OF THE DRAWINGS

FIGS. 1A and 1B show the fab gene cluster in *S. pnemoniae* and the predicted FabK protein sequence. FIG. 1A shows the fab gene cluster which was defined using the primary sequence of the *E. coli* proteins required for fatty acid synthesis to search the *S. pneumoniae* genome for homologous proteins in the TIGR database. The genes corresponding to fabH, acpP, fabG, fabD, fabF, FabZ and accABCD were clustered on a 10 kbp fragment. A FabI homolog was not present in the *S. pneumoniae* genome, but there was an unidentified open reading frame within the fab cluster that is designated FabK. FIG. 1B shows the deduced protein sequences of FabK. The predicted FabK protein sequence from *S. pneumoniae* is aligned with the predicted sequences of FabK proteins from a representative group of bacteria. Similar amino acids among all six proteins are boxed based on the following similarity groups:

P, A, G, S, T; Q, N, E, D; H, K, R; C; V, L, I, M; and F, Y, W. The region of the proteins containing a consensus binding site for FAD is indicated.

Figure 2A:
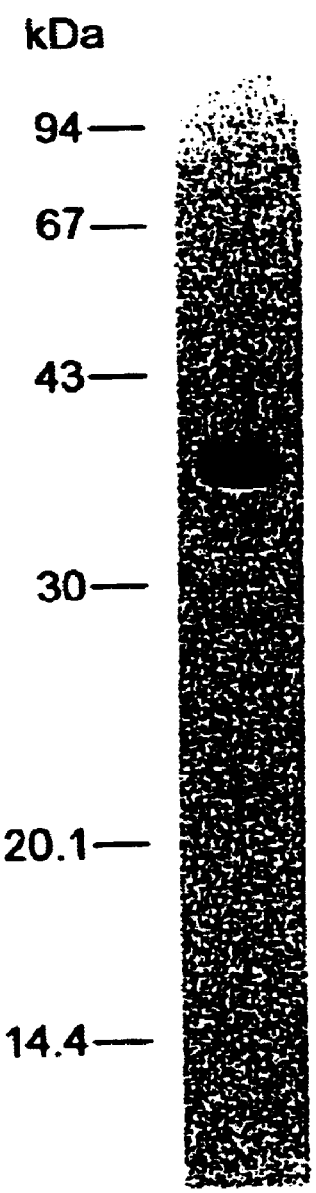
Figure 2B:
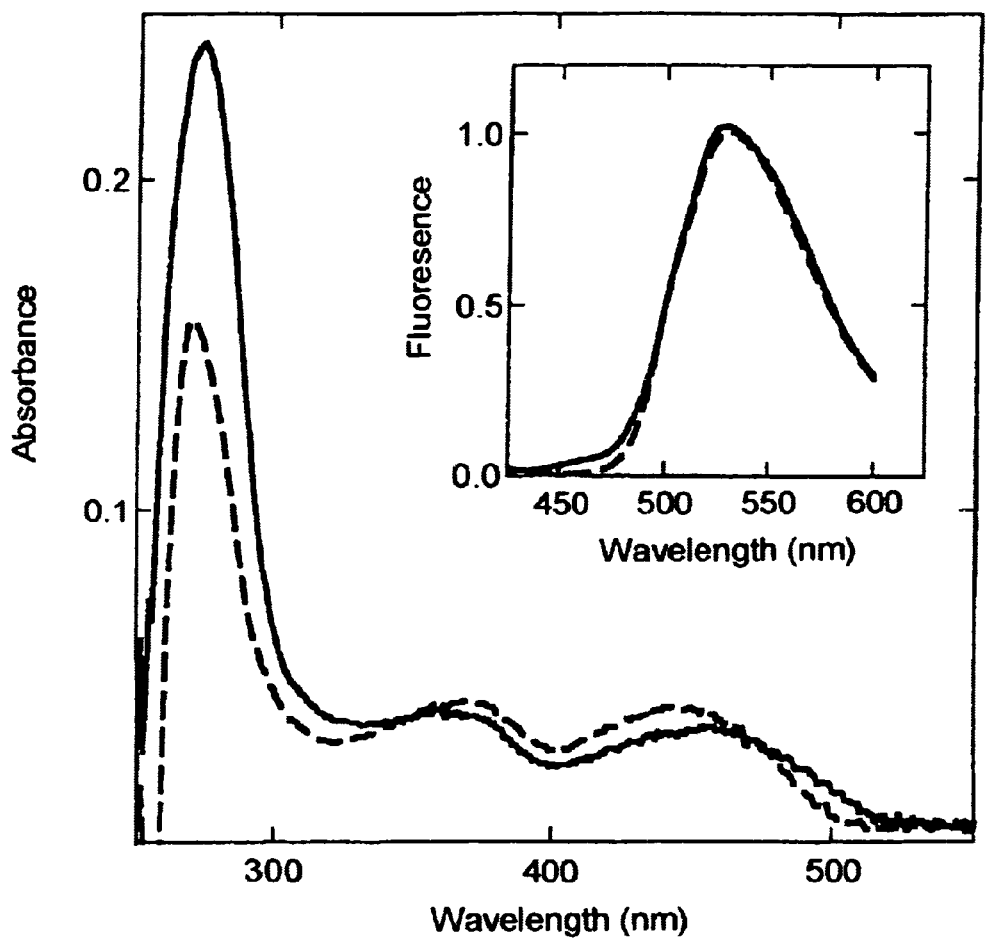
Figure 2C:
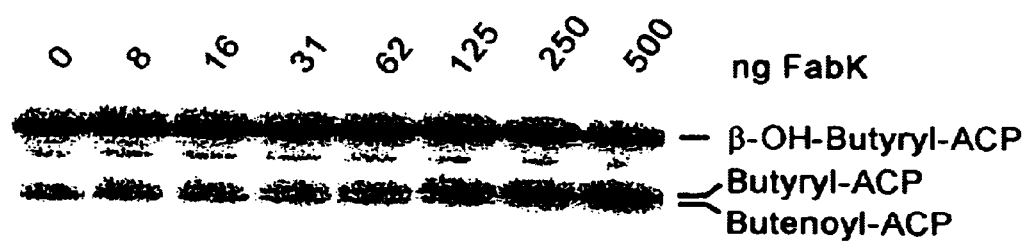
Figure 2D:
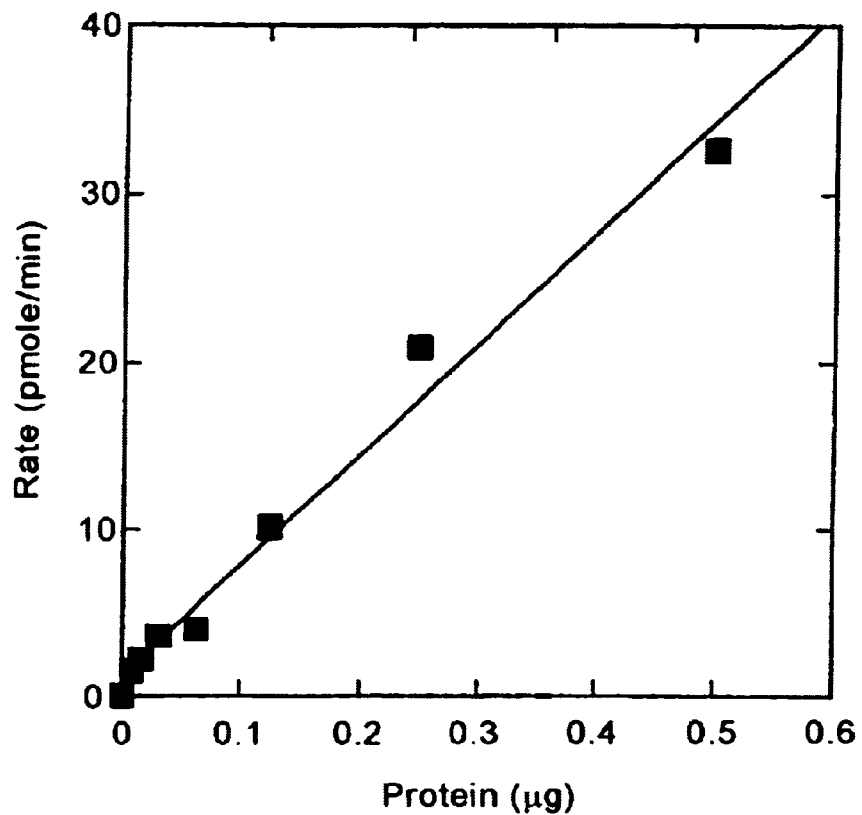

FIGS. 2–2D show the purification and characterization of FabK. FIG. 2A shows a gel with the isolated FabK possessing an amino terminal His-tag. The FabK was expressed in *E. coli* strain BL21-Codon Plus-(DE3)-R1L (Stratagene) grown in LB medium supplemented with riboflavin (0.5 g/L). His-tag FabK was purified by metal chelation affinity chromatography as described in the Example, below. The purified protein migrated at 36 kDa when subjected to SDS gel electrophoresis, corresponding to the predicted molecular weight of the protein plus the His-tag. The purified protein solution was bright yellow, and the UV-Vis spectrum showed absorption maxima at 270, 350 and 450 nm (solid line, FIG. 2B). The absorption at 350 and 450 nm is characteristic of flavin. An aliquot of FabK was boiled for 30 min. The denatured protein that was removed had an FabK:FAD ratio of 0.8 that was calculated using an extinction coefficients of 20.3 at 280 nm for FabK and 11.3 at 450 nm for FAD. Fluoresence spectroscopy (inset, FIG. 2B) of the purified FabK protein (solid line, FIG. 2B) excitated at 417 nm showed an emmission maxima at 535 nm, which was the same as free FAD (dashed line, FIG. 2B). The cofactor was identified as FAD by thin-layer chromatography on silica gel 60 layers developed with 5% $Na_2HPO_4$. A coupled enzyme system was employed to assay FabK by combining the purified *E. coli* proteins required to reconstitute a cycle of fatty acid synthesis with the exception of the FabI enoyl-ACP reductase. Reaction mixtures were first incubated to generate trans-2-butenoyl-ACP and then the indicated amounts of FabK were added as described in the Example below. Products were separated by conformationally sensitive gel electrophoresis and the bands visualized and quantitated using a Phosphorimager (FIG. 2C). FIG. 2D is a plot of the rate of formation of butyryl-ACP as a function of FabK concentration derived from the data in FIG. 2C.

FIG. 3 shows the alignment of two Fab L proteins (from *Bacillus subtilis*, and *Helicobacter pylori*) with FabI from *E. coli*. "+" indicates key residues in *E. coli*. FabI. Similar amino acids among all six proteins are boxed based on the following similarity groups:

P, A, G, S, T; Q, N, E, D; H, K, R; C; V, L, I, M; and F, Y, W.

DETAILED DESCRIPTION OF THE INVENTION

The enoyl-acyl carrier protein (ACP) reductase (FabI) of *Escherichia coli* catalyzes the final step of each round in fatty acid elongation. Because it is essential in bacterial metabolism, it is considered an important the target for anti-bacterials. One such antibacterial is triclosan, which is commonly found in antibacterial hand soaps and related products. The present invention provides a new bacterial enzyme that catalyzes the identical reaction that FabI catalyzes. This new bacterial enzyme has been named FabK. In addition, the present invention provides a number of novel related enzymes that can also act as enoyl reductases.

As disclosed herein, many Gram-positive bacteria express a unique enoyl reductase that has been disclosed herein and named, FabK. One such fabK gene is located within the fatty acid biosynthetic gene cluster of *Streptococcus pneumoniae* and encodes a flavoprotein that catalyzes the NADH-dependent reduction of enoyl-ACPs. FabI is shown herein to be the only target for triclosan in *E. coli* because fabK expression rescues the temperature-sensitive growth phenotype of an *E. coli* fabI(Ts) mutant and confers complete triclosan resistance. In addition, a second unique enoyl reductase has been found as disclosed herein, and is named FabL (see Table 3, below). The discovery of these new enoyl-ACP reductases reveal a unique mechanism for enoyl-ACP reduction that could be exploited for the development of novel antibacterial therapies.

Thus the discovery of two new families of enoyl-ACP reductases both having a significantly different structure from the known FabI proteins has important implications for antibacterial drug development. Since FabK and FabL catalyze the same reaction as FabI, inhibitors of FabK and/or FabL would be an effective bactericide against bacteria and other microorganisms that express FabK and/or FabL rather than FabI. Indeed, microorganisms that express FabK and/or FabL rather than FabI should be refractory to specific FabI inhibitors. Conversely, the development of selective FabK and/or FabL inhibitors would be an effective strategy against several important pathogens, such as Streptococci and Clostridia, but would not be effective against strains expressing FabI. Clearly, organisms like the Pseudomonads and Enterococci that contain both a FabI and FabK would require a combination therapy of enoyl-ACP reductase inhibitors to block cell growth. Thus, enoyl-ACP reductase based therapies can be tailored for specific pathogens based on their expression of FabI and/or FabK and/or FabL.

Therefore, if appearing herein, the following terms shall have the definitions set out below:

As used herein a "FabK" is an enzyme that comprises the consensus sequence of SEQ ID NO:45 and a flavin, and is capable of catalyzing the NAD(P)H-dependent reduction of an enoyl-ACP. One example of a particular FabK is an enoyl reductase from *S. pneumomiae* having the amino acid sequence of SEQ ID NO:2.

As used herein a "FabL" is an enzyme that comprises the consensus sequence of SEQ ID NO:57, does not contain a flavin, and is capable of catalyzing the reduction of an enoyl-ACP. One example of a particular FabL is an enoyl reductase from *Campylobacter jejuni* having the amino acid sequence of SEQ ID NO:52.

As used herein an "active fragment" of a polypeptide has an amino acid sequence that corresponds to that of the corresponding full-length protein except the active fragment has at least one less amino acid than the corresponding full-length protein; furthermore an "active fragment" of an enoyl reductase of the present invention has at least 20% of the enoyl reductase activity of the corresponding full-length protein when determined under at least one set of conditions in which the full-length protein has enoyl reductase activity.

As used herein a protein or fragment thereof has "enoyl reductase activity" when it has the ability to reduce a trans-2-enoyl thioester to an acyl-thioester.

As used herein a "polypeptide" is used interchangably with the term "protein" and denotes a polymer comprising two or more amino acids connected by peptide bonds. Preferably, a polypeptide is further distinguished from a "peptide" with a peptide comprising about twenty or less amino acids, and a polypeptide or protein comprising more than about twenty amino acids.

As used herein the terms "fusion protein" and "fusion peptide" are used interchangeably and encompass "chimeric proteins and/or chimeric peptides" and fusion "intein proteins/peptides". A fusion protein comprises at least a portion of an enoyl reductase of the present invention joined via a peptide bond to at least a portion of another protein or peptide including a second enoyl reductase in a chimeric fusion protein. In a particular embodiment the portion of the enoyl reductase is antigenic. For example fusion proteins can comprise a marker protein or peptide, or a protein or peptide that aids in the isolation and/or purification of an enoyl reductase of the present invention.

As used herein the term "approximately" is used interchangeably with the term "about" and signifies that a value is within ten percent of the indicated value i.e., a protein containing "approximately" 500 amino acid residues can contain between 450 and 550 amino acid residues.

As used herein a "small organic molecule" is an organic compound [or organic compound complexed with an inorganic compound (e.g., metal)] that has a molecular weight of less than 3 Kilodaltons.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

A "vector" is a replicon, such as a plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA can encode a polypeptide of interest, and the cassette and restriction sites are designed to ensure insertion of the cassette in the proper reading frame for transcription and translation.

A cell has been "transfected" or transformed by exogenous or heterologous DNA when such DNA has been introduced inside the cell. A cell has been "transduced" by exogenous or heterologous DNA when the exogenous or heterologous DNA is introduced by a viral vector.

A "heterologous nucleotide sequence" as used herein is a nucleotide sequence that is added to a nucleotide sequence of the present invention by recombinant methods to form a nucleic acid which is not naturally formed in nature. Such nucleic acids can encode fusion (e.g. chimeric) proteins. Thus the heterologous nucleotide sequence can encode peptides and/or proteins which contain regulatory and/or structural properties. In another such embodiment the heterologous nucleotide sequence can encode a protein or peptide that functions as a means of detecting the protein or peptide encoded by the nucleotide sequence of the present invention after the recombinant nucleic acid is expressed. In still another embodiment the heterologous nucleotide sequence can function as a means of detecting a nucleotide sequence of the present invention. A heterologous nucleotide sequence can comprise non-coding sequences including restriction sites, regulatory sites, promoters and the like.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. When referring to a nucleic acid that is DNA, and more specifically a DNA having a particular nucleotide sequence, i.e., SEQ ID NO:1, both the "sense" strand and the complementary "antisense" strand are intended to be included. Thus a nucleic acid that is hybridizable to SEQ ID NO:1, for example, can be either hybridizable to the "sense" strand of SEQ ID NO:1, which is particularly listed in the SEQUENCE LISTING, or to the "antisense" strand which can be readily determined from that SEQUENCE LISTING.

The term nucleic acid molecule, and in particular DNA or RNA molecule, refers only to the primary and secondary structure of the molecule, and does not limit it to any particular tertiary form. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength [see Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"]. The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived [see Sambrook et al., supra, 9.50–10.51]. For hybridization with shorter nucleic acids, i.e., oligonucleotides, the position of mismatches becomes more important, and the length of the oligonucleotide determines its specificity [see Sambrook et al., supra, 11.7–11.8]. Preferably a minimum length for a hybridizable nucleic acid is at least about 12 nucleotides; preferably at least about 18 nucleotides; and more preferably the length is at least about 27 nucleotides; and most preferably at least about 36 nucleotides.

In a specific embodiment, the term "standard hybridization conditions" refers to a $T_m$ of 55° C., and utilizes conditions as set forth above e.g., 5×SSC. In a preferred embodiment, the $T_m$ is 60° C.; in a more preferred embodiment, the $T_m$ is 65° C. "Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eucaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., *Cell* 50:667 (1987)].

As used herein, the term "ortholog" refers to the relationship between proteins that have a common evolutionary origin and differ because they originate from different species or strain. For example, *P. aeruginosa* FabK is an ortholog of *S. pneumoniae* FabK.

The term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not necessarily a common evolutionary origin.

In a specific embodiment, two highly homologous DNA sequences can be identified by their own homology, or the homology of the amino acids they encode. Such comparison of the sequences can be performed using standard software available in sequence data banks. In a particular embodiment two highly homologous DNA sequences encode amino acid sequences having 30%, preferably 50%, more preferably 70% and even more preferably 80% identity. More particularly, two highly homologous amino acid sequences have 30%, preferably 50%, more preferably 70% and even more preferably 80% identity.

Alternatively, two highly homologous DNA sequences can be identified by Southern hybridization experiment under, for example, stringent conditions as defined for that particular system. Defining appropriate hybridization conditions is within the skill of the art. See, e.g., Sambrook et al., supra; DNA Cloning, Vols. I & II, infra; Nucleic Acid Hybridization, infra.

As used herein an amino acid sequence is 100% "homologous" to a second amino acid sequence if the two amino acid sequences are identical, and/or differ only by neutral or conservative substitutions as defined below. Accordingly, an amino acid sequence is 50% "homologous" to a second amino acid sequence if 50% of the two amino acid sequences are identical, and/or differ only by neutral or conservative substitutions.

As used herein, DNA and protein sequence percent identity can be determined using software such as MacVector 6.0.1, Oxford Molecular Group PLC (1996) and the Clustal W algorithm with the alignment default parameters, and default parameters for identity. These commercially available programs can also be used to determine sequence similarity using the same or analogous default parameters.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Enoyl Reductases and Fragments Thereof

The present invention provides isolated and/or recombinant unicellular enoyl reductases and fragments thereof. In a preferred embodiment the unicellular enoyl reductase is a bacterial FabK protein or a FabL protein. FabK and FabL are enoyl-acyl carrier protein reductases that play an essential role in fatty acid synthesis for specific microorganisms and plants by catalyzing the last step in each round of elongation in the type II fatty acid synthase pathway.

The enoyl reductases of the present invention can be from any species, but are preferably from a plant or unicellular organism. Bacterial species of origin for the enoyl reductases include *S. pneumoniae, S. mutans, S. pyogenes, E. faecalis, C. acetobutylicum, C. difficile, P. gingivalis, Ca. cresentus, Ps. aeruginosa, Mycobacterium tuberculosis, H. pylori* and *T. martima*. Examples of nucleic acids and amino acid sequences encoding such enoyl reductases are included in Table 3, below.

In a preferred embodiment the enoyl reducatase is a FabK protein from *S. pneumoniae*. In another embodiment the FabK is a protein encoded by a nucleotide sequence that is hybridizable with the complementary strand of the coding sequence of SEQ ID NO: 1 under standard, and/or stringent conditions. In yet another embodiment the *S. pneumoniae* FabK has an amino acid sequence of SEQ ID NO:2. In still another embodiment the bacterial enoyl reductase is from *S. mutans* and is encoded by a nucleotide sequence having the coding sequence of SEQ ID NO:3. In yet another embodiment the bacterial enoyl reductase has an amino acid sequence of SEQ ID NO:4. In another preferred embodiment the enoyl reducatase is a FabL from *Campylobacter jejuni* having the amino acid sequence of SEQ ID NO:52. The enoyl reductases of the present invention may be used for many purposes including in assays to identify novel drugs such as new antibiotics, and the like, and/or can be used in protein structural and mechanistic studies.

Modified enoyl reductases: The present invention also provides "modified enoyl reductases" i.e., enoyl reductase that are tagged proteins, labeled proteins, intein fusion proteins, and fusion proteins such as a chimeric protein and the like. Such enoyl reductases may be used for example as antigens or as marker proteins. In a particular embodiment of this type, the fusion protein comprises an enoyl reductase that is a FabK protein (or FabK fragment thereof) having an amino acid sequence of SEQ ID NO: 2 or SEQ ID NO:2 comprising one or more conservative amino acid substitutions. In another embodiment of this type, the fusion protein comprises an enoyl reductase or (enoyl reductase fragment thereof) having an anmino acid sequence of SEQ ID NO: 4 or SEQ ID NO:4 comprising one or more conservative amino acid substitutions. Preferably such enoyl reductases or fragments thereof retain their catalytic activity. One particular use of the enoyl reductase fusion proteins of the present invention is for the production of the enoyl reductase-antibodies of the present invention.

An enoyl reductase fusion protein can comprise at least a portion of a non-enoyl reductase protein joined via a peptide bond to at least a portion of an enoyl reductase polypeptide. Alternatively, a chimeric enoyl reductase can be constructed comprising portions of two or more different enoyl reductases. In preferred embodiments a portion of the enoyl reductase is functional, i.e., retaining its catalytic activity. The non-enoyl reductase sequences can be amino- or carboxy-terminal to the enoyl reductase sequences. More preferably, for stable expression of an enoyl reductase fusion protein, such as a FabK fusion protein, the portion of the non-FabK fusion protein (or tag such as a His-tag exemplified below), is joined via a peptide bond to the amino terminus of the FabK protein. A recombinant DNA molecule encoding such a fusion protein comprises a sequence encoding at least a portion of a non-enoyl reductase protein joined in-frame to the enoyl reductase coding sequence, and can encode a cleavage site for a specific protease, e.g., thrombin or Factor Xa, preferably at or close to the enoyl reductase-non-enoyl reductase juncture. In a specific embodiment, the fusion protein is expressed in *Escherichia coli*. Such a fusion protein can be used to isolate the enoyl reductases of the present invention, through the use of an affinity column which is specific for the protein and/or tag fused to the enoyl reductase, such as from *S. pneumoniae* as exemplified below. The purified FabK for example, may then be released from the fusion protein through the use of a proteolytic enzyme and a cleavage site such as has been referred to above.

In one such embodiment, a chimeric enoyl reductase can be prepared, e.g., a glutathione-S-transferase (GST) fusion protein, a maltose-binding (MBP) protein fusion protein, or a poly-histidine-tagged fusion protein, for expression in any cell, or alternatively in a cell-free system. Expression of an enoyl reductase, such as a FabK, as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix, as exemplified below. The fusion protein can be eluted from the specific matrix with appropriate buffers, or by treating with a protease specific for a cleavage site usually engineered between the enoyl reductase and the fusion partner (e.g., GST, MBP, or poly-His) as described above. Alternatively the chimeric enoyl reductase protein may contain the green fluorescent protein, and be used to determine the intracellular localization of the enoyl reductase in the cell.

Genes Encoding Enoyl Reductases

The present invention contemplates isolation of a gene encoding an enoyl reductase of the present invention, such as a FabK or a FabL, including a full length, or naturally occurring form of an enoyl reductase, and antigenic fragments thereof from any plant or microorganism, but preferably a bacterial source. Such nucleic acids may be used for designing primers for RT-PCR, and for making probes that are useful for determining the expression of a fabK or fabL messenger RNA, for example. Similarly, such nucleic acids can be used to determine the expression of the fabK or fabL messenger RNA by Northern Blot analysis, RNA protection assays and the like. As used herein, the term "gene" refers to an assembly of nucleotides that encode a polypeptide, and includes cDNA and genomic DNA nucleic acids. Therefore, the present invention provides the primary structure of genes encoding enoyl reductases such as the *S. pneumoniae* FabK protein exemplified below.

In accordance with the present invention there may be employed conventional molecular biology, microbiology, and recombinant DNA techniques within the skill of the art. Such techniques are explained fully in the literature. [See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed., 1984); *Nucleic Acid Hybridization* B. D. (Hames & S. J. Higgins eds., 1985); *Transcription And Translation* B. D. (Hames & S. J. Higgins, eds., 1984); *Animal Cell Culture* R. I. (Freshney, ed.,1986); *Immobilized Cells And Enzymes* (IRL Press, 1986); B. Perbal, *A Practical Guide To Molecular Cloning* (1984); F. M. Ausubel et al. (eds.), *Current Protocols in Molecular Biology*, John Wiley & Sons, Inc. (1994)].

A gene encoding an enoyl reductase of the present invention whether genomic DNA or cDNA, can be isolated from any source, preferably from a bacterial source. Thus, in view and in conjunction with the present teachings, methods well known in the art, as described above can be used for obtaining enoyl reductase genes from any source (see, e.g., Sambrook et al., 1989, supra). These methods can be supplemented and/or used in the alternative with the use of nucleic acid and/or protein databases (either complete or partially complete) to identify new FabK orthologues for example. Such identification can then lead to the subsequent isolation of the gene and/or protein as exemplified below.

Accordingly, any plant cell and/or microorganism can potentially serve as the nucleic acid source for the molecular cloning of an enoyl reductase gene. The DNA may be obtained by standard procedures known in the art from cloned DNA (e.g., a DNA "library"), and preferably is obtained from an appropriate cDNA library, by chemical synthesis by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from higher genomic DNA may contain regulatory and intron DNA regions in addition to coding regions; clones derived from cDNA will not contain intron sequences. Whatever the source, the gene can be molecularly cloned into a suitable vector for propagation of the gene.

In the molecular cloning of the gene from genomic DNA, DNA fragments can be generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired enoyl reductase gene may be accomplished in a number of ways. For example, the generated DNA fragments may be screened by nucleic acid hybridization to a labeled probe of the present invention [Benton and Davis, *Science* 196:180 (1977); Grunstein and Hogness, *Proc. Natl. Acad. Sci. U.S.A.* 72:3961 (1975)]. For example, a set of oligonucleotides corresponding to the sequence information provided by the present invention can be prepared and used as probes for DNA encoding the FabK exemplified below (e.g., in combination with a poly-T primer for RT-PCR). Preferably, a probe is selected that is highly unique to the FabK of the invention. Those DNA fragments with substantial homology to the probe will hybridize. As noted above, the greater the degree of homology, the more stringent hybridization conditions can be used.

Further selection can be carried out on the basis of the properties of the gene, e.g., if the gene encodes a protein product having the activity, isoelectric point, electrophoretic properties, amino acid composition, or partial amino acid sequence of an enoyl reductase as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for FabK, for example.

An enoyl reductase gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified enoyl reductase DNA, or may be synthetic oligonucleotides designed from the partial amino acid sequence information. Immunoprecipitation analysis or functional assays (e.g., capable of acting as enoyl reductase as defined herein) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against an enoyl reductase such as FabK.

A radiolabeled enoyl reductase cDNA can be synthesized using the selected mRNA (from the adsorbed polysomes) as a template. The radiolabeled mRNA or cDNA may then be used as a probe to identify homologous enoyl reductase DNA fragments from among other genomic DNA fragments.

The present invention also relates to cloning vectors containing genes encoding analogs and derivatives of the enoyl reductases of the present invention, that have the same or homologous functional activity such as the enzymatic activity of FabK, having an amino acid sequence of SEQ ID NO:2, and in particular orthologs thereof from other species. The production and use of derivatives and analogs related to the enoyl reductases of the present invention are within the scope of the present invention. In a specific embodiment, the derivative or analog is functionally active, i.e., capable of acting as enoyl reductase as defined herein.

Enoyl reductase derivatives can be made by altering encoding nucleotide sequences by substitutions, additions or deletions that provide for functionally equivalent molecules. Preferably, derivatives are made that have enhanced or increased functional activity, or greater antigenic specificity.

Due to the degeneracy of nucleotide coding sequences, other DNA sequences which encode substantially the same amino acid sequence as an enoyl reductase gene of the present invention may be used in the practice of the present invention. These include but are not limited to allelic genes, homologous genes from other species, and nucleotide sequences comprising all or portions of the enoyl reductase genes which are altered by the substitution of different codons that encode the same amino acid residue within the sequence, thus producing a silent change. Likewise, the enoyl reductase derivatives of the invention include, but are not limited to, those containing, as a primary amino acid sequence, all or part of the amino acid sequence of an enoyl reductase protein including altered sequences in which functionally equivalent amino acid residues are substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

The amino acids also can be placed in the following similarity groups:

(1) proline, alanine, glycine, serine, and threonine;

(2) glutamine, asparagine, glutamic acid, and aspartic acid;

(3) histidine, lysine, and arginine;

(4) cysteine;

(5) valine, leucine, isoleucine, methionine; and (6) phenylalanine, tyrosine, and tryptophan.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding enoyl reductase derivatives and analogs of the invention can be produced by various methods known in the art. The manipulations which result in their production can occur at the gene or protein level. For example, the cloned enoyl reductase gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an enoyl reductase, care should be taken to ensure that the modified gene remains within the same translational reading frame as the enoyl reductase gene, uninterrupted by translational stop signals, in the gene region where the desired activity is encoded.

Additionally, the FabK-encoding nucleic acid sequence, for example, can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional and/or antigenic activity of the mutated enoyl reductase gene product. Any technique for mutagenesis known in the art can be used, including but not limited to, in vitro site-directed mutagenesis [Hutchinson, et al., *J. Biol. Chem.* 253:6551 (1978), Zoller and Smith, *DNA* 3:479–488 (1984), Oliphant et al., *Gene* 44:177 (1986), and Hutchinson et al., *Proc. Natl. Acad. Sci. U.S.A.* 83:710 (1986)] use of TAB® linkers (Pharmacia), etc. PCR techniques are preferred for site directed mutagenesis [see Higuchi, "Using PCR to Engineer DNA", in *PCR Technology: Principles and Applications for DNA Amplification*, H. Erlich, ed., Stockton Press, Chapter 6, pp. 61–70 (1989) or as described in the Example below].

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pMal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transduction, transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast $2\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

The nucleotide sequence of an enoyl reductase such as the *S. pneumoniae* FabK e.g., having the nucleotide sequence of SEQ ID NO:1, or more preferably the *S. pneumoniae* FabK having the amino acid sequence of SEQ ID NO:2, can also be used to search for highly homologous genes from other species, including fungi using computer data bases containing full or partial nucleic acid sequences (see Table 3). The FabK amino acid sequence of SEQ ID NO:2, for example, can be compared with computer translated plant or fungi sequences, e.g., in the appropriate databases, using software such as GCG and the BLAST search program for example. Matches with highly homologous sequences can then be obtained.

If a matched partial sequence is obtained, it can then be fully sequenced, if it has not been already. Many methods for accomplishing this are known. One such procedure includes performing DNA sequencing reactions that can be assembled on a Beckman Biomek robotic system using standard dye-terminator chemistry, Taq polymerase and thermal cycling conditions described by the vendor [Perking Elmer/Applied Biosystems Division (PE/AB)]. Preferably sequencing is performed multiple times to ensure accuracy. Reaction products can be resolved on PE/ABD model 373 and 377 automated DNA sequencers. Contig assembly can be performed using any number of programs (e.g., Gap4) and a consensus sequence can be further analyzed using the GCG suite of applications. The resulting sequence can then be used in place of, and/or in conjunction with SEQ ID NOs:1 or 2, for example, to identify other partial sequences that contain coding regions of orthologs to FabK.

Plasmids containing the matched sequences can be digested with restriction enzymes in order to release the cDNA inserts. If the plasmid does not contain the full length ortholog, the digests can be purified, e.g., run on an agarose gel and the bands corresponding to the inserts can be cut from the gel and purified (Qiagen Gel Extraction kit). Such purified inserts are likely to contain overlapping regions which can be combined as templates of a PCR reaction using primers which are preferably located outside of the FabK open reading frame. The PCR reaction can be performed by RACE PCR, or by using ELONGASE (and its standard amplification system) supplied by Gibco-BRL, Gaithersburg, Md., under the following standard conditions: 5 minutes at 94° C.; followed by 25 cycles of: 30 seconds at 94° C., 30 seconds at 50° C., and 3.5 minutes at 72° C.; followed by 10 minutes at 72° C. Amplification should yield the expected product which can be ligated into a vector and used to transform an *E. coli* derivative via TA cloning (Invitrogen) for example. A resulting full-length FabK, for example, can be placed into an expression vector and the expressed recombinant FabK can then be assayed for enoyl reductase activity.

Alternatively, plasmids containing matched ortholog fragments can be used to transform competent bacteria (e.g., from Gibco BRL, Gaithersburg Md.). Bacteria can be streaked, then grown up overnight. Plasmid preps can be performed (e.g., Qiagen Corp, Santa Clarita Calif.) and the plasmids can be digested by simultaneous restriction digestion. Products of the digest can be separated by size on an agarose gel, for example, and purified. The corresponding bands cut from these gels can be ligated to form a full-length fabK cDNA and used to transform competent bacteria (DHFalpha) and the resulting plasmid can be purified.

In yet another embodiment, software programs such as the GCG package which includes a motif defining program "FindPatterns" can be used to identify a particular motif common to a family of proteins. This motif can then be used to identify other members of the family from publicly available databases. Using the motifs defined by SEQ ID NO:45 and SEQ ID NO:57, the sequences that were identified are shown in Table 3, below.

Expression of Enoyl Reductases

The present invention provides for expressing the nucleic acids which encode the enoyl reductases and fragments thereof, derivatives or analogs, and/or a functionally active derivative, including a chimeric protein, thereof, that has been inserted into an appropriate expression vector, i.e., a vector which contains the necessary elements for the transcription and translation of the inserted protein-coding sequence. Such elements are termed herein a "promoter." Thus, the nucleic acid encoding a bacterial FabK of the present invention for example is operationally associated with a promoter in an expression vector of the invention (see Example, below). Both cDNA and genomic sequences can be cloned and expressed under control of such regulatory sequences. An expression vector also preferably includes a replication origin. One particular use for such expression vectors is to express a FabK protein in large quantities that can be used for functional and structural studies of the purified protein. The necessary transcriptional and translational signals can be provided on a recombinant expression vector, or they may be supplied by the native gene encoding FabK and/or its flanking regions.

Potential chimeric partners for the enoyl reductases of the present invention include glutathione-S-transferase (GST) or green fluorescent protein which may be useful in monitoring the cellular localization of the enoyl reductases.

Potential host-vector systems include but are not limited to bacterial cell systems, infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant enoyl reductase protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression [See Sambrook et al., 1989, supra]. The cell containing the recombinant vector comprising the nucleic acid encoding the enoyl reductase is cultured in an appropriate cell culture medium under conditions that provide for expression of enoyl reductase by the cell.

Any of the methods previously described, or described in the Example below, for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of the enoyl reductase may be controlled by any promoter/enhancer element known in the art, but these regulatory elements must be functional in the host selected for expression. Promoters which may be used to control enoyl reductase gene expression include, the SV40 early promoter region [Benoist and Chambon, *Nature* 290:304–310 (1981)], the promoter contained in the 3' long terminal repeat of Rous sarcoma virus [Yamamoto, et al., *Cell* 22:787–797 (1980)], the herpes thymidine kinase promoter [Wagner et al., *Proc. Natl. Acad. Sci. U.S.A.* 78:1441–1445 (1981)], the regulatory sequences of the metallothionein gene [Brinster et al., *Nature* 296:39–42 (1982)]; prokaryotic expression vectors such as the β-lactamase promoter [Villa-Kamaroff, et al., *Proc. Natl. Acad. Sci. U.S.A.* 75:3727–3731 (1978)], or the tac promoter [DeBoer, et al., *Proc. Natl. Acad. Sci. U.S.A.* 80:21–25 (1983)]; see also "Useful proteins from recombinant bacteria" in *Scientific American* 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell* 38:639–646 (1984); Ornitz et al., *Cold Spring Harbor Symp. Quant. Biol.* 50:399–409 (1986); MacDonald, *Hepatology* 7:425–515 (1987)]; insulin gene control region which is active in pancreatic beta cells [Hanahan, *Nature* 315:115–122 (1985)], immunoglobulin gene control region which is active in lymphoid cells [Grosschedl et al., *Cell* 38:647–658 (1984); Adames et al., *Nature* 318:533–538 (1985); Alexander et al., *Mol. Cell. Biol.* 7:1436–1444 (1987)], mouse mammary tumor virus control region which is active in testicular, breast, lymphoid and mast cells [Leder et al., *Cell* 45:485–495 (1986)], albumin gene control region which is active in liver [Pinkert et al., *Genes and Devel.* 1:268–276 (1987)], alpha-fetoprotein gene control region which is active in liver [Krumlauf et al., *Mol. Cell. Biol.* 5:1639–1648 (1985); Hammer et al., *Science* 235:53–58 (1987)], alpha 1-antitrypsin gene control region which is active in the liver [Kelsey et al., *Genes and Devel.* 1:161–171 (1987)], beta-globin gene control region which is active in myeloid cells [Mogram et al., *Nature* 315:338–340 (1985); Kollias et al., *Cell* 46:89–94 (1986)], myelin basic protein gene control region which is active in oligodendrocyte cells in the brain [Readhead et al., *Cell* 48:703–712 (1987)], myosin light chain-2 gene control region which is active in skeletal muscle [Sani, *Nature* 314:283–286 (1985)], and gonadotropic releasing hormone gene control region which is active in the hypothalamus [Mason et al., *Science* 234:1372–1378 (1986)].

Expression vectors containing a nucleic acid encoding an enoyl reductase of the invention, for example FabK, can be identified by any number of general approaches including: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding FabK is inserted within the "selection marker" gene sequence of the vector, recombinants containing the FabK insert can be identified by the absence of the selection marker gene function. In the fourth approach, recombinant expression vectors can be identified by assaying for the activity, biochemical, or immunological characteristics of the gene product expressed by the recombinant, provided that the expressed protein assumes a functionally active conformation. For example, the catalytic activity of the FabK can be tested.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX [Smith et al., *Gene* 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or bacterial cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; [see Kaufman, *Current Protocols in Molecular Biology*, 16.12 (1991)]. Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker;

Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the FabK protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification [e.g., glycosylation, cleavage, (e.g., of signal sequence) of proteins]. Appropriate cell lines or host systems can be chosen to ensure the desired modification and processing of the foreign protein expressed. For example, expression in a bacterial system can be used to produce an nonglycosylated core protein product. Expression in yeast can produce a glycosylated product. Furthermore, different vector/host expression systems may affect processing reactions, such as proteolytic cleavages, to a different extent.

Vectors are introduced into the desired host cells by methods known in the art, e.g., transfection, transduction, electroporation, microinjection, cell fusion, DEAE dextran, calcium phosphate precipitation, lipofection (lysosome fusion), use of a gene gun, or a DNA vector transporter [see, e.g., Wu et al., *J. Biol. Chem.* 267:963–9670 (1992), Wu and Wu, *J. Biol. Chem.* 263:14621–14624 (1988), Hartmut et al., Canadian Patent Application No. 2,012,311, filed Mar. 15, 1990].

The present invention also provides cell lines made from cells transfected or transduced with the FabKs of the present invention. In one particular embodiment the cells are bacterial cells.

General Protein Purification Procedures

The purification of FabK using a fusion protein that greatly simplifies the process is exemplified below. However, the present invention also provides a more general classical protein purification protocol. This procedure includes an initial step for purifying the enoyl reductases of the present invention, fragments thereof and related tagged or fusion proteins consisting of lysing the cells containing the enoyl reductases. Cell lysis can be achieved by a number of methods including through the use of a physical means such as a French press, a sonicator, or a blender; or through chemical means including enzymatic extractions (with for example, lysozyme or pancreatin), and/or organic extractions or solubilizations with detergents, such as sodium dodecyl sulfate (SDS), Triton X-100, nonidet P-40 (NP-40), digoxin, sodium deoxycholate, and the like, including mixtures thereof; or through a combination of chemical and physical means. For example, solubilization can be enhanced by sonication of the suspension. Subsequent steps of purification include salting in or salting out, such as in ammonium sulfate fractionations; solvent exclusion fractionations, e.g., an ethanol precipitation; detergent extractions to free the membrane bound enoyl reductases (if any) of the present invention using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl[2-hydroxypropyl]aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as PHENYLSEPHAROSE and a high salt buffer; affinity-binding, using, e.g., placing a substrate or substrate analog on to an activated support; immuno-binding, using e.g., an antibody to a FabK of the present invention bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations are used. Low concentration buffers generally infer 5–25 mM concentrations. High concentration buffers generally infer concentrations of the buffering agent of between 0.1–2M concentrations. Typical buffers can be purchased from most biochemical catalogues and include the classical buffers such as Tris, pyrophosphate, monophosphate and diphosphate and the Good buffers [Good, et al., *Biochemistry*, 5:467 (1966); Good et al. *Meth. Enzymol.*, 24: Part B, 53 (1972); and Fergunson, et. al *Anal. Biochem.* 104:300,(1980)] such as Mes, Hepes, Mops, tricine and Ches.

Materials to perform all of these techniques are available from a variety of sources such as Sigma Chemical Company in St. Louis, Mo.

Antibodies to Enoyl Reductases

According to the present invention, an enoyl reductase such as a bacterial FabK of FabL protein obtained from a natural source or produced recombinantly or by chemical synthesis, and fragments or other derivatives or analogs thereof, including fusion proteins, may be used as an immunogen to generate antibodies that recognize the bacterial FabK or FabL polypeptide. Such antibodies include but are not limited to polyclonal, monoclonal, chimeric, single chain, Fab fragments, and an Fab expression library. The anti-FabK and anti-FabL antibodies of the invention may be cross reactive, e.g., they may recognize a FabK or FabL from different species. Polyclonal antibodies have greater likelihood of cross reactivity. Alternatively, an antibody of the invention may be specific for a single ortholog of the enoyl reductases, such as *S. pneumoniae* FabK.

Various procedures known in the art may be used for the production of polyclonal antibodies to an enoyl reductase of the present invention or derivative or analog thereof. For the production of antibody, various host animals can be immunized by injection with a FabK, for example, or a derivative (e.g., fragment or fusion protein) thereof, including but not limited to rabbits, mice, rats, sheep, goats, etc. In one embodiment, a FabK or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calniette-Guerin) and *Corynebacterium parvum*.

For preparation of monoclonal antibodies directed toward a FabK of the present invention, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Nail. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a rabbit antibody molecule specific for a bacterial FabK, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce FabK-specific single chain antibodies. An additional embodiment of the invention utilizes the techniques described for the construction of Fab expression libraries [Huse et al., Science 246:1275–1281 (1989)] to allow rapid and easy identification of monoclonal Fab fragments with the desired specificity for a FabK or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a FabK, for example the catalytic site, one may assay generated hybridomas for a product which binds to a FabK fragment containing such an epitope. For selection of an antibody specific to a FabK protein from a particular bacterium, one can select on the basis of positive binding with a bacterial FabK expressed by or isolated from cells of that bacterial species.

The foregoing antibodies can be used in methods known in the art relating to the localization and activity of the enoyl reductase, such as FabK, for example using Western blotting, imaging FabK in situ, measuring levels thereof in appropriate physiological samples, etc. using any of the detection techniques mentioned above or known in the art. More particularly, the antibodies of the present invention can be used in flow cytometry studies, in immunohistochemical staining, and in immunoprecipitation which serves to aid the determination of the level of expression of a FabK protein.

In a specific embodiment, antibodies that agonize or antagonize the activity of a bacterial FabK can be generated. Such antibodies can be tested using the assays described herein.

Vaccination and Passive Immune Therapy

Active immunity against bacteria that rely on FabK and/or FabL for fatty acid synthesis can be induced by immunization (vaccination) with an immunogenic amount of FabK or FabL, or an antigenic derivative or fragment thereof, and an adjuvant, wherein the FabK and/or FabL, or antigenic derivative or fragment thereof, is the antigenic component of the vaccine. The protein, or fragment thereof can be conjugated to the carbohydrate capsule or capsules of one or more species of the bacterium. Covalent conjugation of a protein to a carbohydrate is well known in the art. Generally, the conjugation can proceed via a carbodiimide condensation reaction.

The FabK or FabL alone or conjugated to a capsule or capsules cannot cause bacterial infection, and the active immunity elicited by vaccination with the protein according to the present invention can result in both an immediate immune response and in immunological memory, and thus provide long-term protection against infection by the bacterium. The FabK or FabL of the present invention, or antigenic fragments thereof, can be prepared in an admixture with an adjuvant to prepare a vaccine.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA encoding the antigen into tissues of a subject for expression of the antigen by the cells of the subject's tissue. Such vaccines are termed herein "nucleic acid-based vaccines." For example, a naked DNA vector [see, e.g., Ulmer et al., Science 259:1745–1749 (1993), a DNA vector transporter e.g., Wu et al., J. Biol. Chem. 267:963–967 (1992); Wu and Wu, J. Biol. Chem. 263:14621–14624 (1988); Hartmut et al., Canadian Patent Application No. 2,012,311, filed Mar. 15, 1990], or a viral vector containing the desired FabK gene can be injected into tissue. Suitable viral vectors include retroviruses that are packaged in cells with amphotropic host range [see Miller, Human Gene Ther. 1:5–14 (1990); Ausubel et al., Current Protocols in Molecular Biology, §9], and attenuated or defective DNA virus, such as but not limited to herpes simplex virus (HSV) [see, e.g., Kaplitt et al., Molec. Cell. Neurosci. 2:320–330(1991)], papillomavirus, Epstein Barr virus (EBV), adenovirus [see, e.g., Stratford-Perricaudet et al., J. Clin. Invest. 90:626–630 (1992)], adeno-associated virus (AAV) [see, e.g., Samulski et al., J. Virol. 61:3096–3101 (1987); Samulski et al., J. Virol. 63:3822–3828 (1989)], and the like. Defective viruses, which entirely or almost entirely lack viral genes, are preferred. Defective virus is not infective after introduction into a cell.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, and/or a DNA vector transporter [see above, and U.S. Pat. No. 5,916,879, issued Jun. 29, 1999, hereby incorporated by reference in its entirety].

Vaccines of the invention, can be administered by scarification, or via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen. Since immune cells are continually replicating, they are ideal target for retroviral vector-based nucleic acid vaccines, since retroviruses require replicating cells.

Passive immunity can be conferred to an animal subject suspected of having a bacterial infection, for example, by administering antiserum, polyclonal antibodies, or a neutralizing monoclonal antibody against a Gram positive bacterium, for example, to the patient. Although passive immunity does not confer long term protection, it can be a valuable tool for the treatment of a bacterial infection of a subject who has not been vaccinated. Passive immunity is particularly important for the treatment of antibiotic resistant strains of Gram positive bacteria, for example, since no other therapy is available. Preferably, the antibodies administered for passive immune therapy are autologous antibodies. For example, if the subject is a human, preferably the antibodies are of human origin or have been "humanized," in order to minimize the possibility of an immune response against the antibodies.

The active or passive vaccines of the invention can be used alone or together as part of a multi-vaccine regimen to protect an animal subject from infection of a Gram positive bacteria, for example. Thus, a vaccine of the invention can be used in birds, such as chickens, turkeys, and pets; in mammals, preferably a human, although the vaccines of the invention are contemplated for use in other mammalian species, including but not limited to domesticated animals (canine and feline); farm animals (bovine, ovine, equine, caprine, porcine, and the like); rodents; and undomesticated animals.

Assays for Identifying Agonists and Antagonists of FabK

Identification of the FabK protein and the FabL protein provides a basis for screening for drugs capable of specific interaction with the functionally relevant aspects of the protein. For example, an agonist or antagonist can be identified that stimulates or inhibits the FabK or FabL proteins. Since FabK and FabL play an important role in fatty acid synthesis such agonists and antagonists can be tested in a fatty acid synthetic assay as described in the Example below. Accordingly, in addition to rational design of compounds that bind to bacterial FabK or FabL, the present invention contemplates an alternative method for identifying specific agents that bind to FabK or FabL using the various screening assays known in the art.

Thus any screening technique known in the art can be used to screen for agonists or antagonists to the bacterial FabK or FabL proteins. The present invention contemplates screens for small molecule ligands or ligand analogs and mimics, as well as screens for natural ligands that bind to and antagonize FabK or FabL in vivo.

Knowledge of the primary sequence of a bacterial FabK protein of the present invention for example, and the similarity of that sequence with proteins of known function, can provide an initial clue as the agonists or antagonists of the protein. Identification and screening of antagonists is further facilitated by determining structural features of the bacterial FabK protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for binding partners of the enoyl reductase, such as the bacterial FabK protein, that can potentially act as an antagonist of the protein.

The screening can be performed directly using peptides such as those corresponding to the catalytic domain of the bacterial FabK or FabL, or to any fragment and preferably active fragment of the FabK or FabL. Alternatively, chimeric proteins, which contain a fragment of the bacterial FabK or FabL may be used.

Screening can be performed with recombinant cells that express the bacterial FabK or FabL protein, or alternatively, using purified protein, and/or specific structural/functional domains of the bacterial FabK or FabL protein e.g., produced recombinantly, as described above. For example, a labeled bacterial FabK protein can be used to screen libraries, as described in the foregoing references for small molecules that will inhibit the enoyl-ACP binding activity of the bacterial FabK protein.

The effective peptide(s) can be synthesized in large quantities for use in in vivo models and eventually in humans to inhibit the FabK and/or FabL protein and thereby act as a drug that counteracts bacterial infection. It should be emphasized that synthetic peptide production is relatively non-labor intensive, easily manufactured, quality controlled and thus, large quantities of the desired product can be produced quite cheaply. Similar combinations of mass produced synthetic peptides have been used with great success [Patarroyo, Vaccine 10:175–178 (1990)].

There are many additional methods for screening FabK or FabL inhibitors. For example, an enoyl reductase such as an enoyl-ACP reductase could be used with either enoyl-ACP as the substrate or preferably, using a substrate analog such as trans-2-enoyl-N-acetylcysteamine or an analogous enoyl-CoA. The reaction can be followed by oxidation of the reducing cofactor spectrophotometrically or fluorometrically [Heath et al., J. Biol. Chem., 273:30316 (1998); Heath et al., J. Biol. Chem., 274:11110–11114 (1999)] or using gel electrophoresis to separate labeled acyl-ACP products [Heath and Rock, J. Biol. Chem., 271:1833 (1996)]. Assays can also be designed to show FabK-cofactor-drug ternary complexes for example, using radiolabeled cofactor enzyme and drug [Heath et al., *J. Biol. Chem.*, 274:11110–11114 (1999)]. Since *S. pneumonia* FabK binds both NADH and FAD, either cofactor would be applicable. Additionally, FAD analogs including natural analogs such as FMN, or NADH analogs including natural analogs such as NADPH can be employed in certain assays. FabK activity can also be measured by cofactor oxidation in the absence of substrate. Alternatively, since the reaction is reversible, assays monitoring the reverse enzymatic reaction can be performed.

In addition, a scintillation proximity assay, filter precipitation assay, size exclusion assay or other methods that are based on the separation of the protein from a labeled cofactor and/or labeled substrate/product would also provide a reliable method for determining the catalytic activity of the FabK or FabL. Inhibitors would be identified when a significant decrease in the catalytic activity is determined.

As discussed below, the present invention also includes the use of the enoyl reductases and fragments that can be crystallized (e.g., by X-ray crystallography) or are soluble at relatively high concentrations (e.g., for NMR analysis) for rational drug design. Potential effective drugs could be designed by molecular modeling of the FabK or FabL active site and then chemically synthesized or identified in existing drug libraries. Such drugs could be used to inactivate FabK or FabL and therefore, act as an anti-bacterial.

Labels

The reagents that contain the bacterial FabK or FabL proteins, or FabK or FabL fragments can be labeled for use in the screening assays. In one embodiment, the bacterial FabK or FabL proteins, or FabK or FabL fragments may be directly labeled including as part of a fusion protein, e.g., with green fluorescent protein. In another embodiment, a labeled secondary reagent may be used to detect binding of the compound to a solid phase support containing a binding molecule of interest. Binding may be detected by in situ formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluorescein isothiocyanate (FITC), phycoerythrin (PE), Texas red (TR), rhodamine, Lucifer Yellow, AMCA blue, free or chelated lanthanide series salts, especially $Eu^{3+}$, to name a few fluorophores), chemiluminescent molecules, radio-isotopes, or magnetic resonance imaging labels.

Suitable labels include enzymes and proteins such as green fluorescent protein, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

Proteins, including the FabKs and FabLs of the present invention and antibodies thereto, can be labeled by metabolic labeling. Metabolic labeling occurs during in vitro incubation of the cells that express the protein in the presence of culture medium supplemented with a metabolic label, such as [$^{35}S$]-methionine (as described below in the Example) or [$^{32}P$]-orthophosphate. In addition to metabolic (or biosynthetic) labeling with [$^{35}S$]-methionine, the invention further contemplates labeling with [$^{14}C$]-amino acids and [$^{3}H$]-amino acids (with the tritium substituted at non-labile positions).

Solid Supports

A solid phase support for use in the present invention will be inert to the reaction conditions for binding. A solid phase support for use in the present invention must have reactive groups in order to attach a binding partner, such as an oligonucleotide encoding a bacterial FabK or FabL, a bacterial FabK or FabL fragment, or an antibody to a bacterial FabK or FabL, or for attaching a linker or handle which can serve as the initial binding point for any of the foregoing. In another embodiment, the solid phase support may be a useful chromatographic support, such as the carbohydrate polymers SEPHAROSE, SEPHADEX, agarose and agarose beads (as described in the Example below). As used herein, a solid phase support is not limited to a specific type of support. Rather a large number of supports are available and are known to any person having skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In synthesis of oligonucleotides, a silica based solid phase support may be preferred. Silica based solid phase supports are commercially available (e.g., from Peninsula Laboratories, Inc.; and Applied Biosystems, Inc.).

Peptide Synthesis

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149–2154 (1963)], or the base-labile $N^\alpha$-amino protected 9-fluorenylmethoxycarbonyl (Fmoc) amino acids first described by Carpino and Han [*J. Org. Chem.*, 37:3403–3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, enoyl reductases of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

Rational Drug Design

The present invention provides a FabK and a FabL that can be crystallized or alternatively modified (such as proteolytically cleaved to its catalytic core) and then crystallized into a crystal that effectively diffracts X-rays for the determination of the atomic coordinates of the FabK or FabL to a resolution of better than 5.0 Angstroms and preferably to a resolution equal to or better than 3.5 Angstroms. The FabK or FabL can be expressed either as described below in the Example, or as described above. Of course, the FabKs or FabLs provided herein serve only as example, since crystallization can tolerate a broad range of active FabKs and FabLs. Therefore, any person with skill in the art of protein crystallization having the present teachings and without undue experimentation could crystallize a large number of forms of the FabK and FabL from a variety of core FabK or FabL fragments for example, or alternatively using a full length FabK or FabL from a related source. As mentioned above, a FabK or FabL having conservative substitutions in its amino acid sequence is also included in the invention, including a selenomethionine substituted form.

Crystals of the FabK or FabL of the present invention can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used.

Crystals can be characterized by using X-rays produced in a conventional source (such as a sealed tube or a rotating anode) or using a synchrotron source. Methods of characterization include, but are not limited to, precision photography, oscillation photography and diffractometer data collection. Selenium-Methionine may be used, or alternatively a mercury derivative data set (e.g., using PCMB) could be used in place of the Selenium-Methionine derivatization. Cells can be induced to incorporate selenomethionine by suppression of methionine biosynthesis [Doublie, *Methods Enzymol.*, 276:523–530 (1997)].

Structural determinations can be performed by calculating Patterson maps using PHASES [Furey and Swaminathan, *Methods Enzymol.*, 277:590–620 (1997)] for the ethyl-$HgCl_2$ and $Ta_6Br_4$ derivatives and using the Pb-derivative as native for example. The location of a particular site, such as a flavin binding site of the FabK, for example or the entire catalytic site can be derived manually for example, and then confirmed using HEAVY [Terwilliger et al., *Acta Cryst.*, A 43:34–38 (1987)] for each derivative, and cross-confirmed using difference Fourier techniques. Additional sites, as well as sites for heavy-metal derivatives, can be obtained using difference Fourier techniques. The final phasing calculations can be performed using SHARP [LaFortelle et al., *Crystallographic Computing*, (Eds. Bourne and Watenpaugh) 1997)]. If large errors between groups of data from each synchrotron beamline is found, multiple sets from CHESS A1 may need to be initially refined with SHARP. Other groups of data can be subsequently included but with the refined heavy-atom parameters for the previously refined data sets fixed for all subsequent refinements. After each trial refinement, density modification and phase extension can be performed using SOLOMON.

Map interpretation and model building can be performed using O [Jones et al., *Acta Cryst*, A 47:110–119 (1991)]. Refinement calculations can be performed using CNS [Adams et al., *Proc. Natl. Acad. Sci. USA*, 94:5018–5023 (1997)].

Once the three-dimensional structure of a crystal comprising a FabK or FabL is determined, (or determined by an alternative methodology such as NMR) a potential modulator of FabK or FabL can be examined through the use of computer modeling using a docking program such as GRAM, DOCK, or AUTODOCK [Dunbrack et al., *Folding & Design*, 2:27–42 (1997)]. This procedure can include computer fitting of potential modulators to the FabK or FabL to ascertain how well the shape and the chemical structure of the potential modulator will bind to FabK or FabL [Bugg et al., *Scientific American*, Dec.:92–98 (1993); West et al., *TIPS*, 16:67–74 (1995)]. Computer programs can also be employed to estimate the attraction, repulsion, and steric hindrance of the FabK or FabL with a modulator/inhibitor (e.g., the FabK or FabL and a potential stabilizer).

Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially compounds found to bind bacterial FabK or FabL, by high throughput screening for example, can be systematically modified by computer modeling programs until one or more promising potential analogs are identified. In addition, selected analogs can then be systematically modified by computer modeling programs until one or more potential analogs are identified. Such analysis has been shown to be effective in the development of HIV protease inhibitors [Lam et al., Science 263:380–384 (1994); Wlodawer et al., Ann. Rev. Biochem. 62:543–585 (1993); Appelt, Perspectives in Drug Discovery and Design 1:23–48 (1993); Erickson, Perspectives in Drug Discovery and Design 1:109–128 (1993)]. Thus a potential modulator could be obtained by initially screening a random peptide library produced by recombinant bacteriophage for example, (Scott and Smith, Science, 249:386–390 (1990); Cwirla et al., Proc. Natl. Acad. Sci., 87:6378–6382 (1990); Devlin et al., Science, 249:404–406 (1990)]. A peptide selected in this manner would then be systematically modified by computer modeling programs as described above, and then treated analogously to a structural analog as described above.

Once a potential modulator/inhibitor is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. As mentioned above, the de novo synthesis of one or even a relatively small group of specific compounds is reasonable in the art of drug design. The potential modulator can be placed into a standard binding and/or catalytic assay with FabK or FabL, or an active fragment thereof, for example. The fragments can be synthesized by either standard peptide synthesis described above, or generated through recombinant DNA technology or classical proteolysis. Alternatively the corresponding full-length proteins may be used in these assays.

For example, the FabK or a fragment thereof can be attached to a solid support. Methods for placing the FabK on the solid support are well known in the art and include such things as linking biotin to the FabK and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the FabK can be determined. Alternatively, or in addition, the dissociation constant between the labeled potential modulator and the FabK, for example can be determined. Suitable labels for either the bacterial FabK subunit or the potential modulator are exemplified herein. In a particular embodiment, isothermal calorimetry can be used to determine the stability of the bacterial FabK in the absence and presence of the potential modulator.

In another embodiment, a Biacore machine can be used to determine the binding constant of the bacterial FabK or FabL to cofactors, substrates, products or analogs thereof in the presence and absence of the potential modulator. Alternatively, the bacterial FabK or FabL can be immobilized on a sensor chip.

In this case the dissociation constant for the bacterial FabK or FabL can be determined by monitoring changes in the refractive index with respect to time as buffer is passed over the chip. [O'Shannessy et al. Anal. Biochem. 212:457–468 (1993); Schuster et al., Nature 365:343–347 (1993)]. Scatchard Plots, for example, can be used in the analysis of the response functions using different concentrations of a FabK for example. Flowing a potential modulator at various concentrations over the bacterial FabK and monitoring the response function (e.g., the change in the refractive index with respect to time) allows the dissociation constant to be determined in the presence of the potential modulator and the bacterial FabK cofactors and/or substrates or products or their analogs, and thereby indicates whether the potential modulator is either an inhibitor, or an agonist of the bacterial FabK.

In another aspect of the present invention a potential modulator is assayed for its ability to inhibit the bacterial FabK or FabL. A modulator that inhibits the FabK or FabL can then be selected. In a particular embodiment, the effect of a potential modulator on the catalytic activity of bacterial FabK or FabL is determined. The potential modulator is then be added to a bacterial culture to ascertain its effect on bacterial proliferation. A potential modulator that inhibits bacterial proliferation can then be selected.

In a particular embodiment, the effect of the potential modulator on the catalytic activity of the bacterial FabK or FabL is determined (either independently, or subsequent to a binding assay as exemplified above). In one such embodiment, the rate of the enoyl reductase is determined. For such assays the oxidation/reduction of a cofactor can be determined. This assay can be performed using a real-time assay e.g., with a spectrophotometer. Alternatively, the determination can include the withdrawal of aliquots from the incubation mixture at defined intervals and subsequent placing of the aliquots on nitrocellulose paper or on gels. In a particular embodiment the potential modulator is selected when it is an inhibitor of the bacterial FabK.

When suitable potential modulators are identified, a supplemental crystal can be grown which comprises the bacterial FabK or FabL and the potential modulator. Preferably the crystal effectively diffracts X-rays for the determination of the atomic coordinates of the protein-ligand complex to a resolution of better than 5.0 Angstroms, more preferably equal to or better than 3.5 Angstroms. The three-dimensional structure of the supplemental crystal can be determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [J. Navaza, Acta Crystallographics ASO, 157–163 (1994)]. Once the position and orientation are known an electron density map can be calculated using the search model to provide X-ray phases. Thereafter, the electron density is inspected for structural differences and the search model is modified to conform to the new structure. Using this approach, it will be possible to use a crystal of the bacterial FabK or FabL to solve the three-dimensional structures of other bacterial core FabKs or FabLs having pre-ascertained amino acid sequences. Other computer programs that can be used to solve the structures of the bacterial FabK from other organisms include: QUANTA, CHARMM; INSIGHT; SYBYL; MACROMODE; and ICM.

A candidate drug can be selected by performing rational drug design with the three-dimensional structure determined for the supplemental crystal, preferably in conjunction with computer modeling discussed above. The candidate drug (e.g., a potential modulator of bacterial FabK) can then be assayed as exemplified above, or in situ. A candidate drug can be identified as a drug, for example, if it inhibits bacterial proliferation.

A potential inhibitor (e.g., a candidate drug) would be expected to interfere with bacterial growth. Therefore, an assay that can measure bacterial growth may be used to identify a candidate drug.

Methods of testing a potential bactericidal agent (e.g., the candidate drug) in an animal model are well known in the art, and can include standard bactericidal assays. The potential modulators can be administered by a variety of ways including topically, orally, subcutaneously, or intraperitoneally depending on the proposed use. Generally, at least two groups of animals are used in the assay, with at least one group being a control group which is administered the administration vehicle without the potential modulator.

For all of the drug screening assays described herein further refinements to the structure of the drug will generally be necessary and can be made by the successive iterations of any and/or all of the steps provided by the particular drug screening assay.

The present invention also includes the drugs that are obtained by the methods of the present invention.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

THE ENOYL-ACP REDUCTASE II OF STREPTOCOCCUS PNEUMONIAE (FABK) IS A FLAVOPROTEIN THAT CONFERS HIGH LEVEL TRICLOSAN RESISTANCE TO ESCHERICHIA COLI

Introduction

Fatty acid biosynthesis in bacteria is accomplished by a set of discrete proteins that each catalyze a specific step in the pathway and are encoded by individual genes [Rock and Cronan, *Biochim. Biophys. Acta*, 1302:1 (1996)]. The NADH-dependent enoyl-ACP reductase (FabI) catalyzes the last reaction in each cycle of 2-carbon fatty acyl chain elongation. This enzyme plays a role in determining the rate of fatty acid production through feedback regulation by long-chain acyl-ACP end-products of the pathway [Heath and Rock, *J. Biol. Chem.*, 271:1833 (1996)]. As disclosed below, an alternative enzyme has been isolated which carries out the identical catalytic reaction as FabI. The characteristics of this new enzyme are also disclosed.

Methods

Preparation of nucleic acids encoding FabK: The synthetic primers: 5'-TCTAGACATATGAAAACGCGTATTACAGAATT-3' (SEQ ID NO:59) and 5'-GGATCCTAGATACTGGGCACCTTGACC-3' (SEQ ID NO:60) were used to amplify a band of 1030 bp from the chromosome of *S. pneumoniae* strain R6 in a reaction containing 10 μM of each primer, 500 μM dNTPs and 4 mM MgCl$_2$ in 1×Buffer B from Promega. The reaction was heated to 95° C. for 5 minutes to effect lysis of the cells prior to the addition of Taq DNA polymerase to 1.25 U per reaction. 35 cycles of 95° C. for 15 seconds; 55° C. for 15 seconds, and 72° C. for 2 minutes were performed. The PCR product was purified following gel electrophoresis and cloned into the pCR2.1 vector (Invitrogen). The gene was then subcloned into the NdeI and BamHI sites of the plasmid pET-15b (Novagen) to form pET-fabK for inducible expression of FabK with an amino-terminal 6×His-tag. The gene was sequenced to verify that the expected sequence had been obtained. pET-fabK was digested with XbaI and BamHI and the orf subcloned into pBluescript KSII (+) (Stratagene) digested with the same enzymes to create pfabK to constitutively express the His-tagged FabK. *E. coli* strain RJH13 (fabI(Ts)) was transformed with either pBluescript (empty vector), pfabI [Heath et al., *J. Biol. Chem.*, 273:30316 (1998)] or pfabK. Cells were grown at the permissive temperature for the host strain (30° C.), and then individual colonies spotted to LB agar plates and incubated at 42° C. Plasmids pfabI and pfabK complemented the growth phenotype, while no growth was seen when cells were transformed with the empty vector.

Expression and purification of His-FabK in *E. coli* and purification of the protein. The plasmid pET-fabK was transformed into *E. coli* strain BL21-Codon Plus-(DE3)-R1L (Stratagene) and cells were grown at 37° C. in liquid LB medium plus ampicillin (100 μg/ml) and chloramphenicol (34 μg/ml) to a density of approximately 5×10$^8$ cells per milliliter. IPTG was added to a 1 mM concentration and 0.5 mg/ml of riboflavin was added. Growth was continued for 3 hours at 37° C., and the cells were harvested by centrifugation. The cells were then resuspended in 20 mM Tris, pH 7.9 containing 0.5 M NaCl, 1 mM PMSF and 10% glycerol (MCAC buffer) and lysed by adding 0.1 mg/ml lyzozyme and 1% Triton X-100. The extract was then frozen at −70° C. After gently thawing the extract on ice, it was centrifuged at 50,000 rpm in a 70.1 Ti rotor for one hour. Soluble protein was then applied to a 6 ml (bed volume) Ni-NTA column (Qiagen) that had been previously equilibrated with MCAC buffer. The column was then washed with 5 column volumes of MCAC buffer and then 5 column volumes of MCAC buffer plus 40 mM imidazole. The His-tagged protein was eluted with MCAC buffer plus 200 mM imidazole. The purified protein migrated at 36 kDa on SDS gel electrophoresis corresponding to the predicted molecular weight plus the His-tag (predicted size 36,340) and was greater than 98% pure as judged by SDS-PAGE with Coomassie blue staining.

Enzymatic Assays: A reaction mixture containing 100 μM ACP, 1 mM β-mercaptoethanol, 100 μM acetyl-CoA, 50 μM [2-$^{14}$C]malonyl-CoA (56 mCi/mmol), 200 μM NADPH, 200 μM NADH, and 12.5 μg/ml of each FabD, FabH, FabG, FabA and FabZ in 0.1 M sodium phosphate pH 7.0 was incubated at 37° C. for 30 min to generate the trans-2-enoyl-ACP substrate before being aliquoted into individual reaction tubes to which FabK was added to the final amount as indicated for the Figures, above. The final reaction volume was 40 μL. Reactions were then incubated for 30 min at 37° C. and were stopped by placing into an ice slurry. Gel loading buffer was added, and the entire sample was loaded onto a 13% polyacrylamide gel containing 0.5 M urea [Heath and Rock, *J. Biol. Chem.*, 271:1833 (1996)].

Results

Only a single type of enoyl-ACP reductase, typified by the *E. coli* FabI, is known [Bergler et al., *J. Biol. Chem.*, 269:5423 (1994), and Heath and Rock, *J. Biol. Chem.*, 270:26538 (1995)]. As anticipated, FabI is widely distributed in both Gram negative and Gram positive bacteria because enoyl-ACP reduction is a required chemical step for this biosynthetic pathway of saturated fatty acids. However surprisingly, homologs to FabI protein are conspicuously absent from several bacterial genome databases at the TIGR website (http:\\www.tigr.org) (see below, and Table 1).

TABLE 1

OCCURRENCE OF FABI AND FABK IN MICROORGANISMS

| Organism | % Identity to[a] | | |
|---|---|---|---|
| | FabI | FabK | FabL |
| *Escherichia coli* | 100 | — | — |
| *Streptococcus pneumoniae* | — | 100 | — |
| *Aquifex aeolicus* | 49 | — | — |
| *Archeaglobus fugidis* | — | 37 | — |
| *Bacillus subtilis* | 51 | — | 100 |
| *Bordetella pertussis* | 65 | — | — |
| *Campylobacter jejuini* | 47 | — | 41 |
| *Chlamydia pneumoniae* | 34 | — | — |
| *Clostridium acetobutyricum* | — | 58 | — |
| *Haemophilus influenza* | 75 | — | — |
| *Helicobacter pylori* | 45 | — | 40 |
| *Mycobacterium tuberculosis* | 33 | 31 | — |
| *Neisseria gonorrhoeae* | 61 | — | — |
| *Rickettsia prowazekii* | 43 | — | — |
| *Thermatoga maritima* | — | 48 | — |
| *Enterococcus feacalis* | 47 | 68 | — |
| *Pseudomonas aeruginosa* | 69 | 33 | — |
| *Staphylococcus aureus* | 43 | — | — |
| *Streptomyces collinus* | — | — | 38 |

[a]The *E. coli* FabI, *S. pneumoniae* FabK, and *B. subtilus* FabL protein sequences were used to search the dynamically translated unfinished and complete microbial genomes database at NCBI for open reading frames encoding homologous proteins. Open reading frames were identified by using the tblastn algorithm. Criteria for identification were: a highly significant score (expected match = $10^{-30}$ or lower) from the initial search, the presence of an open reading frame encoding a predicted protein of approximately the same size as the characterized proteins, and a satisfactory alignment with FabI and FabK using the PileUp algorithm in the GCG package. The number of identical residues was then scored. — indicates that homologous genes were not detected in an organism with a completely sequenced genome.

FabI homologs are easily recognized in bacterial genomes using BLAST search algorithms (Table 1). However, database searches using the known *E. coli* enoyl-ACP reductase (FabI) protein sequence failed to reveal the presence of a gene encoding a homolog of this protein in any of the Streptococcal genomes including *S. pyogenes*, *S. mutans*, and *S. pneumoniae*, even though the complete genomes for these three Streptococcal strains are essentially fully sequenced. In direct contrast, homologs of all of the other proteins required in fatty acid synthesis (i.e., FabD, FabH, FabG, FabF, Fab Z, ACP and the four subunits of ACC) were all readily recognizable by performing a similiar tblastn search of the identical databases with the corresponding amino acid sequences. Indeed, FabI homologs were also not found in *Clostridium acetobutyricum*, *C. difficile* and *Thermatoga maritima*. Since enoyl-ACP reduction is a required chemical step in the synthesis of an acyl chain by this pathway, these organisms must contain a novel gene that encodes an enoyl-ACP reductase with a distinctly different primary structure than FabI. This gap in the understanding of type II fatty acid synthases and the importance of enoyl-ACP reductase as a target for the development of new therapeutics prompted the investigation of the reductase step in the type II system of *S. pneumoniae*.

Figure 1A:
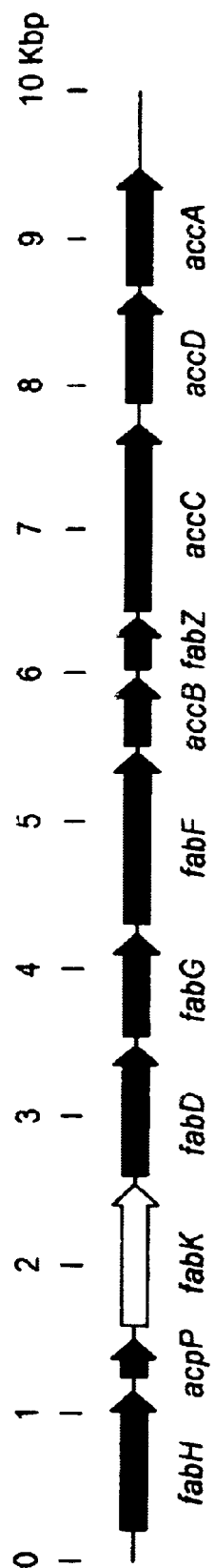

Importantly, all of the other proteins required in fatty acid synthesis were present on a single contig (Contig sp_90 in the Jan. 28, 1999 release). Indeed, the analysis of the fab genes in all three Streptococci genomes revealed that the entire set of fab genes was present in a cluster spanning about 10 kbp (FIG. 1A). A similar fab gene cluster was found in *C. difficile*. Although clusters of fab genes, except fabI, are present in other bacteria such as *B. subtilis* and *E. coli*, these clusters contain only a subset of the required genes and the other fab genes are sprinkled throughout the genome [Rock and Cronan *Biochim. Biophys. Acta*, 1302:1 (1996)].

Further analysis indicated that the genes were clustered together with an apparent open reading frame for an heretofore unreported protein. For example, the order of proteins was: fabH-acpP-unknown-fabD-fabF-fabG-bccP-fabZ-bccA-accD-accA. The unidentified open reading frame contained within the Streptococci and Clostridial clusters was named fabk. FabK is predicted to encode a protein of approximately 34 kDa containing a centrally located FAD binding domain as defined by Nagy et al., [*Proc. Natl. Acad. Sci. U.S.A.*, 89:8966 (1992)] (FIG. 1B). *S. pyogenes* and *S. mutans* had fabK located in the same position in the fab cluster with identity at the protein sequence level to *S. pneumoniae* of 78% and 73%, respectively. Alignment of representative FabK proteins from these organisms revealed highly related amino terminal and central regions and divergent carboxy terminal domains (FIG. 1B). The association of fabK with the Streptococci fab cluster led to the hypothesis that this gene encoded a unique enoyl-ACP reductase.

The unknown protein was used to search the GenBank non-redundant database. The search revealed that FabK was present in a variety of microorganisms including bacteria. Archae, yeast and fungi (Table 1). Indeed, the highest scoring match to a known protein was Expect=4e09 to the 2-nitropropane diooxygenase (SwissProt: 2NPD_WILMR) from yeast *Williopsis saturnus*. Higher scoring hypothetical proteins in several bacteria were noted, most of which had been annotated as nitropropane diooxygenases (e.g., a protein from the archeabacteria *Archaeoglobus fulgidus* with E=7e-46) based on a low level of sequence identity to the yeast protein. Thus, the unknown gene, and related genes in other bacteria, shared some sequence homology to the 2NPD of yeast, but this similarity was not sufficient to conclude that the proteins had the same function. Importantly, the nitropropane diooxygenase activity of 2NPD was believed to be an ancillary role for the enzyme in yeast, indicating that heretofore, the natural role of this enzyme had not be ascertained.

The identification of FabK as an enoyl-ACP reductase was established by biochemical characterization of the purified enzyme. The fabk gene was amplified from *S. pneumoniae* strain R6 chromosomal DNA and cloned into the pET-15b expression vector (see Methods, above). The yellow protein was purified to homogeneity and exhibited an apparent molecular weight equivalent to the predicted mass of FabK plus the His-tag (FIG. 2A). Spectral analysis of freshly purified FabK revealed the presence of 0.8 moles of FAD per mole of FabK monomer (FIG. 2B). The FAD cofactor was tightly, but not covalently bound, and the FAD content was progressively reduced during prolonged dialysis. The protein was tested for enoyl-ACP reductase activity in an in vitro coupled assay system utilizing purified *E. coli* Fab proteins to generate the trans-2-butenoyl-ACP substrate (FIG. 2C). FabK had a specific activity of 66±4 nmole product formed/min/mg FabK in this assay (FIG. 2D). NADH was an essential requirment for enoyl-ACP reductase and FabK carried out the slow oxidation of NADH, but not NADPH, in the absence of substrate. Triclosan (25

μg/ml) did not inhibit FabK activity in the in vitro assay. These data illustrate that FabK is a flavoprotein that possesses trans-2-enoyl-ACP reductase activity.

FabK was able to functionally replace the FabI enoyl-ACP reductase in vivo. It also confers triclosan resistance to *E. coli*. FabI is the only enoyl reductase in *E. coli* and strain RJH13 harbors a fabI(Ts) allele and fails to grow at 42° C. [Heath et al., *J. Biol. Chem.*, 273:30316 (1998)]. Transformation of strain RJH13 with pfabK restored the ability of strain RJH13 to grow at the non-permissive temperature, thus illustrating that FabK substituted for all of the functions of FabI (see Methods, above). The pfabK plasmid was then introduced into the wild-type *E. coli* strain W3110. Strain W3110 was sensitive to triclosan and either the presence of the pFabI multi-copy plasmid or the chromosomal fabI [G93V] mutant increased triclosan resistance (Table 2). This result is understood based on the observation that while the FabI[G93V] mutant fails to form a high-affinity FabI-NAD$^+$-triclosan ternary complex, it is still inhibited by the drug [Heath et al., *J. Biol. Chem.*, 274:11110–11114 (1999)]. Introduction of the pfabK plasmid into strain W3110 shifted the minimum inhibitory concentration (MIC) for triclosan to greater than 2 mg/ml (Table 2). These cells are completely resistant to triclosan confirming that FabK is not a target for this drug and that FabI is the only target for triclosan in *E. coli*. *P. aeruginosa* is unique among Gram negative bacteria in that it contains both FabI and FabK in its genome (Table 1), and is completely refractory to triclosan inhibition [Bhargava and Leonard, *Am. J. Infect. Control*, 24:209 (1996)]. Furthermore, the FabI protein from *P. aeruginosa* is highly susceptible to triclosan in vitro and disruption of the fabI gene in this organism does not result in an obvious growth phenotype [Hoang and Schweizer, *J. Bacteriol.*, 181:5489 (1999)] suggesting the presence of a second enoyl reductase.

TABLE 2

FabK expression confers triclosan resistance to makes *E. coli*.

| Strain | MIC[1](ug/ml) |
|---|---|
| *E. coli* W3110/pBluescript | 0.25 |
| *E. coli* RJR108 (fabI[G93V])[b] | 16 |
| *E. coli* W3110/pfabI[c] | 2 |
| *E. coli* W3110/pfabK[c] | >2,000 |
| *S. pneumoniae* R6 | 2 |

[a]Minimum inhibitory concentrations for *E. coli* strains were tested by spotting at least six single colonies onto a series of LB agar plates containing different concentrations of triclosan. The *S. pneumoniae* MIC was determined by spreading 10 μL of culture just entering stationary phase onto brain heart infusion plates containing triclosan. The MIC reported in each case is the concentration of triclosan at which no growth was observed in at least three separate experiments. The *S. pneumoniae* MIC was similar to that previously published for Streptococci [Bhargava and Leonard, Am. J. Infect. Control, 24:209 (1996)].
[b]Strain RJH108 was a spontaneously occurring triclosan resistant derivative of W3110 [Heath et al., J. Biol. Chem., 273:30316 (1998)].
[c]pfabI expresses the His-tag FabI from *E. coli* [Heath et al., J. Biol. Chem., 273:30316 (1998)] and pfabK expresses the His-tag FabK protein using the same vector and construction method as employed for pfabI.

Interestingly, FabK does not confer the same high level of triclosan resistance to *S. pneumoniae* (Table 2) and other Gram positive bacteria that contain fabK [Bhargava and Leonard, *Am. J. Infect. Control*, 24:209 (1996)]. These data suggest that triclosan has a second target in Gram positive bacteria that is absent from Gram negative organisms. The triclosan MIC for *S. pneumoniae* and *B. subtilis* are both about 2 μg/ml which is about an order of magnitude higher than typical for Gram negative bacteria (Table 2) [Bhargava and Leonard, *Am. J. Infect. Control*, 24:209 (1996)]. This suggests that the Gram positive FabI can be compensated for by FabK or FabL up to the concentration of triclosan required to inhibit the second, less sensitive triclosan target.

The yeasts *W. saturnus* and *Saccharomyces cerevisiae* (ORF YJR149w) also contain fabK homologs (Table 1). These FabKs are less closely related to *S. pneumoniae* fabK than the bacterial proteins (Table 1) and the eukaryotic enzymes contain inserts of approximately 30 and 8 amino acids that are also observed in the *B. subtilis* and *S. aureus* FabKs (FIG. 1). The *W. saturnus* enzyme has been purified and characterized as a NADH-dependent FAD-containing 2-nitropropane dioxygenase [Tchorzewski et al., *Eur. J. Biochem.*, 226:841 (1994)]. Nitropropane is an industrial environmental pollutant, the enzyme has a low turnover rate, and the nitropropane substrate forms a covalent adduct with the FAD cofactor that inactivates the enzyme [Heasley and Fitzpatrick, *Biochein. Biophys. Res. Commun.*, 225:6 (1996); Gadda et al., *J. Biol. Chem.*, 272:5563 (1997); Gadda and Fitzpatrick, *Biochemistry*, 37:6154 (1998); and Gadda and Fitzpatrick, *Arch. Biochem. Biophys.*, 363:309 (1999)]. These observations argue that this enzyme performs another function in the cells [Tchorzewski et al., *Eur. J. Biochem.*, 226:841 (1994) and Heasley and Fitzpatrick, *Biochem. Biophys. Res. Commun.*, 225:6 (1996); Gadda et al., *J. Biol. Chem.*, 272:5563 (1997); Gadda and Fitzpatrick, *Biochemistry*, 37:6154 (1998); and Gadda and Fitzpatrick, *Arch. Biochem. Biophys.*, 363:309 (1999)].

The significance of the FAD cofactor in FabK is not immediately obvious. Most flavoproteins do not have a NAD(P)H binding site. Instead, FAD is either oxidized or reduced through its interaction with an electron transport flavoprotein. The acyl-CoA dehydrogenase protein family is not structurally related to FabK, but may provide clues to the FabK mechanism. Most of these enzymes catalyze the first step in fatty acid β-oxidation (the reverse reaction of FabI/K) [Thorpe and Kim, *FASEB J.*, 9:718 (995)]; however, a member of this family from Ascaris mitochondria actually carries out enoyl-CoA reduction (the FabI/K forward reaction) [Komuniecki et al., *J. Biol. Chem.*, 260:4770 (1985); Komuniecki et al., *Biochim. Biophys. Acta*, 975:127 (1989); and Duran et al., *J. Biol. Chem.*, 268:22391 (1993)]. These enzymes exist as homotetramers containing one molecule of FAD per subunit. A key feature of these soluble enzymes is that they interact with a low molecular weight flavoprotein, which in turn, shuttles reducing equivalents between the dehydrogenase/reductase and the membrane-associated electron transport chain [Thorpe and Kim, *FASEB J.*, 9:718 (1995) and Komuniecki et al., *J. Biol. Chem.*, 260:4770 (1985); Komuniecki et al., *Biochim. Biophys. Acta*, 975:127 (1989); and Duran et al., *J. Biol. Chem.*, 268:22391 (1993)]. The unique FabK structure may permit the enoyl reductase step of fatty acid synthesis to receive reducing equivalents from either NADH or the electron transport chain depending on the energy balance of the cell.

A characteristic of the FabKs of the present invention is the following sequence motif:

P(I,V)XX(G,A)(G,P)MX{6,9}A(P,A,G,S,T)(P,A,G,S,T)
V(S,A)XXGGX{22,28}T(Q, N,E,D)XPF(G,A)
VX{90,105}P(V,I)(I,V)(A,G)(A,S)
GGXXXXXXXXAX(F,L)XLG AXXXXXGTR (SEQ ID NO:45)

(1) Amino acids are defined using the one letter code, and "X"=any amino acid
(2) The first conserved prolyl residue is preferably 11 to 50 residues from the amino terminal residue
(3) Allowable substitutions at a particular position are in parenthesis: i.e. "(G, A)" means that a Gly or an Ala residue are found at that particular position.

(4) An "X { }" indicates the number (range) of the preceding residue is repeated and that any amino acid can be found in that span: i.e. X{6,9} indicates that there should be a span of 6 to 9 residues having any amino acid residue.

The motif can be defined as for "FindPatterns" in the GCG package . Using this pattern the only sequences found in the non-redundant database were those identified as FabK herein. All of the FabK proteins disclosed herein were identified as having this consensus sequence, whereas no other proteins were found to contain the consensus sequence. This consensus sequence can be depicted in the alternative manner: SEQ ID NO:45 A FabK Consensus Sequence Pro $Xaa_1$ $Xaa_2$ $Xaa_3$ $Xaa_4$ $Xaa_5$ Met $Xaa_6$ Ala $Xaa_7$ $Xaa_8$ Val $Xaa_9$ $Xaa_{10}$ $Xaa_{11}$ Gly Gly $Xaa_{12}$ Thr $Xaa_{13}$ $Xaa_{14}$ Pro Phe $Xaa_{15}$ Val $Xaa_{16}$ Pro $Xaa_{17}$ $Xaa_{18}$ $Xaa_{19}$ $Xaa_{20}$ Gly Gly $Xaa_{21}$ $Xaa_{22}$ $Xaa_{23}$ $Xaa_{24}$ $Xaa_{25}$ $Xaa_{26}$ $Xaa_{27}$ $Xaa_{28}$ Ala $Xaa_{29}$ $Xaa_{30}$ $Xaa_{31}$ Leu Gly Ala $Xaa_{32}$ $Xaa_{33}$ $Xaa_{34}$ $Xaa_{35}$ $Xaa_{36}$ Gly Thr Arg where: $Xaa_1$ is Ile or Val, $Xaa_2$ is any amino acid, $Xaa_3$ is any amino acid, $Xaa_4$ is Gly or Ala, $Xaa_5$ is Gly or Pro, $Xaa_6$ is at least 6 but less than 10 amino acids and they can be any amino acid, $Xaa_7$ is Pro, Ala, Gly, Ser, or Thr, $Xaa_8$ is Pro, Ala, Gly, Ser, or Thr, $Xaa_9$ is Ser or Ala, $Xaa_{10}$ is any amino acid, $Xaa_{11}$ is any amino acid, $Xaa_{12}$ is at least 22 but less than 29 amino acids and they can be any amino acid, $Xaa_{13}$ is Gln, Asn, Glu, or Asp, $Xaa_{14}$ is any amino acid, $Xaa_{15}$ is Gly or Ala, $Xaa_{16}$ is at least 90 but less than 106 amino acids and they can be any amino acid, $Xaa_{17}$ is either Ile or Val, $Xaa_{18}$ is either Ile or Val, $Xaa_{19}$ is either Ala or Gly, $Xaa_{20}$ is either Ala or Ser, $Xaa_{21}$ is any amino acid, $Xaa_{22}$ is any amino acid, $Xaa_{23}$ is any amino acid, $Xaa_{24}$ is any amino acid, $Xaa_{25}$ is any amino acid, $Xaa_{26}$ is any amino acid, $Xaa_{27}$ is any amino acid, $Xaa_{28}$ is any amino acid, $Xaa_{29}$ is any amino acid, $Xaa_{30}$ is either Phe or Leu, $Xaa_{31}$ is any amino acid, $Xaa_{32}$ is any amino acid $Xaa_{33}$ is any amino acid, $Xaa_{34}$ is any amino acid, $Xaa_{35}$ is any amino acid, and $Xaa_{36}$ is any amino acid.

A consensus portion of FabK proteins without the flavin binding domain (FBD) that can be used to prepare antigenic fragments specific for FabK proteins is:

P(I,V)XX(G,A)(G,P)MX{6,9}A(P,A,G,S,T)(P,A,G,S,T) V(S,A)XXGG X{22,28}T(Q,N,E,D)XPF(G,A)V (SEQ ID NO:46)

This consensus sequence can be depicted in the alternative manner: SEQ ID NO:46

Pro $Xaa_1$ $Xaa_2$ $Xaa_3$ $Xaa_4$ $Xaa_5$ Met $Xaa_6$ Ala $Xaa_7$ $Xaa_8$ Val $Xaa_9$ $Xaa_{10}$ $Xaa_{11}$ Gly Gly $Xaa_{12}$ Thr $Xaa_{13}$ $Xaa_{14}$ Pro Phe $Xaa_{15}$ Val where $Xaa_1$ is Ile or Val, $Xaa_2$ is any amino acid, $Xaa_3$ is any amino acid, $Xaa_4$ is Gly or Ala, $Xaa_5$ is Gly or Pro, $Xaa_6$ is at least 6 but less than 10 amino acids and they can be any amino acid, $Xaa_7$ is Pro, Ala, Gly, Ser, or Thr, Xaa8 is Pro, Ala, Gly, Ser, or Thr, $Xaa_9$ is Ser or Ala, $Xaa_{10}$, is any amino acid, $Xaa_{11}$, is any amino acid, $Xaa_{12}$ is at least 22 but less than 29 amino acids and they can be any amino acid, $Xaa_{13}$ is Gln, Asn, Glu, or Asp, $Xaa_{14}$ is any amino acid, and $Xaa_{15}$ is Gly or Ala.

The present invention further includes the identification of another enoyl reductase, FabL: enoyl reductase III, that complements the growth of E. coli strain RJH13, (which contains a temperature-sensitive FabI), and that can confers complete triclosan resistance to E. coli. FabL has significant amino acid sequence similarity to FabI from E. coli, (about 30% identical overall) indicating that FabI and FabL are both members of a larger family of proteins termed the short chain alcohol dehydrogenase/reductases (SDR). SDR proteins have approximately 30% amino acid identity with each other. One key feature of an SDR that lacks enoyl reductase activity is the consensus amino acid sequence Tyr Xaa Xaa Xaa Lys (SEQ ID NO:61) in its active site. The corresponding SDRs that are enoyl reductases have the amino acid sequence Tyr Xaa Xaa Xaa Xaa Xaa Xaa Lys (SEQ ID NO:62) in their active site.

FabL has the enoyl reductase type consensus sequence suggesting that it may be an SDR enoyl reductase. However, such limited structural information alone cannot allow the identification since the overall identity of SDRs are low and the family size is large. Therefore, a nucleic acid encoding FabL was cloned from *B. subtilis* (prior gene designation from genomic sequencing project=ygaA; unidentified dehydrogenase) and shown that it complements the growth of *E. coli*(fabI(Ts)) strain RJH13, and that it confers complete triclosan resistance to E. coli. These results demonstrate that FabL is indeed a FabI-like protein.

FabL proteins have the following consensus sequence:
G(A,G,S,P,T)(P,A,G,T,S)RG(I,V,L,M)GX{100,120}AQ (E,Q,N,D)AXKXMX {118,24}YXXXXXXKXA (V,I, L,M)E(T,A,S,P,G)XX(K,R,H)Y (SEQ ID NO:57)

This consensus sequence can be depicted in the alternative manner: SEQ ID NO:57 A FabL Consensus Sequence Gly $Xaa_1$ $Xaa_2$ Arg Gly $Xaa_3$ Gly $Xaa_4$ Ala GDn $Xaa_5$ Ala $Xaa_6$ Lys $Xaa_7$ Met $Xaa_8$ Tyr $Xaa_9$ $Xaa_{10}$ $Xaa_{11}$ $Xaa_{12}$ $Xaa_{13}$ $Xaa_{14}$ Lys $Xaa_{15}$ Ala $Xaa_{16}$ Glu $Xaa_{17}$ $Xaa_{18}$ $Xaa_{19}$ $Xaa_{20}$ Tyr where $Xaa_1$ is either Ala, Gly, Ser, Pro, or Thr, $Xaa_2$ is either Pro, Ala, Gly, Thr or Ser, $Xaa_3$ is either Ile, Val, Leu, or Met, $Xaa_4$ is at least 100 but less than 121 amino acids and they can be any amino acid, $Xaa_5$ is either Glu,Gln, Asn or Asp, $Xaa_6$ is any amino acid, $Xaa_7$ is any amino acid, $Xaa_8$ is at least 18 but less than 25 amino acids and they can be any amino acid, $Xaa_9$ is any amino acid, $Xaa_{10}$ is any amino acid $Xaa_{11}$ is any amino acid $Xaa_{12}$ is any amino acid, $Xaa_{13}$ is any amino acid, $Xaa_{14}$ is any amino acid, $Xaa_{15}$ is any amino acid, $Xaa_{16}$ is either Val, Ile, Leu, or Met, $Xaa_{17}$ is either Thr,Ala,Ser, Pro, or Gly, $Xaa_{18}$ is any amino acid, $Xaa_{19}$ is any amino acid, and $Xaa_{20}$ is either Lys, Arg, or His.

A region that can distinguish FabL from FabI is:
G(A,G,S,P,T)(P,A,G,T,S)RG(I,V,L,M)GX (SEQ ID NO:58)

This consensus sequence can be depicted in the alternative manner: SEQ ID NO:58

Gly $Xaa_1$ $Xaa_2$ Arg Gly $Xaa_3$ Gly $Xaa_4$ where $Xaa_1$ is either Ala, Gly, Ser, Pro, or Thr, $Xaa_2$ is either Pro, Ala, Gly, Thr, Ser $Xaa_3$ is either Ile, Val, Leu, or Met, and $Xaa_4$ is any amino acid.

The amino acid sequence SEQ ID NO:58 can be used to make antigenic fragments that are specific for FabL proteins for example.

Unlike, FabK proteins, certain FabL proteins have been previously described but their activity as enoyl reductases have not been disclosed for the most part. Thus the Helicobacter FabL protein has been described in the context of its similarity to known genes only, as an α-hydroxysteroid dehydrogenase (a member of the SDR family), and has not been characterized biochemically. The lone exception may be the Streptomyces FabL protein which was identified as a NADPH-dependent 1-cyclohexenylcarbonyl CoA reductase [Wang et al.,*J. Bacteriol*. 178 (23), 6873–6881 (1996)]. The protein is has been reported to be involved in the conversion of shikimic acid to cyclohexanecarboxylic acid, which is used for cyclohexyl fatty acid biosynthesis and polyketide (ansatrienin) biosynthesis.

TABLE 3

Identification of Enoyl Reductases from Assorted Unicellular Organisms

| Organism | Nucleic Acid | Amino Acid |
| --- | --- | --- |
| S. pneumoniae | SEQ ID NO:1 | SEQ ID NO:2 |
| S. mutans | SEQ ID NO:3 | SEQ ID NO:4 |
| S. pyogenes | SEQ ID NO:5 | SEQ ID NO:6 |
| E. faecalis | SEQ ID NO:9 | SEQ ID NO:10 |
| C. acetobutylicum | SEQ ID NO:11 | SEQ ID NO:12 |
| C. difficile | SEQ ID NO:13 | SEQ ID NO:14 |
| P. gingivalis | SEQ ID NO:15 | SEQ ID NO:16 |
| Ca. Cresentus | SEQ ID NO:17 | SEQ ID NO:18 |
| Ps. Aeruginosa | SEQ ID NO:19 | SEQ ID NO:20 |
| Mycobacterium tuberculosis rv3553 | SEQ ID NO:27 | SEQ ID NO:28 |
| Mycobacterium tuberculosis rv0021c | SEQ ID NO:29 | SEQ ID NO:30 |
| T. maritima | SEQ ID NO:33 | SEQ ID NO:34 |
| H. pylori | SEQ ID NO:35 | SEQ ID NO:36 |
| A. fulgidis | SEQ ID NO:37 | SEQ ID NO:38 |
| Consensus Sequence (plus *FBD) | | SEQ ID NO:45 |
| Consensus Sequence (minus FBD) | | SEQ ID NO:46 |
| St. aureus NCTC | SEQ ID NO:47 | SEQ ID NO:48 |
| Bacillus subtilis (FabL) | SEQ ID NO:49 | SEQ ID NO:50 |
| Campylobacter jejuni (FabL) | SEQ ID NO:51 | SEQ ID NO:52 |
| Helicobacter pylori (FabL) | SEQ ID NO:53 | SEQ ID NO:54 |
| Streptomyces collinus FabL | SEQ ID NO:55 | SEQ ID NO:56 |
| Consensus Sequence (FabL) | | SEQ ID NO:57 |
| Consensus Sequence (FabL) | | SEQ ID NO:58 |

*FBD is short for the flavin binding domain.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

---

What is claimed is:

1. An isolated polypeptide that has at least 80% identity with a bacterial enzyme comprising an amino acid sequence selected from the group consisting of SEQ ID NO: 4, SEQ ID NO: 6, SEQ ID NO: 12, SEQ ID NO: 14, SEQ ID NO:16, SEQ ID NO:18, and SEQ ID NO:20; wherein said polypeptide binds a flavin prosthetic group and has enoyl reductase activity.

2. The isolated polypeptide of claim 1 wherein said amino acid sequence is SEQ ID NO: 4.

3. The isolated polypeptide of claim 1 wherein said amino acid sequence is SEQ ID NO: 6.

4. The isolated polypeptide of claim 1 wherein said amino acid sequence is SEQ ID NO: 12.

5. The isolated polypeptide of claim 1 wherein said amino acid sequence is SEQ ID NO: 14.

6. The isolated polypeptide of claim 1 wherein said amino acid sequence is SEQ ID NO: 16.

7. The isolated polypeptide of claim 1 wherein said amino acid sequence is SEQ ID NO: 18.

8. The isolated polypeptide of claim 1 wherein said amino acid sequence is SEQ ID NO: 20.

* * * * *